United States Patent

Tseng

Patent Number: 5,952,266
Date of Patent: Sep. 14, 1999

[54] HERBICIDAL KETALS AND SPIROCYCLES

[75] Inventor: Chi-Ping Tseng, Wilmington, Del.

[73] Assignee: E. I. du Pont de Nemours and Company, Wilmington, Del.

[21] Appl. No.: 08/983,596

[22] PCT Filed: Jun. 19, 1996

[86] PCT No.: PCT/US96/10623

§ 371 Date: Dec. 29, 1997

§ 102(e) Date: Dec. 29, 1997

[87] PCT Pub. No.: WO97/01550

PCT Pub. Date: Jan. 16, 1997

Related U.S. Application Data

[60] Provisional application No. 60/000,668, Jun. 29, 1995, and provisional application No. 60/012,991, Mar. 7, 1996.

[51] Int. Cl.$^6$ .......................... A01N 43/02; A01N 43/56; C07D 335/04; C07D 231/00

[52] U.S. Cl. .......................... 504/288; 504/280; 549/23; 548/364.4

[58] Field of Search .............................. 549/23; 504/288, 504/280; 548/364.4

[56] References Cited

U.S. PATENT DOCUMENTS

| | | | |
|---|---|---|---|
| 5,468,878 | 11/1995 | Nasuno et al. | 549/23 |
| 5,480,858 | 1/1996 | Sakamoto et al. | 504/288 |

FOREIGN PATENT DOCUMENTS

| | | |
|---|---|---|
| 0 283 261 A2 | 9/1988 | European Pat. Off. |
| 0 629 623 A1 | 12/1994 | European Pat. Off. |
| 0 712 853 A1 | 5/1996 | European Pat. Off. |
| 0 728 756 A1 | 8/1996 | European Pat. Off. |
| WO 94/04524 | 6/1993 | WIPO |
| WO 94/08988 | 8/1993 | WIPO |
| WO 95/04054 | 2/1995 | WIPO |
| WO 95/13275 | 5/1995 | WIPO |

Primary Examiner—Deborah C. Lambkin

[57] ABSTRACT

Compounds of Formula (I), and their agriculturally suitable salts, are disclosed which are useful for controlling undesired vegetation wherein Q is (Q-1) or (Q-2); $R^1$ and $R^2$ are each independently $C_1$–$C_6$ alkoxy, $C_2$–$C_6$ haloalkoxy, $C_1$–$C_6$ alkylthio or $C_2$–$C_6$ haloalkylthio; or $R^1$ and $R^2$ are taken together to form —$X^1$—$(CH_2)_r$$X^2$—, —$(CH_2)_s$—$X^3$—, —$(CH_2)_t$—$X^3$—$CH_2$—, —$(CH_2)_v$—$X^3$—$CH_2CH_2$— or —$(CH_2)_w$—, each group optionally substituted with at least one member selected from 1–6 halogen, 1–6 $CH_3$ and one $C_1$—$C_3$ alkoxy; or $R^1$ and $R^2$ are taken together to form —O—$N(C_1$–$C_3$ alkyl)—$CHR^{12}$—$CH_2$— or —O—N=$CHR^{12}$—$CH_2$—, each group optionally substituted with at least one member selected from 1–2 halogen and 1–2 $CH_3$; or $R^1$ and $R^2$ are taken together with the carbon to which they are attached to form C(=O) or C(=S); and $R^3$–$R^{10}$, $X^1$–$X^3$, X, Y, Z, k, m, p, q, r, s, t, v, w, and x are as defined in the disclosure. Also disclosed are compositions containing the compounds of Formula (I) and a method for controlling undesired vegetation which involves contacting the vegetation or its environment with an effective amount of a compound of Formula (I).

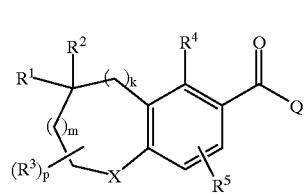

(I)

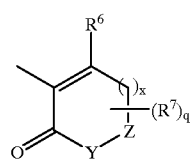

(QI)

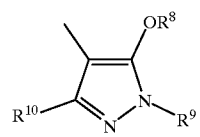

(Q2)

14 Claims, No Drawings

HERBICIDAL KETALS AND SPIROCYCLES

This application is a 371 of PCT/US96/10623 filed Jun. 19, 1996. Provisional application No. 60/000,668 filed Jun. 29, 1995. Provisional application No. 60/012,991 filed Mar. 7, 1996.

BACKGROUND OF THE INVENTION

This invention relates to certain ketals and spirocycles, their agriculturally suitable salts and compositions, and methods of their use for controlling undesirable vegetation.

The control of undesired vegetation is extremely important in achieving high crop efficiency. Achievement of selective control of the growth of weeds especially in such useful crops as rice, soybean, sugar beet, corn (maize), potato, wheat, barley, tomato and plantation crops, among others, is very desirable. Unchecked weed growth in such useful crops can cause significant reduction in productivity and thereby result in increased costs to the consumer. The control of undesired vegetation in noncrop areas is also important. Many products are commercially available for these purposes, but the need continues for new compounds which are more effective, less costly, less toxic, environmentally safer or have different modes of action.

EP 293,261 discloses heterocycles of Formula i as herbicides:

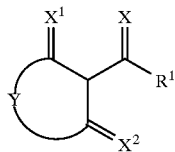

i wherein

X, $X^1$ and $X^2$ are independently O or S;

$R^1$ is a monocyclic or fused-bicyclic heterocyclic group optionally substituted by one or more groups selected from oxo, mercapto, halo, nitro, cyano, amino, mono- or dialkylamino, amido, alkyl, alkenyl, alkynyl, cycloalkyl, haloalkyl, haloalkoxy, aryl, hydroxy, alkoxy, alkoxycarbonyl, alkylcarbonyl, mono- or dialkylcarbamoyl, alkylthio, alkylsulfinyl, alkylsulfonyl, sufonamido, alkylcarbonyloxy, alkylcarbonylamino or heterocyclyl; and Y is, inter alia, $C_2$–$C_4$ alkylene.

The ketals and spirocycles of the present invention are not disclosed in this reference.

SUMMARY OF THE INVENTION

This invention is directed to compounds of Formula I including all geometric and stereoisomers, agriculturally suitable salts thereof, agricultural compositions containing them and their use for controlling undesirable vegetation:

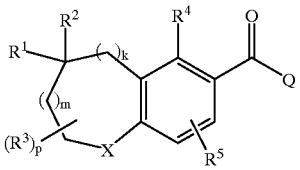

I wherein

Q is

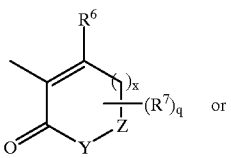

Q-1 or

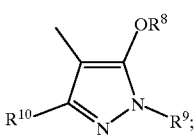

Q-2

$R^1$ and $R^2$ are each independently $C_1$–$C_6$ alkoxy, $C_2$–$C_6$ haloalkoxy, $C_1$–$C_6$ alkylthio or $C_2$–$C_6$ haloalkylthio; or $R^1$ and $R^2$ are taken together to form —$X^1$—$(CH_2)_r$—$X^2$—, —$(CH_2)_s$—$X^3$—, —$(CH_2)_t$—$X^3$—$CH_2$—, —$(CH_2)_v$—$X^3$—$CH_2CH_2$— or —$(CH_2)_w$—, each group optionally substituted with at least one member selected from 1–6 halogen, 1–6 $CH_3$ and one $C_1$–$C_3$ alkoxy; or $R^1$ and $R^2$ are taken together to form —O—N($C_1$–$C_3$ alkyl)—$CHR^{12}$—$CH_2$— or —O—N=$CHR^{12}$—$CH_2$—, each group optionally substituted with at least one member selected from 1–2 halogen and 1–2 $CH_3$; or $R^1$ and $R^2$ are taken together with the carbon to which they are attached to form C(=O) or C(=S);

$X^1$ and $X^2$ are each independently O, S or N($C_1$–$C_3$ alkyl);

$X^3$ is O or S;

each $R^3$ is independently H or $CH_3$;

$R^4$ and $R^5$ are each independently H, $C_1$–$C_6$ alkyl, $C_1$–$C_6$ haloalkyl, $C_1$–$C_6$ alkoxy, $C_1$–$C_6$ haloalkoxy, $C_1$–$C_6$ alkylthio, $C_1$–$C_6$ haloalkylthio, $C_1$–$C_6$ alkylsulfinyl, $C_1$–$C_6$ haloalkylsulfinyl, $C_1$–$C_6$ alkylsulfonyl, $C_1$–$C_6$ haloalkylsulfonyl, halogen, cyano or nitro;

$R^6$ is $OR^{11}$, $C_1$–$C_6$ alkylthio, $C_1$–$C_6$ haloalkylthio, $C_1$–$C_6$ alkylsulfinyl, $C_1$–$C_6$ haloalkylsulfinyl, $C_1$–$C_6$ alkylsulfonyl, $C_1$–$C_6$ haloalkylsulfonyl, cyano, cyanato, thiocyanato or halogen;

each $R^7$ is independently $C_1$–$C_3$ alkyl, $C_1$–$C_3$ alkoxy, $C_1$–$C_3$ alkylthio or halogen; or when two $R^7$ are attached to the same carbon atom, then said $R^7$ pair can be taken together to form —$OCH_2CH_2O$—, —$OCH_2CH_2CH_2O$—, —$SCH_2CH_2S$— or —$SCH_2CH_2CH_2S$—, each group optionally substituted with 1–4 $CH_3$;

$R^8$ is H, $C_1$–$C_6$ alkyl, $C_1$–$C_6$ haloalkyl, $C_2$–$C_6$ alkoxyalkyl, formyl, $C_2$–$C_6$ alkylcarbonyl, $C_2$–$C_6$ alkoxycarbonyl, $C_2$–$C_6$ alkylaminocarbonyl, $C_3$–$C_7$ dialkylaminocarbonyl, $C_1$–$C_6$ alkylsulfonyl or $C_1$–$C_6$ haloalkylsulfonyl; or $R^8$ is benzoyl or phenylsulfonyl, each optionally substituted with $C_1$–$C_3$ alkyl, halogen, cyano or nitro;

$R^9$ is H, $C_1$–$C_6$ alkyl, $C_1$–$C_6$ haloalkyl, $C_3$–$C_6$ alkenyl or $C_3$–$C_6$ alkynyl; or $R^9$ is phenyl or benzyl, each optionally substituted on the phenyl ring with $C_1$–$C_3$ alkyl, halogen, cyano or nitro;

$R^{10}$ is H, $C_1$–$C_6$ alkyl, $C_1$–$C_6$ haloalkyl, halogen, cyano or nitro;

$R^{11}$ is H, $C_1$–$C_6$ alkyl, $C_1$–$C_6$ haloalkyl, $C_2$–$C_6$ alkoxyalkyl, formyl, $C_2$–$C_6$ alkylcarbonyl, $C_2$–$C_6$ alkoxycarbonyl, $C_2$–$C_6$ alkylaminocarbonyl, $C_3$–$C_7$ dialkylaminocarbonyl, $C_1$–$C_6$ alkylsulfonyl or $C_1$–$C_6$ haloalkylsulfonyl; or $R^{11}$ is benzoyl or phenylsulfonyl, each optionally substituted with $C_1$–$C_3$ alkyl, halogen, cyano or nitro;

$R^{12}$ is $C_1$–$C_3$ alkyl; or $R^{12}$ is phenyl optionally substituted with $C_1$–$C_3$ alkyl, halogen, cyano or nitro;

X is $S(O)_n$, O or $NR^{13}$;

$R^{13}$ is H, $C_1$–$C_3$ alkyl, $C_3$–$C_4$ alkenyl, $C_3$–$C_4$ alkynyl, formyl, $C_2$–$C_3$ alkylcarbonyl, $C_2$–$C_3$ alkoxycarbonyl or $C_1$–$C_2$ alkylsulfonyl;

Y is O; S; NH; $N(C_1$–$C_3$ alkyl); or $CH_2$ optionally substituted with $R^7$ when q is other than 0;

Z is a direct bond; O; $S(O)_z$; NH; $N(C_1$–$C_3$ alkyl); or $CH_2$ optionally substituted with $R^7$ when q is other than 0; provided that when Y is O, S, NH or $N(C_1$–$C_3$ alkyl), then Z is a direct bond or $CH_2$ optionally substituted with $R^7$;

k and m are each independently 0, 1 or 2, provided that the sum of k and m is 0, 1 or 2;

n and p are each independently 0, 1 or 2;

q is 0, 1, 2, 3 or 4;

r is 2, 3 or 4;

s is 2, 3, 4 or 5;

t is 1, 2, 3 or 4;

v is 2 or 3;

w is 2, 3, 4, 5 or 6;

x is 1 or 2; and z is 0, 1 or 2;

provided that
(i) when X is $S(O)_n$, Q is Q-1 and $R^1$ and $R^2$ are independently $C_1$–$C_6$ alkoxy, $C_2$–$C_6$ haloalkoxy, $C_1$–$C_6$ alkylthio or $C_2$–$C_6$ haloalkylthio or are taken together with the carbon to which they are attached to form C(=O), then n is 1 or 2; and
(ii) when X is O or $NR^{13}$ and $R^1$ and $R^2$ are independently $C_1$–$C_6$ alkoxy, $C_2$–$C_6$ haloalkoxy, $C_1$–$C_6$ alkylthio or $C_2$–$C_6$ haloalkylthio or are taken together with the carbon to which they are attached to form C(=O), then Q is Q-2.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. The term "1–6 $CH_3$" indicates that one to six of the available positions for that substituent may be methyl; the terms "1–4 $CH_3$" and "1–2 $CH_3$" are defined analogously. "Alkenyl" includes straight-chain or branched alkenes such as 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)$, $CH_3CH_2S(O)$, $CH_3CH_2CH_2S(O)$, $(CH_3)_2CHS(O)$ and the different butylsulfinyl, pentylsulfinyl and hexylsulfinyl isomers. Examples of "alkylsulfonyl" include $CH_3S(O)_2$, $CH_3CH_2S(O)_2$, $CH_3CH_2CH_2S(O)_2$, $(CH_3)_2CHS(O)_2$ and the different butylsulfonyl, pentylsulfonyl and hexylsulfonyl isomers. "Alkylamino", "dialkylamino", and the like, are defined analogously to the above examples.

The term "halogen", either alone or in compound words such as "haloalkyl", includes fluorine, chlorine, bromine or iodine. The term "1–6 halogen" indicates that one to six of the available positions for that substituent may be halogen which are independently selected; the term "1–2 halogen" is defined analogously. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkoxy", "haloalkylthio", and the like, are defined analogously to the term "haloalkyl". Examples of "haloalkoxy" include $CF_3O$, $CCl_3CH_2O$, $HCF_2CH_2CH_2O$ and $CF_3CH_2O$. Examples of "haloalkylthio" include $CCl_3S$, $CF_3S$, $CCl_3CH_2S$ and $ClCH_2CH_2CH_2S$. Examples of "haloalkylsulfinyl" include $CF_3S(O)$, $CCl_3S(O)$, $CF_3CH_2S(O)$ and $CF_3CF_2S(O)$. Examples of "haloalkylsulfonyl" include $CF_3S(O)_2$, $CCl_3S(O)_2$, $CF_3CH_2S(O)_2$ and $CF_3CF_2S(O)_2$.

The total number of carbon atoms in a substituent group is indicated by the "$C_i$–$C_j$" prefix where i and j are numbers from 1 to 7. For example, $C_1$–$C_3$ alkylsulfonyl designates methylsulfonyl through propylsulfonyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$. Examples of "alkylcarbonyl" include $C(O)CH_3$, $C(O)CH_2CH_2CH_3$ and $C(O)CH(CH_3)_2$. Examples of "alkoxycarbonyl" include $CH_3OC(=O)$, $CH_3CH_2OC(=O)$, $CH_3CH_2CH_2OC(=O)$, $(CH_3)_2CHOC(=O)$ and the different butoxy- or pentoxycarbonyl isomers.

When a compound is substituted with a substituent bearing a subscript that indicates the number of said substituents can exceed 1, said substituents (when they exceed 1) are independently selected from the group of defined substituents.

When a group contains a substituent which can be hydrogen, for example $R^4$ or $R^{11}$, then, when this substituent is taken as hydrogen, it is recognized that this is equivalent to said group being unsubstituted.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the present invention comprises compounds selected from Formula I and agriculturally suitable salts thereof. The compounds of the invention may be present as a mixture of stereoisomers, individual stereoisomers, or as an optically active form.

Some compounds of this invention can exist as one or more tautomers. One skilled in the art will recognize, for example, that compounds of Formula Ia (Formula I where Q is Q-1) wherein $R^6$ is $OR^{11}$ and $R^{11}$ is H can also exist as other tautomers as shown below. One skilled in the art will recognize that said tautomers often exist in equilibrium with each other. As these tautomers interconvert under environmental and physiological conditions, they provide the same useful biological effects. The present invention includes mixtures of such tautomers as well as the individual tautomers of compounds of Formula I.

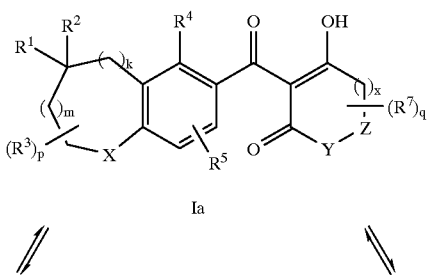

Ia (where $R^6$ is $OR^{11}$ and $R^{11}$ is H)

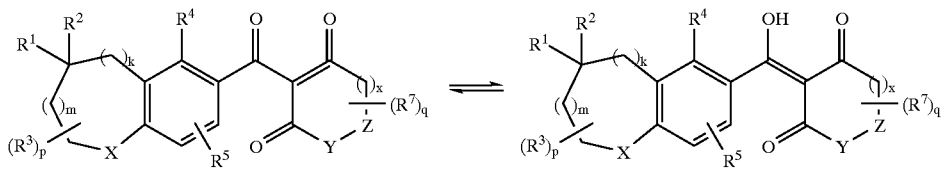

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The salts of the compounds of the invention also include those formed with organic bases (e.g., pyridine, ammonia, or triethylamine) or inorganic bases (e.g., hydrides, hydroxides, or carbonates of sodium, potassium, lithium, calcium, magnesium or barium) when the compound contains an acidic group such as an enol.

Preferred compounds for reasons of better activity and/or ease of synthesis are:

Preferred 1. Compounds of Formula I above, and agriculturally suitable salts thereof, wherein:

each $R^7$ is independently $C_1$–$C_3$ alkyl or halogen;

X is $S(O)_n$;

Y and Z are independently $CH_2$ optionally substituted with $R^7$;

k is 0; and x is 1.

Preferred 2. Compounds of Preferred 1 wherein:

$R^1$ and $R^2$ are independently $C_1$–$C_6$ alkoxy, $C_2$–$C_6$ haloalkoxy, $C_1$–$C_6$ alkylthio or $C_2$–$C_6$ haloalkylthio; or $R^1$ and $R^2$ are taken together to form —$X^1$—$(CH_2)_r$—$X^2$— optionally substituted with at least one member selected from 1–6 halogen and 1–6 $CH_3$; or $R^1$ and $R^2$ are taken together with the carbon to which they are attached to form C(=O);

$X^1$ and $X^2$ are both O or both S;

m is 1 or 2; and r is 2 or 3.

Preferred 3. Compounds of Preferred 2 wherein:

$R^4$ and $R^5$ are independently H, $C_1$–$C_3$ alkyl or halogen;

$R^7$ is $C_1$–$C_3$ alkyl;

$R^9$ is H, $C_1$–$C_6$ alkyl or $C_3$–$C_6$ alkenyl;

$R^{10}$ is H;

$R^{11}$ is H, formyl, $C_2$–$C_6$ alkylcarbonyl, $C_2$–$C_6$ alkoxycarbonyl, $C_2$–$C_6$ alkylaminocarbonyl, $C_3$–$C_7$ dialkylaminocarbonyl, $C_1$–$C_6$ alkylsulfonyl or $C_1$–$C_6$ haloalkylsulfonyl; or $R^{11}$ is benzoyl or phenylsulfonyl, each optionally substituted with $C_1$–$C_3$ alkyl, halogen, cyano or nitro; and n is 2.

Preferred 4. Compounds of Preferred 3 wherein:

$R^1$ and $R^2$ are each methoxy; or $R^1$ and $R^2$ are taken together to form —$X^1$—$(CH_2)_r$—$X^2$—; or $R^1$ and $R^2$ are taken together with the carbon to which they are attached to form C(=O);

$X^1$ and $X^2$ are O;

$R^4$ and $R^5$ are independently H, methyl or halogen;

$R^6$ is $OR^{11}$;

$R^8$ is H or $C_1$–$C_2$ alkylsulfonyl; or $R^8$ is benzoyl or phenylsulfonyl, each optionally substituted with $C_1$–$C_3$ alkyl, halogen, cyano or nitro;

$R^{11}$ is H or $C_1$–$C_2$ alkylsulfonyl; or $R^{11}$ is benzoyl or phenylsulfonyl, each optionally substituted with $C_1$–$C_3$ alkyl, halogen, cyano or nitro; and m is 1; and r is 2.

Preferred 5. Compounds of Preferred 4 wherein:

$R^5$ is methyl or halogen and is attached to the phenyl ring position adjacent to the —$S(O)_n$— moiety.

Preferred 6. Compounds of Preferred 5 wherein:

Q is Q-1.

Preferred 7. Compounds of Preferred 6 wherein:

Q is Q-2.

Most preferred are compounds of Preferred 2 selected from the group:

2-[(2,3-dihydrospiro[4H-1-benzothiopyran-4,2'-[1,3]
dioxolan]-6-yl)carbonyl]-1,3-cyclohexanedione S,S-
dioxide;

(2,3-dihydrospiro[4H-1-benzothiopyran-4,2'-[1,3]
dioxolan]-6-yl)(1-ethyl-5-hydroxy-1H-pyrazol-4-yl)
methanone S,S-dioxide;

2-[(2,3-dihydro-5,8-dimethylspiro[4H-1-benzothiopyran-
4,2'-[1,3]dioxolan]-6-yl)carbonyl]-1,3-
cyclohexanedione S,S-dioxide;

(2,3-dihydro-5,8-dimethylspiro[4H-1-benzothiopyran-4,
2'-[1,3]dioxolan]-6-yl)(1-ethyl-5-hydroxy-1H-pyrazol-
4-yl)methanone S,S-dioxide;

6-[(1-ethyl-5-hydroxy-1H-pyrazol4-yl)carbonyl]-2,3-
dihydro-5,8-dimethyl-4H-1-benzothiopyran-4-one 1,1-
dioxide;

2-[(2,3-dihydro-5,8-dimethylspiro[4H-1-benzothiopyran-
4,2'-[1,3]dioxolan]-6-yl)carbonyl]-1,3-
cyclohexanedione; and (2,3-dihydro-5,8-dimethylspiro[4H-1-benzothiopyran-4,
2'-[1,3]dioxolan]-6-yl)(1-ethyl-5-hydroxy-1H-
pyrazol4-yl)methanone.

This invention also relates to herbicidal compositions
comprising herbicidally effective amounts of the compounds
of the invention and at least one of a surfactant, a solid
diluent or a liquid diluent. The preferred compositions of the
present invention are those which comprise the above pre-
ferred compounds.

This invention also relates to a method for controlling
undesired vegetation comprising applying to the locus of the
vegetation herbicidally effective amounts of the compounds
of the invention (e.g., as a composition described herein).
The preferred methods of use are those involving the above
preferred compounds.

DETAILS OF THE INVENTION

The compounds of Formula I can be prepared by one or
more of the following methods and variations as described
in Schemes 1–22. The definitions of Q, $R^1$–$R^{13}$, $X^1$–$X^3$, X,
Y, Z, k, m, n, p, q, r, s, t, v, w, x and z in the compounds of
Formulae I–XVIII below are as defined above in the Sum-
mary of the Invention. Compounds of Formulae Ia–Ic are
various subsets of the compounds of Formula I, and all
substituents for Formulae Ia–Ic are as defined above for
Formula I. For example, compounds of Formula Ia below
are compounds of Formula I wherein Q is Q-1.

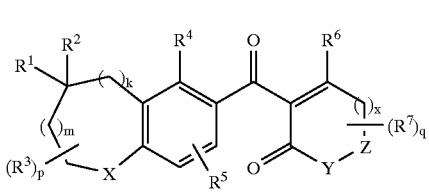

Ia

Scheme 1 illustrates the preparation of compounds of
Formula Ia ($R^1$ and $R^2$ are other than taken together with the
carbon to which they are attached to form C(=O) and
C(=S), $R^6$=$OR^{14}$ and $R^{14}$ is the same as $R^{11}$ as described
in the Summary of the Invention, but not H) whereby a
compound of Formula Ia, ($R^1$ and $R^2$ are other than taken
together with the carbon to which they are attached to form
C(=O) and C(=S), $R^6$=OH) is reacted with a reagent of
Formula II in the presence of a base wherein $X^4$ is chlorine,
bromine, fluorine, trifluoromethanesulfonate or acetate, and
$R^{14}$ is as previously defined. The coupling is carried out by
general methods known in the art; see for example, K.
Nakamura, et al., WO 95/04054.

Scheme 1

Ia ($R^1$ and $R^2$ are other than taken together
with the carbon to which they are attached     +   $R^{14}X^{14}$ 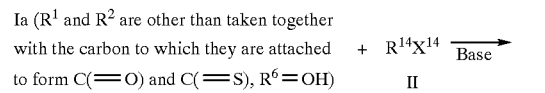
to form C(=O) and C(=S), $R^6$=OH)                II

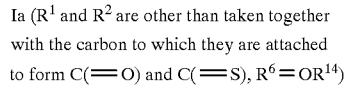

Ia ($R^1$ and $R^2$ are other than taken together
with the carbon to which they are attached
to form C(=O) and C(=S), $R^6$=$OR^{14}$)

Scheme 2 illustrates the preparation of compounds of
Formula Ia ($R^1$ and $R^2$ are other than taken together with the
carbon to which they are attached to form C(=O) and
C(=S), $R^6$=$S(O)_yR^{15}$; y=1 or 2; and $R^{15}$=$C_1$–$C_6$ alkyl or
$C_1$–$C_6$ haloalkyl) whereby a compound of Formula Ia ($R^1$
and $R^2$ are other than taken together with the carbon to
which they are attached to form C(=O) and C(=S), and
$R^6$=$SR^{15}$) is reacted with an oxidizing reagent such as
peroxyacetic acid, m-chloroperoxybenzoic acid, potassium
peroxymonosulfate or hydrogen peroxide (the reaction may
be buffered with a base such as sodium acetate or sodium
carbonate). The oxidation is carried out by methods gener-
ally known in the art; see for example, B. M. Trost, et al., *J.
Org. Chem.* (1988), 53, 532; B. M. Trost, et al., *Tetrahedron
Lett.* (1981), 21, 1287; and S. Patai, et al., *The Chemistry of
Sulphones and Sulphoxides*, John Wiley & Sons.

Scheme 2

Ia ($R^1$ and $R^2$ are other than taken together     Oxidizing
with the carbon to which they are attached         Agent
to form C(=O) and C(=S), $R^6$=$SR^{15}$)        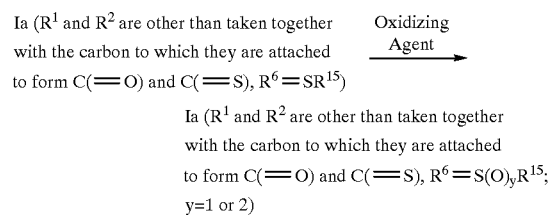

Ia ($R^1$ and $R^2$ are other than taken together
with the carbon to which they are attached
to form C(=O) and C(=S), $R^6$=$S(O)_yR^{15}$;
y=1 or 2)

Compounds of Formula Ia ($R^1$ and $R^2$ are other than taken
together with the carbon to which they are attached to form
C(=O) and C(=S), $R^6$=$SR^{15}$, CN, SCN, OCN or $OR^{16}$;
$R^{15}$ is as defined previously; and $R^{16}$ is $C_1$–$C_6$ alkyl, $C_1$–$C_6$
haloalkyl or $C_2$–$C_6$ alkoxyalkyl) can be prepared by one
skilled in the art from a compound of Formula Ia, ($R^1$ and
$R^2$ are other than taken together with the carbon to which
they are attached to form C(=O) and C(=S), and
$R^6$=halogen) by treatment with a nucleophilic reagent of
Formula III (MSR$^{15}$, MCN, MSCN, MOCN or MOR$^{16}$;
M=Na, Cu, K or Li) as shown in Scheme 3 using general
methods well documented in the literature (see for example,
S. Miyano, et al., *J. Chem. Soc., Perkin Trans.* 1 (1976),
1146; P. H. Nelson, and J. T. Nelson, *Synthesis* (1992), 12,
1287–1291; S. Muller, et al., DE 4241999-A1).

Scheme 3

Ia ($R^1$ and $R^2$ are other than taken together
with the carbon to which they are attached
to form C(=O) and C(=S), $R^6$ = halogen) + MSR$^{15}$
or
MOR$^{16}$
or
MCN
or
MSCN
or
MOCN
III
⟶
Ia ($R^1$ and $R^2$ are other than taken together
with the carbon to which they are attached
to form C(=O) and C(=S), $R^6$ = SR$^{15}$CN,
SCN, OCN or OR$^{16}$)

Compounds of Formula Ia ($R^1$ and $R^2$ are other than taken together with the carbon to which they are attached to form C(=O) and C(=S), and $R^6$=halogen) can be prepared by reacting a compound of Formula Ia ($R^1$ and $R^2$ are other than taken together with the carbon to which they are attached to form C(=O) and C(=S), and $R^6$=OH) with a halogenating reagent such as oxalyl bromide or oxalyl chloride (Scheme 4). This conversion is carried out by general methods known in the art; see for example, S. Muller, et al., WO 94/13619; S. Muller, et al., DE 4241999-A1.

Scheme 4

Ia ($R^1$ and $R^2$ are other than taken together
with the carbon to which they are attached
to form C(=O) and C(=S), $R^6$ = OH)
⟶ Halogenating reagent
(e.g., oxalyl bromide,
oxalyl chloride)

Ia ($R^1$ and $R^2$ are other than taken together
with the carbon to which they are attached
to form C(=O) and C(=S), $R^6$ = halogen)

Scheme 5 illustrates the preparation of compounds of Formula Ia ($R^1$ and $R^2$ are taken together with the carbon to which they are attached to form C(=O) whereby a compound of Formula Ia ($R^1$ and $R^2$ are independently $C_1$–$C_6$ alkoxy or $R^1$ and $R^2$ are taken together to form —O—(CH$_2$)$_r$—O—) is stirred in hydrochloric acid or hydrobromic acid aqueous solution (0.1 N to 12 N) at temperatures between 0° C. and 100° C. for a period of time ranging from 30 minutes to 3 days. This conversion is carried out by methods known in the art (or by slight modification of these methods): for example; see P. A. Grieco, et al., *J. Am. Chem. Soc.* (1977), 99, p 5773; P. A. Grieco, et al., *J. Org. Chem.* (1978), 43, p 4178.

Scheme 5

Ia

Ia ($R^1$ and $R^2$ are independently
$C_1C_6$ alkoxy or $R^1$ and $R^2$ are
taken together to form —O—(CH$_2$)$_r$O—)
⟶ HCl/H$_2$O
or HBr/H$_2$O Ia ($R^1$ and $R^2$ are taken together with the
carbon to which they are attached to
form C(=O))

Scheme 6 illustrates the preparation of compounds of Formula Ia ($R^1$ and $R^2$ are other than taken together with the carbon to which they are attached to form C(=O) and C(=S), and $R^6$=OH) whereby an enol ester of Formula IVa ($R^1$ and $R^2$ are other than taken together with the carbon to which they are attached to form C(=O) and C(=S)) and/or its regioisomer of Formula IVb are reacted with a base such as triethylamine in the presence of a catalytic amount of a cyanide source (e.g., acetone cyanohydrin or potassium cyanide). This rearrangement is carried out by general methods known in the art; see for example, W. J. Michaely, EP 0369803-A1; D. Cartwright, et al., EP 0283261-B1.

Scheme 6

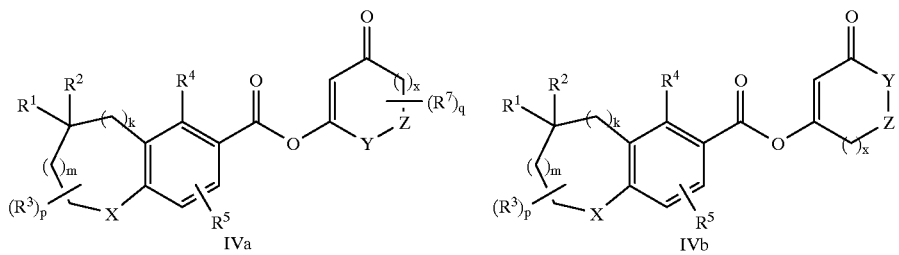

IVa        IVb ($R^1$ and $R^2$ are other than
taken together with the carbon
to which they are attached
to form C(=O) and C(=S))

-continued

Base (e.g., triethylamine) | Cyanide source in catalytic amount (e.g., acetone cyanohydrin or potassium cyanide)

↓

Ia ($R^1$ and $R^2$ are other than taken together with the carbon to which they are attached to form C(=O) and C(=S), $R^6$=OH)

Enol esters of Formula IVa ($R^1$ and $R^2$ are other than taken together with the carbon to which they are attached to form C(=O) and C(=S)) and/or its regioisomer of Formula IVb can be prepared by reacting a dicarbonyl compound of Formula V with an acid chloride of Formula VI ($R^1$ and $R^2$ are other than taken together with the carbon to which they are attached to form C(=O) and C(=S)) in the presence of a slight molar excess of a base such as triethylamine in an inert organic solvent such as acetonitrile, methylene chloride or toluene at temperatures between 0° C. and 110° C. (Scheme 7). This type of coupling is carried out by general methods known in the art (or by slight modification of these methods): for example, see W. J. Michaely, EP 0369803-A1; D. Cartwright, et al., EP 0283261-B 1.

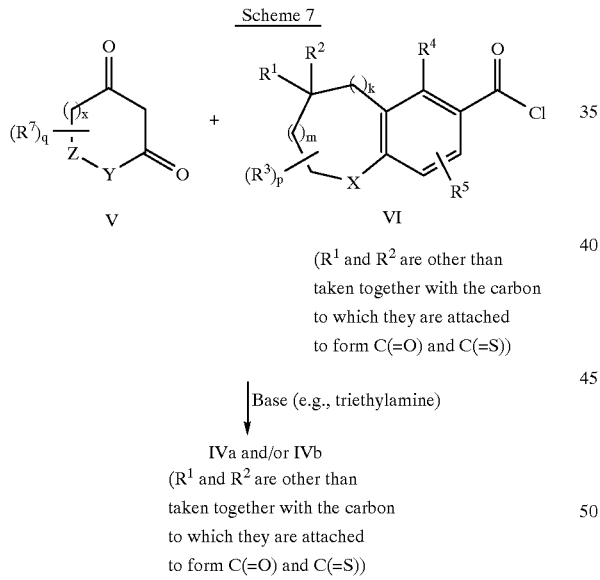

The acid chlorides of Formula VI ($R^1$ and $R^2$ are other than taken together with the carbon to which they are attached to form C(=O) and C(=S)) can be prepared by reacting an acid of Formula VII ($R^1$ and $R^2$ are other than taken together with the carbon to which they are attached to form C(=O) and C(=S)) with oxalyl chloride (or thionyl chloride) and a catalytic amount of dimethylformamide (Scheme 8). This chlorination is well known in the art; see for example, W. J. Michaely, EP 0369803-A1.

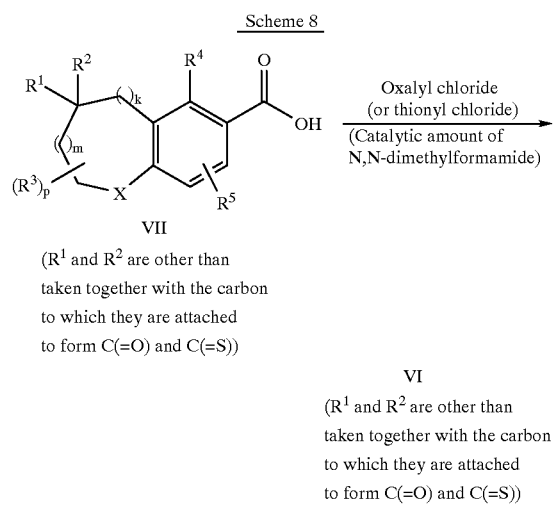

Scheme 9 illustrates the preparation of acids of Formula VII ($R^1$ and $R^2$ are other than taken together with the carbon to which they are attached to form C(=O) and C(=S); X=S(O)$_n$, and n=1 or 2) whereby an acid of Formula VII ($R^1$ and $R^2$ are other than taken together with the carbon to which they are attached to form C(=O) and C(=S); X=S) is reacted with a oxidizing reagent such as peroxyacetic acid, m-chloroperoxybenzoic acid, potassium peroxymonosulfate or hydrogen peroxide. The reaction may be buffered with a base such as sodium acetate or sodium carbonate. The oxidation is carried out by general methods known in the art (see for example, B. M. Trost, et al., *J. Org. Chem.* (1988), 53, 532; B. M. Trost, et al., *Tetrahedron Lett.* (1981), 21, 1287; S. Patai, et al., *The Chemistry of Sulphones and Sulphoxides*, John Wiley & Sons).

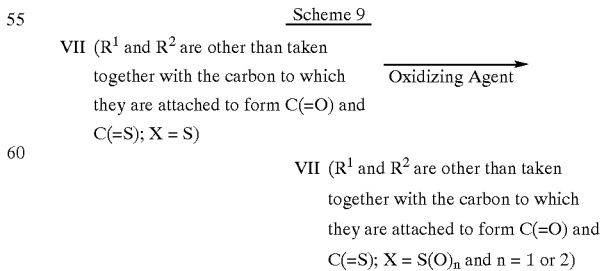

Scheme 10 illustrates the preparation of acids of Formula VII ($R^1$ and $R^2$ are other than taken together with the carbon to which they are attached to form C(=O) and C(=S), and X is S, O or $NR^{13}$) whereby a phenyl bromide of Formula VIII, ($R^1$ and $R^2$ are other than taken together with the carbon to which they are attached to form C(=O) and C(=S) and X is S, O or $NR^{13}$) is treated with n-butyllithium (or magnesium), and the lithium salt (or the Grignard reagent) generated in situ is then reacted with carbon dioxide followed by acidification with an acid such as hydrochloric acid. This conversion is carried out by general methods known in the art; see for example, M. A. Ogliaruso et al., *Synthesis of Carboxylic Acids, Esters and Their Derivatives*, pp 27–28, John Wiley & Sons; A. J. Bridges, et al., *J. Org. Chem.* (1990), 55 (2), 773; C. Franke, et al., *Angew. Chem. Int. Ed.* (1969), 8, 68. In some instances, the incorporation of protection/deprotection sequences or functional group interconversions into the synthesis will aid in obtaining the desired products. The use and choice of the protecting groups will be apparent to one skilled in chemical synthesis (see, for example, Green, T. W.; Wuts, P. G. M., Protective Groups in Organic Synthesis, 2nd ed.; Wiley: New York, 1991).

Scheme 10

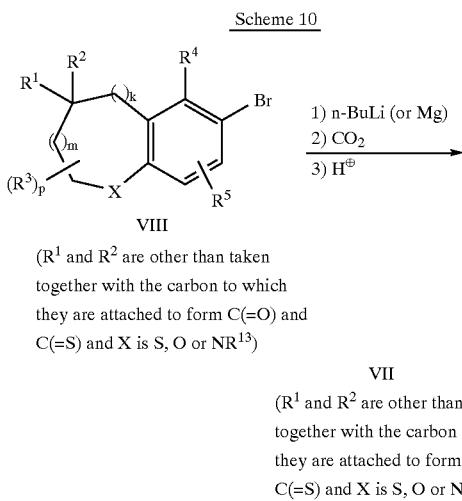

VIII
($R^1$ and $R^2$ are other than taken together with the carbon to which they are attached to form C(=O) and C(=S) and X is S, O or $NR^{13}$)

1) n-BuLi (or Mg)
2) $CO_2$
3) $H^⊕$

VII
($R^1$ and $R^2$ are other than taken together with the carbon to which they are attached to form C(=O) and C(=S) and X is S, O or $NR^{13}$)

Scheme 11 illustrates the preparation of phenyl bromides of Formula VIII ($R^1$ and $R^2$ are independently $C_1$-$C_6$ alkoxy, $C_1$-$C_6$ haloalkoxy, $C_1$-$C_6$ alkylthio or $C_1$-$C_6$ haloalkylthio; or $R^1$ and $R^2$ are taken together to form —$X^1$—$(CH_2)_r$—$X^2$— optionally substituted with at least one member selected from 1–8 halogen, 1–8 $CH_3$ and one $C_1$-$C_3$ alkoxy; $X^1$ and $X^2$ are as defined in the summary of the invention and X is S, O or $NR^{13}$) whereby a ketone of Formula IX (X is S, O or $NR^{13}$) is reacted with an alcohol, an alkylthiol, or $HX^1$—$(CH_2)_r$—$X^2H$ (optionally substituted with at least one member selected from 1–8 $CH_3$ and one $C_1$-$C_3$ alkoxy; $X^1$, $X^2$ and r are as defined in the summary of the invention) in the presence of a protic acid catalyst such as p-toluenesulfonic acid (or a Lewis acid such as $BF_3$) in an inert organic solvent such as toluene or in an alcohol (if the alcohol is the reagent). This conversion is carried out by general methods known in the art; see for example, T. W. Greene, et al., *Protective Groups in Organic Synthesis* (Second Edition), pp 175–221, John Wiley & Sons, Inc.

Scheme 11

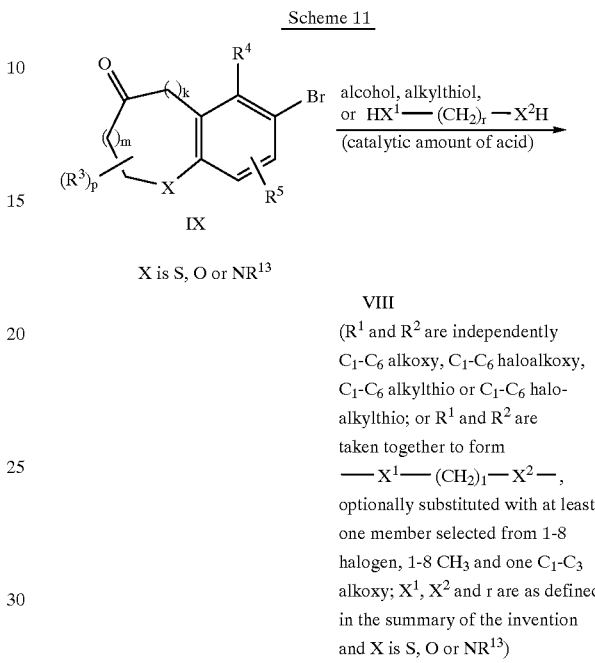

X is S, O or $NR^{13}$

VIII
($R^1$ and $R^2$ are independently $C_1$-$C_6$ alkoxy, $C_1$-$C_6$ haloalkoxy, $C_1$-$C_6$ alkylthio or $C_1$-$C_6$ haloalkylthio; or $R^1$ and $R^2$ are taken together to form
—$X^1$—$(CH_2)_1$—$X^2$—,
optionally substituted with at least one member selected from 1-8 halogen, 1-8 $CH_3$ and one $C_1$-$C_3$ alkoxy; $X^1$, $X^2$ and r are as defined in the summary of the invention and X is S, O or $NR^{13}$)

Scheme 12 illustrates the preparation of phenyl bromides of Formula VIII ($R^1$ and $R^2$ are taken together to form —$(CH_2)_s$—O—, —$(CH_2)_t$—$X^3$—$CH_2$—, —$(CH_2)_v$—$X^3$—$CH_2CH_2$— or —$(CH_2)_w$—, each group optionally substituted with at least one member selected from 1–8 halogen, 1–8 $CH_3$ and one $C_1$–$C_3$ alkoxy; and X is S, O or $NR^{13}$) where a ketone of Formula IX (X is S, O or $NR^{13}$) is reacted with a Grignard reagent, a sulfonium cycloalkylide, a lithium lithioalkoxide, an organopalladium reagent, a sulfonium ylide or other equivalent reagent in an inert organic solvent. Some of the immediate products from the reactions of Scheme 12 may be further modified to give the desired phenyl bromides of Formula VIII. The above-mentioned reactions are carried out by methods known in the art (or by slight modification of these methods): for example, see S. Umio, et al., *J. Med. Chem.* (1972), 15, p 855; B. Mudryk, et al., *J. Org. Chem.* (1989), 54 (24), p 5657; Z. Paryzek, et al., *Can. J. Chem.* (1987), 65 (1), p 229; B. M. Trost, et al., *J. Am. Chem. Soc.* (1972), 94, p 4777; B. M. Trost, et al., *J. Am. Chem. Soc.* (1985), 107, p 1778; S. Fukuzawa, et al., *J. Chem. Soc. Chem. Comm.* (1986), 8, p 624; J. F. Gil, et al., *Tetrahedron* (1994), 50 (11), p 3437; T. J. Jenkins, et al., *J. Org. Chem.* (1994), 59 (6), p 1485; C. J. Li, et al., *Organometallics* (1991), 10 (8), p 2548; E. J. Corey, et al., *J. Am. Chem. Soc.* (1965), 87, p 1353; K. Okuma, et al., *J. Org. Chem.* (1983), 48, 5133.

Scheme 12

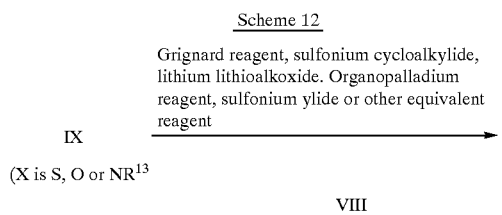

Grignard reagent, sulfonium cycloalkylide, lithium lithioalkoxide. Organopalladium reagent, sulfonium ylide or other equivalent reagent

IX (X is S, O or NR$^{13}$)

VIII ($R_1$ and $R_2$ are taken together to form —(CH$_2$)$_s$—O—, —(CH$_2$)$_t$—X$^3$—CH$_2$—, —(CH$_2$)$_v$—X$^3$—CH$_2$CH$_2$— or —(CH$_2$)$_w$—, each group optionally substituted with at least one member selected from 1-8 halogen, 1-8 CH$_3$ and one C$_1$-C$_3$ alkoxy; and X is S, O or NR$^{13}$).

Scheme 13 illustrates the preparation of phenyl bromides of Formula VIII (R$^1$ and R$^2$ are taken together to form —(CH$_2$)$_s$—S— optionally substituted with at least one member selected from 1–8 halogen, 1–8 CH$_3$ and one C$_1$–C$_3$ alkoxy; X is S, O or NR$^{13}$) whereby a thioketone of Formula X (X is S, O or NR$^{13}$) is reacted with a dibromo alkane of Formula XI in the presence of an equimolar amount or more of Yb metal in an inert organic solvent such as a mixture of benzene and hexamethylphosphoric triamide. This conversion is carried out by general methods known in the art; see for example, Y. Makioka, et al., *Chem. Lett.* (1994), 611.

Scheme 13

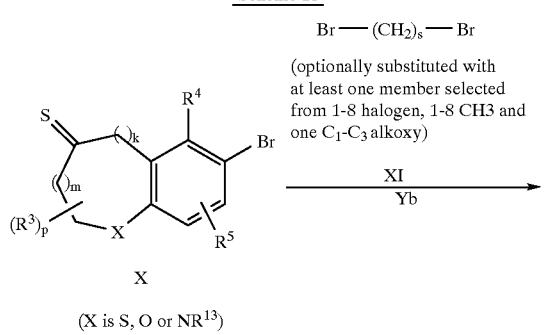

Br—(CH$_2$)$_s$—Br (optionally substituted with at least one member selected from 1-8 halogen, 1-8 CH3 and one C$_1$-C$_3$ alkoxy)

XI
Yb
→

X (X is S, O or NR$^{13}$)

VIII (R$^1$ and R$^2$ are taken together to form —(CH$_2$)$_s$—S—, optionally substituted with at least one member selected from 1-8 halogen, 1-8 CH$_3$ and one C$_1$-C$_3$ alkoxy and X is S, O or NR$^{13}$).

Some compounds of Formula VIII (k is 0; R$^1$ and R$^2$ are taken together to form —(CH$_2$)$_s$—X$^3$—, —(CH$_2$)$_t$—X$^3$—CH$_2$—, —(CH$_2$)$_v$—X$^3$—CH$_2$CH$_2$—, or —(CH$_2$)$_w$—, each group optionally substituted with at least one member selected from 1–8 halogen, 1–8 CH$_3$ and one C$_1$-C$_3$ alkoxy) can also be prepared by reacting an unsaturated alkylthiophenylbromide of Formula XII with a Lewis acid such as SnCl$_4$ or AlCl$_3$ or an acid such as trifluoroacetic acid or polyphosphoric acid in an inert organic solvent such as CH$_2$Cl$_2$ at temperature between 0° C. and 110° C. for a period of time ranging from 30 minutes to 3 days (Scheme 14). This conversion is carried out by general methods known in the art: see for example, M. J. Dawson, et al., *J. Med., Chem.* (1984), 27 (11), p 1516; H. G. Viehe, et al., *J. Chem. Soc., Chem. Commun.* (1995), (10), p 993.

Scheme 14

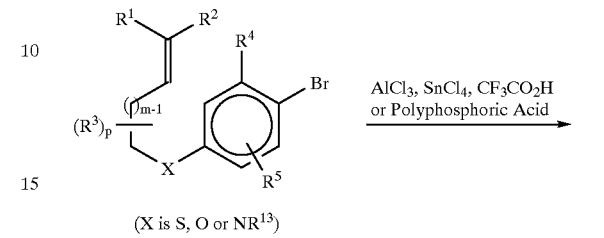

AlCl$_3$, SnCl$_4$, CF$_3$CO$_2$H or Polyphosphoric Acid
→

(X is S, O or NR$^{13}$)

XII

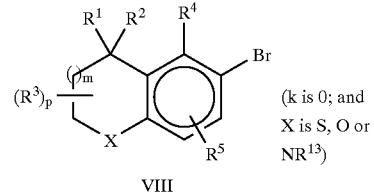

(k is 0; and X is S, O or NR$^{13}$)

VIII (R$_1$ and R$_2$ are taken together to form —(CH$_2$)$_s$—X$^3$—, —(CH$_2$)$_t$—X$^3$—CH$_2$—, —(CH$_2$)$_v$—X$^3$—CH$_2$CH$_2$— or —(CH$_2$)$_w$—, each group optionally substituted with at least one member selected from 1-8 halogen, 1-8 CH$_3$ and one C$_1$-C$_3$ alkoxy; and X is S, O or NR$^{13}$).

Some compounds of Formula VIII (k is 0; R$^1$ and R$^2$are taken together to form —(CH$_2$)$_s$—X$^3$—, —(CH$_2$)$_t$—X$^3$—CH$_2$—, —(CH$_2$)$_v$—X$^3$—CH$_2$—CH$_2$—, or —(CH$_2$)$_w$—, each group optionally substituted with at least one member selected from 1–8 halogen, 1–8 CH$_3$ and one C$_1$-C$_3$ alkoxy; and X is S, O or NR$^{13}$) can also be prepared by reacting a chloroalkylthiophenyl bromide of Formula XIII (X is S, O or NR$^{13}$) with a compound of Formula XIV in the presence of a Lewis acid such as SnCl$_4$, EtAlCl$_2$ or AlCl$_3$ in an inert organic solvent such as CH$_2$Cl$_2$ at temperature between 0° C. to 110° C. for a period of time ranging from 15 minutes to 3 days (Scheme 15). This conversion is carried out by general method known in the art: see for example, Y. Tamura, et al., *Tet. Lett.* (1981), p 3773; H. Ishibashi, et al., *J. Chem. Soc. Chem. Commun.* (1988), (12), p 827.

Scheme 15

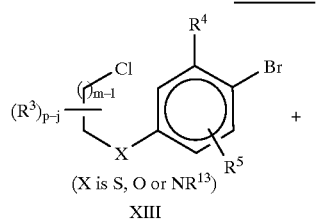

+

(X is S, O or NR$^{13}$)

XIII

-continued

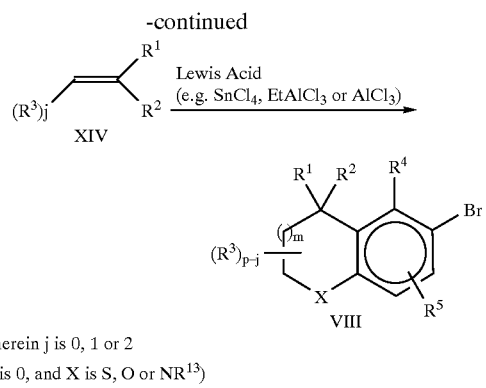

wherein j is 0, 1 or 2

(k is 0, and X is S, O or $NR^{13}$)

Scheme 16 illustrates the preparation of phenyl bromides of Formula VIII (k is 0; $R^1$ and $R^2$ are taken together to form —$CH_2CH_2$—, optionally substituted with at least one member selected from 1–4 halogen, 1–4 $CH_3$ and one $C_1$–$C_3$ alkoxy; or $R^1$ and $R^2$ are taken together to form —O—N($C_1$–$C_3$ alkyl)—$CHR^{12}$—$CH_2$— or —O—N=$CHR^{12}$—$CH_2$—, each group optionally substituted with at least one member selected from 1–2 halogen and 1–2 $CH_3$; and X is S, O or $NR^{13}$) where an alkene of Formula XV (X is S, O or $NR^{13}$) is reacted with a Wittig reagent, a nitrone, a silyl nitronate, a nitrile oxide, or a Simmons-Smith reagent in an inert organic solvent. Some of the immediate products from the reactions of Scheme 16 may be further modified to give the desired phenylbromides of Formula VIII. The above mentioned reactions are carried out by methods known in the art (or by slight modification of these methods): for example, see R. Mechoulam, et al., *J. Am. Chem. Soc.* (1958), 80, p 4386; A. Hosomi, et al., *Chem. Lett.* (1985), (7), p 1049. S. Mzengeza, et al., *J. Chem. Soc. Chem. Commun.* (1984), 9, p 606; H. Mitsu, et al., *Tet. Lett.* (1983), 24 (10), p 1049; J. E. Baldwin, et al., *J. Chem. Soc. Chem. Commun.* (1968), p 373; S. L. Ioffe, et al., *J. Gen. Chem. USSR* (Engl. Transl.) (1973), 43, p 1699; A. Brandi, et al., *Tet. Lett.* (1987), 28 (33), p 3845; D. P. Curran, et al., *J. Org. Chem* (1984), 49 (19), p 3474; R. J. Rawson, et al., *J. Org. Chem.*, (1970), 35 (6), p 2057.

Scheme 16

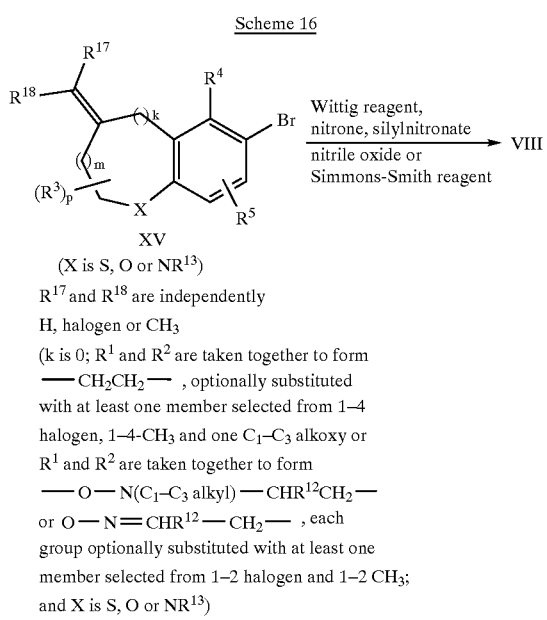

(X is S, O or $NR^{13}$)

$R^{17}$ and $R^{18}$ are independently

H, halogen or $CH_3$ (k is 0; $R^1$ and $R^2$ are taken together to form

—$CH_2CH_2$—, optionally substituted with at least one member selected from 1–4 halogen, 1–4-$CH_3$ and one $C_1$–$C_3$ alkoxy or $R^1$ and $R^2$ are taken together to form —O—N($C_1$–$C_3$ alkyl)—$CHR^{12}CH_2$— or O—N=$CHR^{12}$—$CH_2$—, each group optionally substituted with at least one member selected from 1–2 halogen and 1–2 $CH_3$;

and X is S, O or $NR^{13}$)

Some compounds of Formula VIII (X is S, O or $NR^{13}$) can also be prepared by reacting a substituted benzene of Formula XVI (X is S, O or $NR^{13}$) with bromine in an inert organic solvent (Scheme 17). This bromination is carried out by general methods known in the art. See E. Campaigne, et al., *J. Heterocycl. Chem.* (1969), 6, p 517; H. Gilman, *J. Am. Chem. Soc.* (1955), 77, p 6059.

Scheme 17

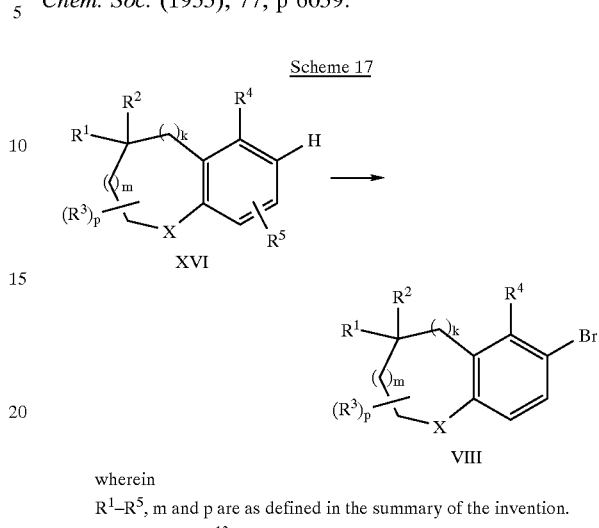

wherein $R^1$–$R^5$, m and p are as defined in the summary of the invention.

X is S, O or $NR^{13}$

The ketones of Formula IX can be prepared by general methods known in the art (or by slight modification of these methods); see, for example, W. Flemming, et al., *Chem. Ber.* (1925), 58, 1612; I. W. J. Still, et al., *Can. J. Chem.* (1976), 54, 453–470; V. J. Traynelis, et al., *J. Org. Chem.* (1961), 26, 2728; I. Nasuno, et al., WO 94/08988; F. Camps, et al., *J. Heterocycl. Chem.* (1985), 22(5), p. 1421; T. S. Rao, et al., *Indian J. Chem. B.* (1985), 24(11), p. 1159; S. Ghosh, et al., *Tetrahedron* (1989), 45(5), p. 1441; A. Danan, et al., *Synthesis-Stuttgart* (1991), (10), p. 879; P. Magnus, et al., *J. Chem. Soc. Chem. Comm.* (1991), (7), p. 544; A. Padwa, et al., *J. Org. Chem.* (1989), 54(12), p. 2862; S. A. Ali, et al., *J. Org. Chem.* (1979), 44, p. 4213; J. Blake, et al., *J. Am. Chem. Soc.* (1966), 88, p. 4061; M. Mori, et al., *J. Chem. Soc. Chem. Comm.* (1990), (18), p. 1222; S. Kano, et al., *J. Chem. Soc., Perkin. Trans.* 1 (1980), p. 2105; A. F. Bekhli, et al., *Khim Geterotsikl. Soedin.* (1975), p. 1118; W. S. Johnson, et al., *J. Am. Chem. Soc.* (1949), 71, p. 1901; J. A. Hirsch, et al., *J. Org. Chem.* (1974), 39(14), p. 2044; F. G. Mann, et al., *J. Chem. Soc.* (1957), p. 4166; A. C. Jain, et al., *Indian. J. Chem. B* (1987), 26(2), p. 136; G. Ariamala, et al., *Tet. Lett.* (1988), 29(28), p. 3487; B. Loubinoux, et al., *Tet. Lett.* (1992), 33(16), p. 2145; S. Cabiddu, et al., *J. Organomet. Chem.* (1989), 366(1–2), p. 1; R. HasenKamp, et al., *Chem. Ber.* (1980), 113, p. 1708; D. A. Pulman, et al., *J. Chem. Soc. Perkin. Trans.* 1 (1973), p. 410; W. C. Lumma, et al., *J. Org. Chem.* (1969), 34, p. 1566; P. D. Clark, et al., *Can. J. Chem.* (1982), 60(3), p. 243.

The thioketones of Formula X can be prepared from the ketones of Formula IX by general methods known in the art: see for example, V. K. Lusis, et al., *Khim. Geterotsiklt.* (1986), (5), p 709; T. A. Chibisova, et al., *Zh. Org. Khim.* (1986), 22 (9), p 2019. Compounds of Formula XI can be prepared by general methods known in the art (or by slight modifications of these methods): see W. Adams, et al., *Chem. Ber.* (1982), 115, p 2592; M. J. Dawson, et al., *J. Med. Chem.* (1984), 27 (11), p 1516. Compounds of Formula XII can be prepared by methods known in the art (or by slight modifications of these methods): see H. Ishibashi, et al., *J. Chem. Soc. Chem. Commun.* (1988), (12), p 827, L. Brandsma, et al., *Synthesis* (1978), p 577. Compounds of Formula XIV can be prepared from the ketones of Formula IX by general methods known in the art: see for examples: J. Hibino, et al., *Tet. Lett.* (1985), 26 (45), p 5579; A. S. Rao, *Synthetic Commun.* (1989), 19 (5–6), p 931–942; R. G. Gentles, et al., *J. Chem. Soc. Perk. Trans.* 1. (1991), (6), p 1423; F. A. Davis, *Tet. Lett.* (1991), 32 (52), p 7671.

Compounds of Formula XVI can be prepared from the de-bromo analogs of compounds of Formulae IX, X, XII, XIII and XV by one skilled in the art by using the reactions and techniques described in Schemes 12–15. The dicarbonyl compounds of Formula V are either commercially available or can be prepared by general methods known in the art (or by slight modification of these methods): for example, see D. Cartwright, et al., EP 0283261-B1; J. Dangelo, et al., *Tet. Lett.* (1991), 32(26), p. 3063; T. Okado, et al., *J Org. Chem.* (1977), 42, p. 1163; B. E. Maryanoff, et al., *J. Am. Chem Soc.* (1975), 97, p. 2718; E. Er, et al., *Helv. Chim. Acta.* (1992), 75(7), p. 2265; Y. D. Vankar, et al., *Tet. Lett.*, (1987), 28(5), p. 551; C. S. Pak, et al., *Tet. Lett.* (1991), 32(42), p. 601 1; I. Nishiguchi, et al., *Chem. Lett.* (198 1), p. 551; B. Eistert, et al., *Liebigs Ann. Chem.* (1962), 659, p. 64; N. K. Hamer, *Tet. Lett.* (1986), 27(19), p. 2167; M. Sato, et al., *Heterocycles* (1987), 26(10), p. 2611; A. Murray, et al., *Tet. Lett.* (1995), 36(2), p. 291; K. S. Kochhar, et al., *Tet. Lett.* (1984), 25(18), p. 1871; M. Sato, et al., *Tetrahedron* (1991), 47(30), p. 5689; M. Sato, et al., *Chem. Pharm. Bull.* (1990), 38(1), p. 94; T. Meal, U.S. Pat. No. 4,931,570; T. Muel, et al., U.S. Pat. No. 5,093,503.

Compounds of General Formula Ib can be readily prepared by one skilled in the art by using the reactions and techniques described in Schemes 18–21 of this section as well as by following the specific procedures given in Examples 2 and 4. The definitions of k, m, p, $R^1$–$R^5$, $R^8$–$R^{10}$ and X are as described in the Summary of the Invention.

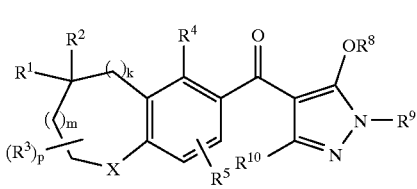

Ib

Scheme 18 illustrates the preparation of compounds of Formula Ib ($R^1$ and $R^2$ are other than taken together with the carbon to which they are attached to form C(=O) and C(=S), and $R^8$=$R^{8a}$ where $R^{8a}$ is the same as $R^8$ as described in the Summary of the Invention but not H) whereby a compound of Formula Ib ($R^1$ and $R^2$ are other than taken together with the carbon to which they are attached to form C(=O) and C(=S), and $R^8$=H) is reacted with a reagent of Formula XVII in the presence of a base wherein $X^5$ is chlorine, bromine, fluorine, trifluoromethanesulfonate, or acetate and $R^{8a}$ is as previously defined. This coupling is carried out by general methods known in the art; see for example, K. Nakamura, et al., WO 95/04054.

Scheme 18

Ib ($R^1$ and $R^2$ are other than taken together with the carbon to which they are attatched to form C(=O) and C(=S), $R^8$=H) + $R^{8a}X^5$ XVII →

Ib ($R^1$ and $R^2$ are other than taken together with the carbon to which they are attached to form C(=O) and C(=S), $R^8$=$R^{8a}$)

Scheme 19 illustrates the preparation of compounds of Formula Ib ($R^1$ and $R^2$ are other than taken together with the carbon to which they are attached to form C(=O) and C(=S), and $R^8$=H) whereby an ester of Formula XVIII ($R^1$ and $R^2$ are other than taken together with the carbon to which they are attached to form C(=O) and C(=S)) is reacted with a base such as triethylamine in the presence of a catalytic amount of cyanide source (e.g., acetone cyanohydrin or potassium cyanide). This rearrangement is carried out by methods known in the art; see for example, W. J. Michaely, EP 0369803-A1.

Scheme 19

XVIII
($R^1$ and $R^2$ are other than taken together with the carbon to which they are attached to form C(=O) and C(=S))

↓ base (e.g., triethylamine) and cyanide source in catalytic amount (e.g., acetone cyanohydrin or potassium cyanide)

Ib ($R^1$ and $R^2$ are other than taken together with the carbon to which they are attached to form C(=O) and C(=S), $R^8$=H)

Scheme 20 illustrates the preparation of compounds of Formula Ib ($R^1$ and $R^2$ are taken together with the carbon to which they are attached to form C(=O)) whereby a compound of Formula Ib ($R^1$ and $R^2$ are independently $C_1$–$C_6$ alkoxy or $R^1$ and $R^2$ are taken together to form —O—$(CH_2)_r$—O—) is stirred in a hydrochloric acid or hydrobromic acid aqueous solution (0.1 N to 12 N) at temperatures between 0° C. and 100° C. for a period of time ranging from 30 minutes to 3 days. This conversion is carried out by methods known in the art (or by slight modification of these methods): for example; see P. A. Grieco, et al., *J. Am. Chem. Soc.* (1977), 99, p 5773; P. A. Grieco, et al, *J. Am. Chem. Soc.* (1978), 43, p 4178.

Scheme 20

Ib
($R^1$ and $R^2$ are independently $C_1$–$C_6$ alkoxy or $R^1$ and $R^2$ are taken together to form —O—($CH_2$)$_r$O—)

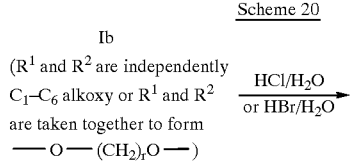

Ib
($R^1$ and $R^2$ are taken together with the carbon to which they are attached to form (C=O))

Esters of Formula XVIII ($R^1$ and $R^2$ are other than taken together with the carbon to which they are attached to form C(=O) and C(=S)) can be prepared by reacting a hydroxypyrazole of Formula XIX with an acid chloride of Formula VI ($R^1$ and $R^2$ are other than taken together with the carbon to which they are attached to form C(=O) and C(=S)) in the presence of a slight molar excess of a base such as triethylamine in an inert organic solvent such as acetonitrile, dichloromethane or toluene at temperatures between 0° C. and 110° C. (Scheme 21). This type of coupling is carried out by methods known in the art; see for example, W. J. Michaely, EP 0369803-A1.

Scheme 21

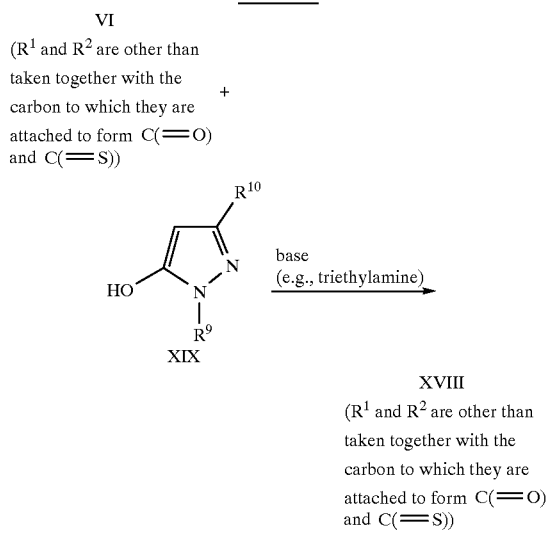

Compounds of General Formula Ic can be readily prepared from compounds of General Formulae Ia ($R^1$ and $R^2$ are taken together with the carbon to which they are attached to form C(=O)) or Ib ($R^1$ and $R^2$ are taken together with the carbon to which they are attached to form C(=O)) by treatment with $P_4S_{10}$ or Lawesson's reagent (see Scheme 22). This conversion is carried out by general methods known in the art (or slight modification of these methods): for example, see V. K. Lusis, et al., *Khim. Geterotsiklt.* (1986), 5, p 709; T. A. Chibisova, et al., *Zh. Org. Khim.* (1986), 22 (9), p 2019. The protection/deprotection of some functional Groups of starting materials of General Formula Ia ($R^1$ and $R^2$ are taken together with the carbon to which they are attached to form C(=O)) or Ib ($R^1$ and $R^2$ are taken together with the carbon to which they are attached to form C(=O)) may be necessary. The use and choice of the protecting groups will be apparent to one skilled in chemical synthesis (see, for example, T. W. Greene, et al., *Protective Groups in Organic Synthesis,* 2nd ed.; Wiley: New York, 1991).

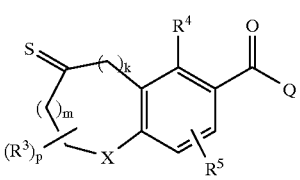

wherein
the definitions of k, m, p,
$R^3$—$R^5$, Q and X are as described
in the Summary of the invention Scheme 22

Ia or Ib  $\xrightarrow{P_4S_{10} \text{ or Lawesson's reagent}}$  Ic ($R^1$ and $R^2$ are taken
together with the carbon
to which they are attched
to form C=O)

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula I. One skilled in the art will also recognize that it may be necessary to perform a combination of the steps illustrated in the above schemes in an order other than that implied by the particular sequence presented to prepare the compounds of Formula I.

One skilled in the art will also recognize that compounds of Formula I and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. The abbreviation "dec" indicates that the compound appeared to decompose on melting. $^1$H NMR spectra are reported in ppm downfield from tetramethylsilane; s=singlet, d=doublet, t=triplet, q=quartet, m=multiplet, br s=broad singlet.

EXAMPLE 1

Step A: Preparation of 3-[(4-bromophenyl)thio]propanoic acid

8.5 g (0.211 mol) of sodium hydroxide was added to 45 mL of water, 20.0 g (0.106 mol) of 4-bromothiophenol (purchased from Aldrich Chemical Company) was then added and the mixture was cooled to about 0° C. 18.0 g (0.116 mol) of 3-bromopropionic acid (purchased from Aldrich Chemical Company) was added in portions while keeping the temperature below 5° C. The mixture was warmed to room temperature, stirred for 1 h under nitrogen, and was then washed with diethyl ether (3×100 mL). The aqueous layer was acidified with 1N HCl, and then filtered to yield 27.95 g of the title compound of Step A as a solid melting at 101–103° C. $^1$H NMR (CDCl$_3$): $\delta$2.66 (t,2H), 3.14 (t,2H), 7.2 (m,2H), 7.4 (m,2H).

Step B: Preparation of 6-bromo-2,3-dihydro-4H-1-benzothiopyran4-one

200 mL of concentrated sulfuric acid was added to 27.7 g (0.106 mol) of the title compound of Step A. The mixture was stirred at room temperature under nitrogen overnight, and was then poured over crushed ice. The mixture was filtered, and the solid was dissolved in methylene chloride. The resulting solution was dried (MgSO$_4$), filtered, and evaporated to dryness to yield 14.77 g of the title compound of Step B as a solid melting at 50° C. (dec). $^1$H NMR (CDCl$_3$): $\delta$3.0 (m,2H), 3.2 (m,2H), 7.16–8.2 (3H).

Step C: Preparation of 6-bromo-2,3-dihydrospiro[4H-1-benzothiopyran-4,2'-[1,3]dioxolane]

14.7 g (0.060 mol) of the title compound of Step B, 11 mL (0.19 mol) of ethylene glycol (purchased from Aldrich Chemical Company), and 0.4 g (2.10 mmol) of p-toluenesulfonic acid monohydrate (purchased from Aldrich Chemical Company) were added to 125 mL of toluene. The solution was stirred at reflux under nitrogen overnight, and was then washed with 1M sodium carbonate (2×250 mL), followed by water (2×250 mL). The organic layer was dried (Na$_2$SO$_4$), filtered, and evaporated to dryness to yield 13.58 g of the title compound of Step C as an oil. $^1$H NMR (CDCl$_3$): $\delta$2.2 (m,2H), 3.16 (m,2H), 4.1 (m,2H), 4.2 (m,2H), 7.0–7.6 (3H).

Step D: Preparation of 2,3-dihydrospiro[4H-1-benzothiopyran-4,2'[1,3]dioxolane]-6-carboxylic acid

13.58 g (0.047 mol) of the title compound of Step C was added to 150 mL of tetrahydrofuran. The solution was cooled to about –65° C. and 23 mL (0.057 mol) of 2.5 M n-butyllithium in hexane (purchased from Aldrich Chemical Company) was added dropwise while keeping the temperature below –55° C. After stirring under nitrogen for 1 h, excess solid CO$_2$ was added in one portion, and the mixture was stirred overnight while warming to room temperature. 100 mL of hexane was added to the mixture, and it was then filtered. To the solid residue was added 500 mL of water and 400 mL of methylene chloride. The solution was cooled to about 0° C., acidified to pH 1 with concentrated hydrochloric acid, and extracted with methylene chloride (3×400 mL). The resulting solution was dried (MgSO$_4$), filtered, and evaporated to dryness to yield 8.58 g of the title compound of Step D as a solid melting at 186.7° C. (dec). $^1$H NMR (Me$_2$SO-d$_6$): $\delta$2.2 (m,2H), 3.2 (m,2H), 4.1 (m,4H), 7.2–8.0 (3H), 12.8 (br s,1H).

Step E: Preparation of 2,3-dihydrospiro[4H-1-benzothiopyran-4,2'-[1,3]dioxolane]-6-carboxylic acid 1,1-dioxide

8.5 g (0.034 mol) of the title compound of Step D and 41.5 g (0.51 mol) of sodium acetate were added to 160 mL of methanol. The suspension was cooled to about 0° C., and a solution of 35.2 g (0.057 mol) of OXONE® (potassium peroxymonosulfate, purchased from Aldrich Chemical Company) in 160 mL of water was added dropwise while keeping the temperature below 6° C. The mixture was warmed to room temperature and stirred under nitrogen overnight. The mixture was diluted with 100 mL of water, cooled to about 0° C., acidified to pH 2 with concentrated hydrochloric acid, and extracted with chloroform (3×200 mL). The combined organic layers were dried (MgSO$_4$), filtered, and evaporated to dryness. The crude product was triturated with a hexane:diethyl ether mixture (9:1) to yield 6.98 g of the title compound of Step E as a solid melting at 208° C. (dec). $^1$H NMR (Me$_2$SO-d$_6$): $\delta$2.6 (m,2H), 3.7 (m,2H), 4.1–4.2 (m,4H), 7.9–8.15 (3H), 13.6 (br s,1H).

Step F: Preparation of 3-oxo-1-cyclohexen-1-yl 2,3-dihydrospiro[4H-1-benzothiopyran-4,2'-[1,3]dioxolane]-6-carboxylate 1,1-dioxide

2.0 g (7.0 mmol) of the title compound of Step E, 1.2 mL (0.014 mol) of oxalyl chloride (purchase from Janssen), and 2 drops of N,N-dimethylformamide were added to 50 mL of methylene chloride. The mixture was refluxed under nitrogen for 2 h, and was then evaporated to dryness. 50 mL of methylene chloride was added to the residue and the resulting mixture was evaporated to dryness. Another 50 mL of methylene chloride was added to the residue, and the solution was cooled to about 0° C. 0.86 g (7.7 mmol) of 1,3-cyclohexanedione (purchased from Aldrich Chemical Company) was added followed by 2.7 mL (0.0196 mol) of triethylamine, and the mixture was stirred overnight while warming to room temperature. The mixture was evaporated to dryness, the residue was stirred in 100 mL of water and filtered. The crude product was washed with hexane to yield 2.19 g of the title compound of Step F as a solid melting at 185–186° C. $^1$H NMR (CDCl$_3$): $\delta$2.2 (m,2H), 2.5 (t,2H), 2.7 (t,4H), 3.7 (m,2H), 4.2 (m,2H), 4.3 (m,2H), 6.0 (s,1H), 8.0–8.25 (3H).

Step G: Preparation of 2-[(2,3-dihydrospiro[4H-1-benzothiopyran-4,2'-[1,3]dioxolan]-6-yl)carbonyl]-1,3-cyclohexanedione S,S-dioxide

2.1 g (0.0056 mol) of the title compound of Step F, 4 drops of acetone cyanohydrin (purchased from Aldrich Chemical Company), and 1.36 mL (0.0097 mol) of triethylamine were added to 50 mL of acetonitrile and allowed to stir for 3 days at room temperature under nitrogen. The mixture was evaporated to dryness and 25 mL of water was added to the residue. The resulting mixture was acidified to pH 1 with concentrated hydrochloric acid, and filtered. The crude product was dissolved in methylene chloride and the resulting solution was dried (MgSO$_4$), filtered, and evaporated to dryness to yield 1.5 g of the title compound of Step G, a compound of the invention, as a solid melting at 131° C. (dec). $^1$H NMR (CDCl$_3$): $\delta$2.1 (m,2H), 2.6 (m,6H), 3.6 (m,2H), 4.1 (m,2H), 4.2 (m,2H), 7.6–7.9 (3H).

EXAMPLE 2

Step A: Preparation of 1-ethyl-1H-pyrazol-5-yl 2,3-dihydrospiro[4H-1-benzothiopyran-4,2'-[1,3]dioxolane]-6-carboxylate 1,1-dioxide

1.38 g (4.9 mmol) of the title compound of Step E in Example 1, 0.85 mL (0.0097 mol) of oxalyl chloride (purchased from Janssen), and 2 drops of N,N-dimethylformamide were added to 50 mL of methylene chloride. The mixture was refluxed under nitrogen for 2 h and was then evaporated to dryness. 50 mL of methylene chloride was added to the residue and the resulting mixture was evaporated to dryness. Another 50 mL of methylene chloride was added to the residue, and the solution was cooled to about 0° C. 0.60 g (5.4 mmol) of 1-ethyl-1H- pyrazol-5-ol was added followed by 1.9 mL (0.0136 mol) of triethylamine, and the mixture was stirred overnight while warming to room temperature. The mixture was evaporated to dryness, the residue was stirred in 100 mL of water and filtered. The crude product was washed with hexane to yield 1.45 g of the title compound of Step A as a solid melting at 158–160° C. $^1$H NMR (CDCl$_3$): δ1.4 (t,3H), 2.7 (m,2H), 3.7 (m,2H), 4.1–4.3 (m,6H), 6.2 (s,1H), 7.5–8.3 (4H).

Step B: Preparation of (2,3-dihydrospiro[4H-1-benzothiopyran-4,2'-[1,3]dioxolan]-6-yl)(1-ethyl-5-hydroxy-1H-pyrazol-4-yl)methanone S,S-dioxide 1.43 g (0.0038 mol) of the title compound of Step A, 4 drops of acetone cyanohydrin (purchased from Aldrich Chemical Company), and 0.92 mL (0.0066 mol) of triethylamine were added to 50 mL of acetonitrile and the resulting mixture was allowed to stir at room temperature under nitrogen overnight. The mixture was evaporated to dryness and 25 mL of water was added to the residue. The resulting mixture was acidified to pH 1 with concentrated hydrochloric acid and the crude product was filtered off. The crude product was washed with hexane and dissolved in methylene chloride. The resulting solution was dried (MgSO$_4$), filtered, and evaporated to dryness to yield 0.44 g of the title compound of Step B, a compound of the invention, as an oil. $^1$H NMR (CDCl$_3$): δ1.46 (t,3H), 2.7 (m,2H), 3.7 (m,2H), 4.1 (q,2H), 4.2–4.3 (m,4H), 7.7–8.0 (4H).

EXAMPLE 3

Step A: Preparation of 3-[2,5-(dichlorophenyl)thio]propanoic acid 44.68 g (1.12 mol) of sodium hydroxide was added to 240 mL of water, 100 g (0.56 mol) of 2,5-dichlorobenzenethiol (purchased from Aldrich Chemical Company) was then added and the mixture was cooled to 10° C. 93.98 g (0.62 mol) of 3-bromopropionic acid (purchased from Aldrich Chemical Company) was added in portions while keeping the temperature below 25° C. The mixture was warmed to room temperature, stirred for 2 h under nitrogen, and was then washed with diethyl ether (3×400 mL). The aqueous layer was acidified with 1N HCl and filtered. The residue was dissolved in 2 L of methylene chloride and 50 mL of methanol. The resulting solution was dried (MgSO$_4$), filtered, and evaporated to dryness to yield 126.34 g of the title compound of Step A as a solid melting at 99° C. (dec). $^1$H NMR (CDCl$_3$): δ2.75 (t,2H), 3.2 (t,2H), 7.1–7.3 (3H).

Step B: Preparation of 5,8-dichloro-2,3-dihydro-4H-1-benzothiopyran-4-one 63 g (0.25 mol) of the title compound of Step A and 25.6 mL (0.351 mol) of thionyl chloride were added to 225 mL of chloroform and the mixture was refluxed under nitrogen for 2 h. The mixture was then concentrated, the resulting residue was dissolved in 75 mL of carbon disulfide and the resulting solution was added dropwise to a cooled (0° C.) solution of 46.8 g (0.351 mol) of aluminum chloride in 200 mL of carbon disulfide while keeping the temperature below 5° C. The mixture was refluxed under nitrogen for 1 h, and then stirred for 2 days at 35° C. The reaction mixture was poured into 300 g of crushed ice containing 150 mL of concentrated hydrochloric acid and the resulting mixture was extracted with chloroform (3×200 mL). The combined organic layers were washed with 10% sodium hydroxide (2×150 mL), water (2×150 mL), dried (MgSO$_4$), filtered, and evaporated to dryness to yield 45.18 g of the title compound of Step B as a solid melting at 66–68° C. $^1$H NMR (CDCl$_3$): δ3.0 (m,2H), 3.3 (m,2H), 7.1–7.35 (2H).

Step C: Preparation of 6-bromo-5,8-dichloro-2,3-dihydro-4H-1-benzothiopyran-4-one A solution of 45.18 g (0.19 mol) of the title compound of Step B in 400 mL of methylene chloride was added dropwise at room temperature under nitrogen to a mixture of 64.6 g (0.48 mol) of aluminum chloride in 400 mL of methylene chloride. After stirring for 15 min, 10.5 mL (0.20 mol) of bromine was added dropwise and the mixture was refluxed for 10 min. The mixture, while still warm, was poured into 550 g of ice containing 110 mL of concentrated hydrochloric acid, and the resulting mixture was extracted with diethyl ether (2×500 mL). The combined organic layers were dried (Na$_2$SO$_4$), filtered, and evaporated to dryness to yield 57.37 g of the title compound of Step C as a solid melting at 89–90° C. $^1$H NMR (CDCl$_3$): δ3.0 (m,2H), 3.3 (m,2H), 7.7 (s,1H).

Step D: Preparation of 6-bromo-5,8-dichloro-2,3-dihydrospiro[4H-1-benzothiopyran-4,2'-[1,3]dioxolane]

15 g (0.048 mol) of the title compound of Step C, 150 mL of ethylene glycol, 100 mL of trimethyl orthoformate (purchased from Aldrich Chemical Company), and 0.06 g of p-toluenesulfonic acid monohydrate were stirred together at 80° C. under nitrogen overnight. The mixture was diluted with 250 mL of diethyl ether and washed with a 1:1 mixture of 1N sodium hydroxide:saturated aqueous NaCl (2×300 mL), saturated aqueous NaCl (1×500 mL), dried (Na$_2$SO$_4$), filtered, and evaporated to dryness. The crude product was chromatographed over silica gel eluting with a mixture of ethyl acetate:hexane (0.5:9.5) to yield 8.39 g of the title compound of Step D as a solid melting at 152–153° C. $^1$H NMR (CDCl$_3$): δ2.3 (m,2H), 3.0 (m,2H), 4.16 (m,2H), 4.37 (m,2H), 7.6 (s,1H).

Step E: Preparation of 5,8-dichloro-2,3-dihydrospiro[4H-1-benzothiopyran-4,2'-[1,3]dioxolane]-6-carboxylic acid 8.3 g (0.023 mol) of the title compound of Step D was added to 150 mL of tetrahydrofuran. The solution was cooled to about –65° C. under nitrogen and 11.2 mL (0.028 mol) of 2.5M n-butyllithium in hexane was added dropwise while keeping the temperature below –55° C. After stirring for 30 min, carbon dioxide was bubbled into the mixture for 1 h. The mixture was allowed to warm to room temperature, 150 mL of hexanes were added, and the mixture was filtered. The solid was added to water, and the resulting mixture was acidified to pH 1 with concentrated hydrochloric acid and then extracted with methylene chloride (3×100 mL). The combined extracts were dried (MgSO$_4$), filtered, and evaporated to dryness to yield 5.03 g of the title compound of Step E as an oil. $^1$H NMR (CDCl$_3$): δ2.3 (m,2H), 3.0 (m,2H), 4.16 (m,2H), 4.38 (m,2H), 7.7 and 7.8 (2s,1H). NMR showed the presence of about 50 mol % tetrahydrofuran remaining in the oil.

Step F: Preparation of 5,8-dichloro-2,3-dihydrospiro[4H-1-benzothiopyran-4,2'-[1,3]dioxolane]-6-carboxylic acid 1,1-dioxide 5.03 g (0.0157 mol) of the title compound of Step E and 1.93 g (0.024 mol) of sodium acetate were added to 75 mL of methanol. The solution was cooled to about 0° C. and a solution of 16.41 g (0.0267 mol) of OXONE® (purchased from Aldrich Chemical Company) in 75 mL of water was added dropwise while keeping the temperature below 6° C. The mixture was warmed to room temperature and stirred under nitrogen overnight. The mixture was diluted with 50 mL of water, cooled to about 0° C., acidified to pH 1 with concentrated hydrochloric acid, and extracted with chloroform (3×150 mL). The combined organic layers were dried (MgSO$_4$), filtered, and evaporated to dryness to yield 3.59 g of the title compound of Step F as a solid melting at 165° C. (dec). $^1$H NMR (Me$_2$SO-d$_6$): δ2.6 (m, 2H), 3.7 (m,2H), 4.18 (m,2H), 4.3 (m,2H), 8.0 (s,1H).

Step G: Preparation of 3-oxo-1-cyclohexen-1-yl 5,8-dichloro-2,3-dihydrospiro[4H-1-benzothiopyran-4,2'-[1,3]dioxolane]-6-carboxylate 1,1-dioxide 1.75 g (4.97 mmol) of the title compound of Step F, 1.30 mL (0.015 mol) of oxalyl chloride (purchased from Janssen), and 2 drops of N,N-dimethylformamide were added to 50 mL of methylene chloride. The mixture was refluxed under nitrogen for 2 h and was then evaporated to dryness. 50 mL of methylene chloride was added to the residue and the resulting mixture was evaporated to dryness. Another 50 mL of methylene chloride was added to the residue, and the solution was cooled to about 0° C. 0.61 g (5.5 mmol) of 1,3-cyclohexanedione (purchased from Aldrich Chemical Company) was added followed by 2.15 mL (0.0154 mol) of triethylamine, and the mixture was stirred over 2 days while warming to room temperature. The mixture was evaporated to dryness and the crude product was chromatographed over silica gel eluting with a mixture of ethyl acetate:hexane (6:4) to yield 0.62 g of the title compound of Step G as a solid melting at 168° C. (dec). $^1$H NMR (CDCl$_3$): $\delta$2.1 (m,2H), 2.5 (t,2H), 2.7 (t,4H), 3.6 (m,2H), 4.2 (m,2H), 4.4 (m,2H), 6.1 (s,1H), 7.8 (s,1H).

Step H: Preparation of 2-[(5,8-dichloro-2,3-dihydrospiro[4H-1-benzothiopyran-4,2'-[1,3]dioxolan]-6-yl)carbonyl]-1,3-cyclohexanedione S,S-dioxide 0.60g (1.3 mmol) of the title compound of Step G, 1 drop of acetone cyanohydrin (purchased from Aldrich Chemical Company), and 0.33 mL (2.4 mmol) of triethylamine were added to 50 mL of acetonitrile and the mixture was allowed to stir overnight at room temperature under nitrogen. About 0.06 g of potassium cyanide was added to the mixture and the mixture was stirred for 2 h. The mixture was then evaporated to dryness and water was added to the residue. The aqueous mixture was acidified to pH 1 with concentrated hydrochloric acid and filtered to yield 0.40 g of the title compound of Step H, a compound of the invention, as a solid melting at 140° C. (dec). $^1$H NMR (CDCl$_3$): $\delta$2.0 (m,2H), 2.6 (m,6H), 3.6 (m,2H), 4.1 (m,2H), 4.35 (m,2H), 7.2 (I H). NMR showed the presence of about 33 mol % triethylamine remaining in the solid.

EXAMPLE 4

Step A: Preparation of 3-[(2,5-dimethylphenyl)thio]propanoic acid 43.4 g (1.086 mol) of sodium hydroxide was added to 230 mL of water, 75.0 g (0.543 mol) of 2,5-dimethylthiophenol (purchased from Aldrich Chemical Company) was then added and the mixture was cooled to about 10° C. 91.30 g (0.597 mol) of 3-bromopropionic acid (purchased from Aldrich Chemical Company) was added in portions while keeping the temperature below 25° C. The mixture was warmed to room temperature, stirred for 2 h under nitrogen, and was then washed with diethyl ether (3×500 mL). The aqueous layer was acidified with 1N HCl and filtered to yield 112.79 g of the title compound of Step A as a solid melting at 97–98° C. $^1$H NMR (CDCl$_3$): $\delta$2.3 (s,3H), 2.34 (s,3H), 2.68 (t,2H), 3.1 (t,2H), 6.9 (d,1H), 7.06–7.14 (2H).

Step B: Preparation of 2,3-dihydro-5,8-dimethyl4H-1-benzopyran-4-one 530 mL of concentrated sulfuric acid was added to 24.91 g (0.1 19 mol) of the title compound of Step A while being cooled with an acetone/ice bath. The ice bath was removed, the mixture was stirred for 1 h and was then poured over crushed ice. The aqueous mixture was extracted with a 1:9 mixture of diethyl ether:hexane (6×500 mL), dried (MgSO$_4$), filtered, and evaporated to dryness to yield 11.75 g of the title compound of Step B as an oil. $^1$H NMR (CDCl$_3$): 6 2.3 (s,3H), 2.6 (s,3H), 2.97 (m,2H), 3.2 (m,2H), 6.9–7.1 (2H).

Step C: Preparation of 6-bromo-2,3-dihydro-5,8-dimethyl-4H-1-benzothiopyran-4-one A solution of 4.07 g (0.021 mol) of the title compound of Step B in 25 mL of methylene chloride was added dropwise to a mixture of 7.07 g (0.053 mol) of aluminum chloride (purchased from Aldrich Chemical Company) and 25 mL of methylene chloride. The suspension was stirred for approximately 15 minutes, 1.14 mL (0.022 mol) of bromine (purchased from Janssen) was added dropwise, and the mixture was refluxed for 10 minutes. The warm mixture was poured into 10 mL of concentrated hydrochloric acid containing 75 g of ice, stirred for 10 minutes, diluted with 50 mL of water, and then extracted with diethyl ether (2×200 mL). The combined organic layers were washed with water (2×200 mL), dried (Na$_2$SO$_4$), filtered, and evaporated to dryness. The crude product was chromatographed over silica gel eluting with a mixture of ethyl acetate:hexane (5%:95%) to yield 2.62 g of the title compound of Step C as a solid melting at 87–88° C. $^1$H NMR (CDCl$_3$): $\delta$2.3 (s,3H), 2.6 (s,3H), 3.0 (m,2H), 3.2 (m,2H), 7.45 (s,1H).

Step D: Preparation of 6-bromo-2,3-dihydro-5,8-dimethylspiro[4H-1-benzothiopyran-4,2'-[1,3]dioxolane]

26.06 g (0.096 mol) of the title compound of Step C, 250 mL of ethylene glycol, 170 mL of trimethyl orthoformate (purchased from Aldrich Chemical Company), and 0.06 g of p-toluenesulfonic acid monohydrate were stirred together at 80° C. under nitrogen overnight. The mixture was diluted with 400 mL of diethyl ether. The resulting mixture was washed with a 1:1 mixture of 1N sodium hydroxide:saturated aqueous NaCl (2×600 mL) and then with saturated aqueous NaCl (1×600 mL). The organic layer was dried (Na$_2$SO$_4$), filtered, and evaporated to dryness. The crude product was chromatographed over silica gel eluting with a mixture of ethyl acetate:hexane (1:9) to yield 24.73 g of the title compound of Step D as a solid melting at 97° C. (dec). $^1$H NMR (CDCl$_3$): $\delta$2.2 (s,3H), 2.3 (m,2H), 2.4 (s,3H), 3.0 (m,2H), 4.15 (m,2H), 4.3 (m,2H), 7.3 (s,1H).

Step E: Preparation of 2,3-dihydro-5,8-dimethylspiro[4H-1-benzothiopyran-4,2'-[1,3]dioxolane]-6-carboxylic acid 24.73 g (0.078 mol) of the title compound of Step D was added to 150 mL of tetrahydrofuran. The solution was cooled to about −70° under nitrogen and 37.68 mL (0.094 mol) of 2.5M n-butyllithium in hexane was added dropwise while keeping the temperature below −65° C. After stirring for 1 h, carbon dioxide was bubbled into the mixture for 2 h. The mixture was allowed to warm to room temperature, 300 mL of hexanes were added, and the resulting mixture was filtered. The resulting solid was added to a mixture of water:methylene chloride (400 mL:400 mL), cooled to about 0° C., and acidified to pH 1 with concentrated hydrochloric acid. The layers were separated and the aqueous layer was extracted with diethyl ether (2×300 mL). The combined organic layers were dried (MgSO$_4$), filtered, and evaporated to dryness to yield 4.73 g of the title compound of Step E as a solid melting at 207–208° C. $^1$H NMR (Me$_2$SO-d$_6$): $\delta$2.2 (m,5H), 2.4 (s,3H), 3.0 (m,2H), 4.1–4.2 (m,4H), 7.4 (s,1H).

Step F: Preparation of 2,3-dihydro-5,8-dimethylspiro[4H-1-benzothiopyran-4,2'-[1,3]dioxolane]-6-carboxylic acid 1,1-dioxide 4.73 g (0.017 mol) of the title compound of Step E and 2.08 g (0.025 mol) of sodium acetate were added to 85 mL of methanol. The solution was cooled to about 0° C., and a solution of 17.66 g (0.029 mol) of OXONE® (purchased from Aldrich Chemical Company) in 85 mL of water was added dropwise while keeping the temperature below 6° C. The mixture was warmed to room temperature and stirred under nitrogen overnight. The mixture was diluted with 50 mL of water, cooled to about 0° C., acidified to around pH 2 with concentrated hydrochloric acid, and then extracted with chloroform (3×150 mL). The combined organic layers were dried (MgSO$_4$), filtered, and evaporated to dryness. The residue was triturated in diethyl ether:hexane (1:9) which was decanted to yield 4.18 g of the title compound of Step F as a solid melting at 185° C. (dec). $^1$H NMR (Me$_2$SO-d$_6$): δ2.35 (s,3H), 2.5 (m,2H), 2.6 (s,3H), 3.5 (m,2H), 4.16 (m,2H), 4.2 (m,2H), 7.6 (s,1H).

Step G: Preparation of 1-ethyl-1H-pyrazol-5-yl 2,3-dihydro-5,8-dimethylspiro[4H-1-benzothiopyran-4,2'-[1,3]dioxolane]-6-carboxylate 1,1-dioxide 1.18 g (3.8 mmol) of the title compound of Step F, 0.99 mL (0.011 mol) of oxalyl chloride (purchased from Janssen), and 2 drops of N,N-dimethylformamide were added to 50 mL of methylene chloride. The mixture was refluxed under nitrogen for 2 h, and was then evaporated to dryness. 50 mL of methylene chloride was added to the residue and the resulting mixture was evaporated to dryness. Another 50 mL of methylene chloride was added to the residue, and the solution was cooled to about 0° C. 0.51 g (4.5 mmol) of 1-ethyl-1H-pyrazol-5-ol was added followed by 1.63 mL (0.012 mol) of triethylamine, and the mixture was stirred overnight while warming to room temperature. The mixture was evaporated to dryness and the crude product was chromatographed eluting with a mixture of ethyl acetate:hexane (6:4) to yield 0.24 g of the title compound of Step G as a semi-solid. $^1$H NMR (CDCl$_3$): δ1.4 (t,3H), 2.5 (s,3H), 2.6 (m,2H), 2.8 (s,3H), 3.5 (m,2H), 4.1–4.4 (m,6H), 6.26 (s,1H), 7.5–7.7 (2H).

Step H: Preparation of (2,3-dihydro-5,8-dimethylspiro[4H-1-benzothiopyran-4,2 -[1,3]dioxolan]-6-yl)(1-ethyl-5-hydroxy-1H-pyrazol-4-yl)methanone S,S-dioxide 0.24 g (0.59 mmol) of the title compound of Step G, 0.25 drops of acetone cyanohydrin (purchased from Aldrich Chemical Company), and 0.14 mL (1.0 mmol) of triethylamine were added to 25 mL of acetonitrile and the mixture was allowed to stir at room temperature under nitrogen for 1.5 h. About 0.06 g of potassium cyanide was added to the mixture which then was stirred at room temperature overnight. The mixture was evaporated to dryness and water was added to the residue. The resulting mixture was acidified to pH 1 with concentrated hydrochloric acid and extracted with methylene chloride (2×50 mL). The combined organic layers were dried (MgSO$_4$), filtered, and evaporated to dryness to yield 0.17 g of the title compound of Step H, a compound of the invention, as a solid melting at 111° C. (dec). $^1$H NMR (CDCl$_3$): δ1.46 (t,3H), 2.3 (s,3H), 2.6 (m,2H), 2.8 (s,3H), 3.5 (m,2H), 4.1 (q,2H), 4.2–4.3 (m,4H), 7.3 (2H).

EXAMPLE 5

Step A: Preparation of 3-oxo-1-cyclohexen-1-yl 2,3-dihydro-5,8-dimethylspiro[4H-1-benzothiopyran-4,2'-[1,3]dioxolane]-6-carboxylate 1,1-dioxide 3.0 g (9.6 mmol) of the title compound of Step F in Example 4, 2.5 mL (0.029 mol) of oxalyl chloride (purchased from Janssen), and 2 drops of N,N-dimethylformamide were added to 100 mL of methylene chloride. The mixture was refluxed under nitrogen for 2 h, and was then evaporated to dryness. 100 mL of methylene chloride was added to the residue and evaporated to dryness. Another 100 mL of methylene chloride was added to the residue, and the solution was cooled to about 0° C. 1.19 g (0.0106 mol) of 1,3-cyclohexanedione (purchased from Aldrich Chemical Company) was added followed by 4.15 mL (0.030 mol) of triethylamine, and the mixture was stirred overnight while warming to room temperature. The mixture was evaporated to dryness and the crude product was chromatographed over silica gel eluting with a mixture of ethyl acetate:hexane (1:1) to yield 1.33 g of the title compound of Step A as a solid melting at 109–111° C. $^1$H NMR (CDCl$_3$): δ2.1 (m,2H), 2.5 (m,5H), 2.6 (m,2H), 2.7 (m,2H), 2.8 (s,3H), 3.5 (m,2H), 4.2 (m,2H), 4.3 (m,2H), 6.0 (s,1H), 7.7 (s,1H).

Step B: Preparation of 2-[(2,3-dihydro-5,8-dimethylspiro[4H-1-benzothiopyran-4,2'-[1,3]dioxolan]-6-yl)carbonyl]-1,3-cyclohexanedione S,S-dioxide 1.33 g (3.3 mmol) of the title compound of Step A, 1 drop of acetone cyanohydrin (purchased from Aldrich Chemical Company), and 0.80 mL (5.7 mmol) of triethylamine were added to 50 mL of acetonitrile and the mixture was allowed to stir for 1.5 h. About 0.06 g of potassium cyanide was added to the mixture which was then stirred overnight at room temperature under nitrogen. Another 0.03 g of potassium cyanide was added to the mixture which was then stirred for 3 h. The mixture was then evaporated to dryness, water was added to the residue, and the aqueous mixture was acidified to pH 1 with concentrated hydrochloric acid and filtered. The solid residue was dissolved in methylene chloride and the resulting solution was dried (MgSO$_4$), filtered, and evaporated to dryness to yield 1.09 g of the title compound of Step B, a compound of the invention, as a solid melting at 130° C. (dec.). $^1$H NMR (CDCl$_3$): δ2.0 (m,2H), 2.2 (s,3H), 2.6 (m,6H), 2.7 (s,3H), 3.5 (m,2H), 4.14 (m,2H), 4.26 (m,2H), 6.9 (1H).

EXAMPLE 6

Step A: Preparation of 6-bromo-2,3-dihydro-5,8-dimethylspiro[4H-1-benzothiopyran-4,2'-[1,3]dithiolane]

To a solution of the title compound of Step C in Example 4 (5.0 g, 18.4 mmol) in methylene chloride (50 mL) under a nitrogen atmosphere was added 1,2-ethanedithiol (Aldrich, 2.32 mL, 27.7 mmol) and boron trifluoride diethyl etherate (Janssen Chimica, 3.41 mL, 27.7 mmol). The resulting mixture was stirred overnight at room temperature. To this reaction mixture was added 1.0 N sodium hydroxide (5 mL) and saturated aqueous sodium chloride (50 mL). The resulting mixture was extracted three times with diethyl ether. The combined organic extracts were dried (MgSO$_4$), filtered, and concentrated under reduced pressure to dryness. The resulting residue was crystallized in 1-chlorobutane to give the title compound of Step A (4.0 g) as a solid melting at 141–143° C. $^1$H NMR (CDCl$_3$): δ2.19 (s,3H), 2.78 (m,2H), 2.80 (s,3H), 3.09 (m,2H), 3.45–3.70 (4H), 7.29 (s,1H).

Step B: Preparation of 2,3-dihydro-5,8-dimethylspiro[4H-1-benzothiopyran4,2'-[1,3]dithiolane]-6-carboxylic acid To a solution of the title compound of Step A (2.7 g, 7.7 mmol) in tetrahydrofuran (20 mL) under a nitrogen atmosphere cooled to –78° C. was added n-butyllithium (Aldrich, 4.6 mL, 11.5 mmol of a 2.5 M solution in hexane) dropwise while maintaining the temperature below –60° C. After stirring for 2 h, excess carbon dioxide (dry ice) was added. The resulting mixture was allowed to warm to room temperature and was left at room temperature overnight. To this reaction mixture was added hexanes (30 mL), and the mixture was filtered. The solid was added to a mixture of water:methylene chloride (20 mL:20 mL), cooled to about 0° C., and acidified to pH 1 with concentrated hydrochloric acid. The organic layer was separated, and aqueous layer was extracted with diethyl ether (3×25 mL). The combined organic layers were dried (MgSO$_4$), filtered, and concentrated under reduced pressure to about 10 mL. A white solid precipitated and this solid was isolated by filtration to afford the title compound of Step B (1.62 g) as a solid melting at 236–238° C. $^1$H NMR (Me$_2$SO-d$_6$): δ2.17 (s,3H), 2.68 (m,2H), 2.81 (s,3H), 3.11 (m,2H), 3.50–3.70 (4H), 7.33 (s,1H), 12.78 (s,1H).

Step C: Preparation of 3-oxo-1-cyclohexen-1-yl 2,3-dihydro-5,8-dimethylspiro[4H-1-benzothiopyran-4,2'-[1,3]dithiolane]-6-carboxylate To a solution of the title compound of Step B (0.77 g, 2.4 mmol) in methylene chloride (25 mL) under a nitrogen atmosphere was added oxalyl chloride (Aldrich, 0.63 mL, 7.2 mmol) and 1 drop of N,N-dimethylformamide. The resulting mixture was refluxed for 1.5 h and was then evaporated to dryness. To the resulting residue was added methylene chloride (25 mL) and the resulting mixture was evaporated to dryness. Another 25 mL of methylene chloride was added to the residue, and the solution was cooled to about 0° C. To this mixture was added 1,3-cyclohexanedione (Aldrich, 0.30 g, 2.6 mmol) followed by addition of triethylamine (1.0 mL, 7.2 mmol). The mixture was stirred overnight while warming to room temperature. To the reaction mixture was added saturated aqueous sodium chloride and the resulting mixture was extracted three times with diethyl ether. The combined organic extracts were dried (MgSO$_4$), filtered, and concentrated under reduced pressure to dryness. Chromatography of the crude product on silica gel with a mixture of hexanes:ethyl acetate (3:1) yielded the title compound of Step C (0.69 g) as a semi-solid. $^1$H NMR (CDCl$_3$): δ2.13 (m,2H), 2.26 (s,3H), 2.45 (t,2H), 2.66 (m,2H), 2.76 (m,2H), 2.95 (s,3H), 3.18 (m,2H), 3.50–3.70 (4H), 6.00 (s,1H), 7.50 (s,1H).

Step D: Preparation of 2-[(2,3-dihydro-5,8-dimethylspiro[4H-1-benzothiopyran-4,2'-[1,3]dithiolan]-6-yl)carbonyl]-3-hydroxy-2-cyclohexen-1-one To a solution of the title compound of Step C (0.67 g, 1.6 mmol) in acetonitrile (12 mL) under a nitrogen atmosphere was added acetone cyanohydrin (Aldrich, 2 drops), and triethylamine (0.40 mL, 2.8 mmol). The mixture was allowed to stir at room temperature overnight. About 5 mg of potassium cyanide was added to the reaction mixture. After stirring at room temperature for an additional 6 h, the mixture was heated at 50–55° C. for 10 h. The mixture was cooled to room temperature and then concentrated under reduced pressure to dryness. To the resulting residue was added water (20 mL), and the resulting aqueous mixture was acidified to pH 1 with concentrated hydrochloric acid. The solid from the mixture was separated by filtration to afford an 80:20 mixture (0.60 g) of the title compound of Step D and the title compound of Step B as a solid melting at 217–222° C. $^1$H NMR (CDCl$_3$) for the title compound of Step D: δ2.03 (m,2H), 2.20 (s,3H), 2.42 (t,2H), 2.66 (s,3H), 2.72–2.81 (4H), 3.16 (m,2H), 3.42–3.60 (4H), 6.71 (s,1H).

By the procedures described herein together with methods known in the art, the following compounds of Tables 1 to 9 can be prepared. The following abbreviations are used in the Tables which follow: n=normal, p=para, p-tolyl=4-methylphenyl, and NO$_2$=nitro.

TABLE 1

| $R^{3a}$ | $R^{3b}$ | $R^1$ | $R^2$ | $R^4$ | $R^5$ | $R^6$ | n | m |
|---|---|---|---|---|---|---|---|---|
| H | H | —OCH$_2$CH$_2$O— | | CH$_3$ | CH$_3$ | OH | 2 | 1 |
| H | H | —OCH$_2$CH$_2$O— | | CH$_3$ | H | OH | 2 | 1 |
| H | H | —OCH$_2$CH$_2$O— | | H | H | OH | 2 | 1 |
| H | H | —OCH$_2$CH$_2$O— | | Cl | Cl | OH | 2 | 1 |
| H | H | —OCH$_2$CH$_2$O— | | Cl | H | OH | 2 | 1 |
| H | H | —OCH$_2$CH$_2$O— | | Cl | CH$_3$ | OH | 2 | 1 |
| H | H | —OCH$_2$CH$_2$O— | | NO$_2$ | H | OH | 2 | 1 |
| CH$_3$ | CH$_3$ | —OCH$_2$CH$_2$O— | | CH$_3$ | CH$_3$ | OH | 2 | 1 |
| CH$_3$ | CH$_3$ | —OCH$_2$CH$_2$O— | | CH$_3$ | H | OH | 2 | 1 |
| CH$_3$ | CH$_3$ | —OCH$_2$CH$_2$O— | | H | H | OH | 2 | 1 |
| CH$_3$ | CH$_3$ | —OCH$_2$CH$_2$O— | | Cl | Cl | OH | 2 | 1 |
| CH$_3$ | CH$_3$ | —OCH$_2$CH$_2$O— | | Cl | H | OH | 2 | 1 |
| CH$_3$ | CH$_3$ | —OCH$_2$CH$_2$O— | | Cl | CH$_3$ | OH | 2 | 1 |
| CH$_3$ | H | —OCH$_2$CH$_2$O— | | CH$_3$ | CH$_3$ | OH | 2 | 1 |
| CH$_3$ | H | —OCH$_2$CH$_2$O— | | CH$_3$ | H | OH | 2 | 1 |
| CH$_3$ | H | —OCH$_2$CH$_2$O— | | H | H | OH | 2 | 1 |
| CH$_3$ | H | —OCH$_2$CH$_2$O— | | Cl | Cl | OH | 2 | 1 |
| CH$_3$ | H | —OCH$_2$CH$_2$O— | | Cl | H | OH | 2 | 1 |
| CH$_3$ | H | —OCH$_2$CH$_2$O— | | Cl | CH$_3$ | OH | 2 | 1 |
| H | H | —OCH$_2$CH(CH$_3$)O— | | CH$_3$ | CH$_3$ | OH | 2 | 1 |
| H | H | —OCH$_2$CH(CH$_3$)O— | | CH$_3$ | H | OH | 2 | 1 |
| H | H | —OCH$_2$CH(CH$_3$)O— | | H | H | OH | 2 | 1 |
| H | H | —OCH$_2$CH(CH$_3$)O— | | Cl | Cl | OH | 2 | 1 |
| H | H | —OCH$_2$CH(CH$_3$)O— | | Cl | H | OH | 2 | 1 |
| H | H | —OCH$_2$CH(CH$_3$)O— | | Cl | CH$_3$ | OH | 2 | 1 |
| CH$_3$ | CH$_3$ | —OCH$_2$CH(CH$_3$)O— | | CH$_3$ | CH$_3$ | OH | 2 | 1 |
| CH$_3$ | CH$_3$ | —OCH$_2$CH(CH$_3$)O— | | CH$_3$ | H | OH | 2 | 1 |
| CH$_3$ | CH$_3$ | —OCH$_2$CH(CH$_3$)O— | | H | H | OH | 2 | 1 |
| CH$_3$ | CH$_3$ | —OCH$_2$CH(CH$_3$)O— | | Cl | Cl | OH | 2 | 1 |
| CH$_3$ | CH$_3$ | —OCH$_2$CH(CH$_3$)O— | | Cl | H | OH | 2 | 1 |
| CH$_3$ | CH$_3$ | —OCH$_2$CH(CH$_3$)O— | | Cl | CH$_3$ | OH | 2 | 1 |
| CH$_3$ | H | —OCH$_2$CH(CH$_3$)O— | | CH$_3$ | CH$_3$ | OH | 2 | 1 |
| CH$_3$ | H | —OCH$_2$CH(CH$_3$)O— | | CH$_3$ | H | OH | 2 | 1 |
| CH$_3$ | H | —OCH$_2$CH(CH$_3$)O— | | H | H | OH | 2 | 1 |
| CH$_3$ | H | —OCH$_2$CH(CH$_3$)O— | | Cl | Cl | OH | 2 | 1 |
| CH$_3$ | H | —OCH$_2$CH(CH$_3$)O— | | Cl | H | OH | 2 | 1 |
| CH$_3$ | H | —OCH$_2$CH(CH$_3$)O— | | Cl | CH$_3$ | OH | 2 | 1 |
| H | H | —OCH$_2$CH$_2$CH$_2$O— | | CH$_3$ | CH$_3$ | OH | 2 | 1 |
| H | H | —OCH$_2$CH$_2$CH$_2$O— | | CH$_3$ | H | OH | 2 | 1 |
| H | H | —OCH$_2$CH$_2$CH$_2$O— | | H | H | OH | 2 | 1 |
| H | H | —OCH$_2$CH$_2$CH$_2$O— | | Cl | Cl | OH | 2 | 1 |
| H | H | —OCH$_2$CH$_2$CH$_2$O— | | Cl | H | OH | 2 | 1 |
| H | H | —OCH$_2$CH$_2$CH$_2$O— | | Cl | CH$_3$ | OH | 2 | 1 |
| CH$_3$ | CH$_3$ | —OCH$_2$CH$_2$CH$_2$O— | | CH$_3$ | CH$_3$ | OH | 2 | 1 |
| CH$_3$ | CH$_3$ | —OCH$_2$CH$_2$CH$_2$O— | | CH$_3$ | H | OH | 2 | 1 |
| CH$_3$ | CH$_3$ | —OCH$_2$CH$_2$CH$_2$O— | | H | H | OH | 2 | 1 |
| CH$_3$ | CH$_3$ | —OCH$_2$CH$_2$CH$_2$O— | | Cl | Cl | OH | 2 | 1 |
| CH$_3$ | CH$_3$ | —OCH$_2$CH$_2$CH$_2$O— | | Cl | H | OH | 2 | 1 |
| CH$_3$ | CH$_3$ | —OCH$_2$CH$_2$CH$_2$O— | | Cl | CH$_3$ | OH | 2 | 1 |
| CH$_3$ | H | —OCH$_2$CH$_2$CH$_2$O— | | CH$_3$ | CH$_3$ | OH | 2 | 1 |
| CH$_3$ | H | —OCH$_2$CH$_2$CH$_2$O— | | CH$_3$ | H | OH | 2 | 1 |
| CH$_3$ | H | —OCH$_2$CH$_2$CH$_2$O— | | H | H | OH | 2 | 1 |
| CH$_3$ | H | —OCH$_2$CH$_2$CH$_2$O— | | Cl | Cl | OH | 2 | 1 |
| CH$_3$ | H | —OCH$_2$CH$_2$CH$_2$O— | | Cl | H | OH | 2 | 1 |
| CH$_3$ | H | —OCH$_2$CH$_2$CH$_2$O— | | Cl | CH$_3$ | OH | 2 | 1 |
| H | H | CH$_3$O | CH$_3$O | CH$_3$ | CH$_3$ | OH | 2 | 1 |
| H | H | CH$_3$O | CH$_3$O | CH$_3$ | H | OH | 2 | 1 |
| H | H | CH$_3$O | CH$_3$O | H | H | OH | 2 | 1 |
| H | H | CH$_3$O | CH$_3$O | Cl | Cl | OH | 2 | 1 |
| H | H | CH$_3$O | CH$_3$O | Cl | H | OH | 2 | 1 |
| H | H | CH$_3$O | CH$_3$O | Cl | CH$_3$ | OH | 2 | 1 |
| CH$_3$ | CH$_3$ | CH$_3$O | CH$_3$O | CH$_3$ | CH$_3$ | OH | 2 | 1 |
| CH$_3$ | CH$_3$ | CH$_3$O | CH$_3$O | CH$_3$ | H | OH | 2 | 1 |
| CH$_3$ | CH$_3$ | CH$_3$O | CH$_3$O | H | H | OH | 2 | 1 |
| CH$_3$ | CH$_3$ | CH$_3$O | CH$_3$O | Cl | Cl | OH | 2 | 1 |
| CH$_3$ | CH$_3$ | CH$_3$O | CH$_3$O | Cl | H | OH | 2 | 1 |
| CH$_3$ | CH$_3$ | CH$_3$O | CH$_3$O | Cl | CH$_3$ | OH | 2 | 1 |
| CH$_3$ | H | CH$_3$O | CH$_3$O | CH$_3$ | CH$_3$ | OH | 2 | 1 |
| CH$_3$ | H | CH$_3$O | CH$_3$O | CH$_3$ | H | OH | 2 | 1 |
| CH$_3$ | H | CH$_3$O | CH$_3$O | H | H | OH | 2 | 1 |
| CH$_3$ | H | CH$_3$O | CH$_3$O | Cl | Cl | OH | 2 | 1 |

TABLE 1-continued

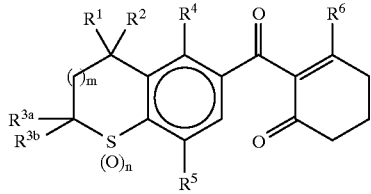
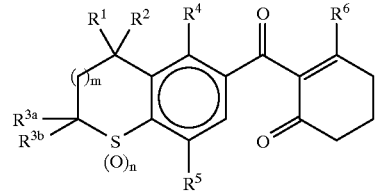

| R³ᵃ | R³ᵇ | R¹ | R² | R⁴ | R⁵ | R⁶ | n | m |
|---|---|---|---|---|---|---|---|---|
| CH₃ | H | CH₃O | CH₃O | Cl | H | OH | 2 | 1 |
| CH₃ | H | CH₃O | CH₃O | Cl | CH₃ | OH | 2 | 1 |
| H | H | H₅C₂O | H₅C₂O | CH₃ | CH₃ | OH | 2 | 1 |
| H | H | H₅C₂O | H₅C₂O | CH₃ | H | OH | 2 | 1 |
| H | H | H₅C₂O | H₅C₂O | H | H | OH | 2 | 1 |
| H | H | H₅C₂O | H₅C₂O | Cl | Cl | OH | 2 | 1 |
| H | H | H₅C₂O | H₅C₂O | Cl | H | OH | 2 | 1 |
| H | H | H₅C₂O | H₅C₂O | Cl | CH₃ | OH | 2 | 1 |
| CH₃ | CH₃ | H₅C₂O | H₅C₂O | CH₃ | CH₃ | OH | 2 | 1 |
| CH₃ | CH₃ | H₅C₂O | H₅C₂O | CH₃ | H | OH | 2 | 1 |
| CH₃ | CH₃ | H₅C₂O | H₅C₂O | H | H | OH | 2 | 1 |
| CH₃ | CH₃ | H₅C₂O | H₅C₂O | Cl | Cl | OH | 2 | 1 |
| CH₃ | CH₃ | H₅C₂O | H₅C₂O | Cl | H | OH | 2 | 1 |
| CH₃ | CH₃ | H₅C₂O | H₅C₂O | Cl | CH₃ | OH | 2 | 1 |
| CH₃ | H | H₅C₂O | H₅C₂O | CH₃ | CH₃ | OH | 2 | 1 |
| CH₃ | H | H₅C₂O | H₅C₂O | CH₃ | H | OH | 2 | 1 |
| CH₃ | H | H₅C₂O | H₅C₂O | H | H | OH | 2 | 1 |
| CH₃ | H | H₅C₂O | H₅C₂O | Cl | Cl | OH | 2 | 1 |
| CH₃ | H | H₅C₂O | H₅C₂O | Cl | H | OH | 2 | 1 |
| CH₃ | H | H₅C₂O | H₅C₂O | Cl | CH₃ | OH | 2 | 1 |
| H | H | —CH₂CH₂CH₂CH₂— | | CH₃ | CH₃ | OH | 2 | 1 |
| H | H | —CH₂CH₂CH₂CH₂— | | CH₃ | H | OH | 2 | 1 |
| H | H | —CH₂CH₂CH₂CH₂— | | H | H | OH | 2 | 1 |
| H | H | —CH₂CH₂CH₂CH₂— | | Cl | Cl | OH | 2 | 1 |
| H | H | —CH₂CH₂CH₂CH₂— | | Cl | H | OH | 2 | 1 |
| H | H | —CH₂CH₂CH₂CH₂— | | Cl | CH₃ | OH | 2 | 1 |
| CH₃ | CH₃ | —CH₂CH₂CH₂CH₂— | | CH₃ | CH₃ | OH | 2 | 1 |
| CH₃ | CH₃ | —CH₂CH₂CH₂CH₂— | | CH₃ | H | OH | 2 | 1 |
| CH₃ | CH₃ | —CH₂CH₂CH₂CH₂— | | H | H | OH | 2 | 1 |
| CH₃ | CH₃ | —CH₂CH₂CH₂CH₂— | | Cl | Cl | OH | 2 | 1 |
| CH₃ | CH₃ | —CH₂CH₂CH₂CH₂— | | Cl | H | OH | 2 | 1 |
| CH₃ | CH₃ | —CH₂CH₂CH₂CH₂— | | Cl | CH₃ | OH | 2 | 1 |
| CH₃ | H | —CH₂CH₂CH₂CH₂— | | CH₃ | CH₃ | OH | 2 | 1 |
| CH₃ | H | —CH₂CH₂CH₂CH₂— | | CH₃ | H | OH | 2 | 1 |
| CH₃ | H | —CH₂CH₂CH₂CH₂— | | H | H | OH | 2 | 1 |
| CH₃ | H | —CH₂CH₂CH₂CH₂— | | Cl | Cl | OH | 2 | 1 |
| CH₃ | H | —CH₂CH₂CH₂CH₂— | | Cl | H | OH | 2 | 1 |
| CH₃ | H | —CH₂CH₂CH₂CH₂— | | Cl | CH₃ | OH | 2 | 1 |
| H | H | —CH₂CH₂CH₂CH₂CH₂— | | CH₃ | CH₃ | OH | 2 | 1 |
| H | H | —CH₂CH₂CH₂CH₂CH₂— | | CH₃ | H | OH | 2 | 1 |
| H | H | —CH₂CH₂CH₂CH₂CH₂— | | H | H | OH | 2 | 1 |
| H | H | —CH₂CH₂CH₂CH₂CH₂— | | Cl | Cl | OH | 2 | 1 |
| H | H | —CH₂CH₂CH₂CH₂CH₂— | | Cl | H | OH | 2 | 1 |
| H | H | —CH₂CH₂CH₂CH₂CH₂— | | Cl | CH₃ | OH | 2 | 1 |
| CH₃ | CH₃ | —CH₂CH₂CH₂CH₂CH₂— | | CH₃ | CH₃ | OH | 2 | 1 |
| CH₃ | CH₃ | —CH₂CH₂CH₂CH₂CH₂— | | CH₃ | H | OH | 2 | 1 |
| CH₃ | CH₃ | —CH₂CH₂CH₂CH₂CH₂— | | H | H | OH | 2 | 1 |
| CH₃ | CH₃ | —CH₂CH₂CH₂CH₂CH₂— | | Cl | Cl | OH | 2 | 1 |
| CH₃ | CH₃ | —CH₂CH₂CH₂CH₂CH₂— | | Cl | H | OH | 2 | 1 |
| CH₃ | CH₃ | —CH₂CH₂CH₂CH₂CH₂— | | Cl | CH₃ | OH | 2 | 1 |
| CH₃ | H | —CH₂CH₂CH₂CH₂CH₂— | | CH₃ | CH₃ | OH | 2 | 1 |
| CH₃ | H | —CH₂CH₂CH₂CH₂CH₂— | | CH₃ | H | OH | 2 | 1 |
| CH₃ | H | —CH₂CH₂CH₂CH₂CH₂— | | H | H | OH | 2 | 1 |
| CH₃ | H | —CH₂CH₂CH₂CH₂CH₂— | | Cl | Cl | OH | 2 | 1 |
| CH₃ | H | —CH₂CH₂CH₂CH₂CH₂— | | Cl | H | OH | 2 | 1 |
| CH₃ | H | —CH₂CH₂CH₂CH₂CH₂— | | Cl | CH₃ | OH | 2 | 1 |
| H | H | —CH₂CH₂CH₂O— | | CH₃ | CH₃ | OH | 2 | 1 |
| H | H | —CH₂CH₂CH₂O— | | CH₃ | H | OH | 2 | 1 |
| H | H | —CH₂CH₂CH₂O— | | H | H | OH | 2 | 1 |
| H | H | —CH₂CH₂CH₂O— | | Cl | Cl | OH | 2 | 1 |
| H | H | —CH₂CH₂CH₂O— | | Cl | H | OH | 2 | 1 |
| H | H | —CH₂CH₂CH₂O— | | Cl | CH₃ | OH | 2 | 1 |
| CH₃ | CH₃ | —CH₂CH₂CH₂O— | | CH₃ | CH₃ | OH | 2 | 1 |
| CH₃ | CH₃ | —CH₂CH₂CH₂O— | | CH₃ | H | OH | 2 | 1 |
| CH₃ | CH₃ | —CH₂CH₂CH₂O— | | H | H | OH | 2 | 1 |
| CH₃ | CH₃ | —CH₂CH₂CH₂O— | | Cl | Cl | OH | 2 | 1 |
| CH₃ | CH₃ | —CH₂CH₂CH₂O— | | Cl | H | OH | 2 | 1 |
| CH₃ | CH₃ | —CH₂CH₂CH₂O— | | Cl | CH₃ | OH | 2 | 1 |
| CH₃ | H | —CH₂CH₂CH₂O— | | CH₃ | CH₃ | OH | 2 | 1 |
| CH₃ | H | —CH₂CH₂CH₂O— | | CH₃ | H | OH | 2 | 1 |
| CH₃ | H | —CH₂CH₂CH₂O— | | H | H | OH | 2 | 1 |
| CH₃ | H | —CH₂CH₂CH₂O— | | Cl | Cl | OH | 2 | 1 |
| CH₃ | H | —CH₂CH₂CH₂O— | | Cl | H | OH | 2 | 1 |
| CH₃ | H | —CH₂CH₂CH₂O— | | Cl | CH₃ | OH | 2 | 1 |
| H | H | —OCH₂CH₂O— | | CH₃ | CH₃ | OH | 2 | 0 |
| H | H | —OCH₂CH₂O— | | CH₃ | H | OH | 2 | 0 |
| H | H | —OCH₂CH₂O— | | H | H | OH | 2 | 0 |
| H | H | —OCH₂CH₂O— | | Cl | Cl | OH | 2 | 0 |
| H | H | —OCH₂CH₂O— | | Cl | H | OH | 2 | 0 |
| H | H | —OCH₂CH₂O— | | Cl | CH₃ | OH | 2 | 0 |
| CH₃ | CH₃ | —OCH₂CH₂O— | | CH₃ | CH₃ | OH | 2 | 0 |
| CH₃ | CH₃ | —OCH₂CH₂O— | | CH₃ | H | OH | 2 | 0 |
| CH₃ | CH₃ | —OCH₂CH₂O— | | H | H | OH | 2 | 0 |
| CH₃ | CH₃ | —OCH₂CH₂O— | | Cl | Cl | OH | 2 | 0 |
| CH₃ | CH₃ | —OCH₂CH₂O— | | Cl | H | OH | 2 | 0 |
| CH₃ | CH₃ | —OCH₂CH₂O— | | Cl | CH₃ | OH | 2 | 0 |
| CH₃ | H | —OCH₂CH₂O— | | CH₃ | CH₃ | OH | 2 | 0 |
| CH₃ | H | —OCH₂CH₂O— | | CH₃ | H | OH | 2 | 0 |
| CH₃ | H | —OCH₂CH₂O— | | H | H | OH | 2 | 0 |
| CH₃ | H | —OCH₂CH₂O— | | Cl | Cl | OH | 2 | 0 |
| CH₃ | H | —OCH₂CH₂O— | | Cl | H | OH | 2 | 0 |
| CH₃ | H | —OCH₂CH₂O— | | Cl | CH₃ | OH | 2 | 0 |
| H | H | —OCH₂CH(CH₃)O— | | CH₃ | CH₃ | OH | 2 | 0 |
| H | H | —OCH₂CH(CH₃)O— | | CH₃ | H | OH | 2 | 0 |
| H | H | —OCH₂CH(CH₃)O— | | H | H | OH | 2 | 0 |
| H | H | —OCH₂CH(CH₃)O— | | Cl | Cl | OH | 2 | 0 |
| H | H | —OCH₂CH(CH₃)O— | | Cl | H | OH | 2 | 0 |
| H | H | —OCH₂CH(CH₃)O— | | Cl | CH₃ | OH | 2 | 0 |
| CH₃ | CH₃ | —OCH₂CH(CH₃)O— | | CH₃ | CH₃ | OH | 2 | 0 |
| CH₃ | CH₃ | —OCH₂CH(CH₃)O— | | CH₃ | H | OH | 2 | 0 |
| CH₃ | CH₃ | —OCH₂CH(CH₃)O— | | H | H | OH | 2 | 0 |
| CH₃ | CH₃ | —OCH₂CH(CH₃)O— | | Cl | Cl | OH | 2 | 0 |
| CH₃ | CH₃ | —OCH₂CH(CH₃)O— | | Cl | H | OH | 2 | 0 |
| CH₃ | CH₃ | —OCH₂CH(CH₃)O— | | Cl | CH₃ | OH | 2 | 0 |
| CH₃ | H | —OCH₂CH(CH₃)O— | | CH₃ | CH₃ | OH | 2 | 0 |
| CH₃ | H | —OCH₂CH(CH₃)O— | | CH₃ | H | OH | 2 | 0 |
| CH₃ | H | —OCH₂CH(CH₃)O— | | H | H | OH | 2 | 0 |
| CH₃ | H | —OCH₂CH(CH₃)O— | | Cl | Cl | OH | 2 | 0 |
| CH₃ | H | —OCH₂CH(CH₃)O— | | Cl | H | OH | 2 | 0 |
| CH₃ | H | —OCH₂CH(CH₃)O— | | Cl | CH₃ | OH | 2 | 0 |
| H | H | —OCH₂CH₂CH₂O— | | CH₃ | CH₃ | OH | 2 | 0 |
| H | H | —OCH₂CH₂CH₂O— | | CH₃ | H | OH | 2 | 0 |
| H | H | —OCH₂CH₂CH₂O— | | H | H | OH | 2 | 0 |
| H | H | —OCH₂CH₂CH₂O— | | Cl | Cl | OH | 2 | 0 |
| H | H | —OCH₂CH₂CH₂O— | | Cl | H | OH | 2 | 0 |
| H | H | —OCH₂CH₂CH₂O— | | Cl | CH₃ | OH | 2 | 0 |
| CH₃ | CH₃ | —OCH₂CH₂CH₂O— | | CH₃ | CH₃ | OH | 2 | 0 |
| CH₃ | CH₃ | —OCH₂CH₂CH₂O— | | CH₃ | H | OH | 2 | 0 |
| CH₃ | CH₃ | —OCH₂CH₂CH₂O— | | H | H | OH | 2 | 0 |
| CH₃ | CH₃ | —OCH₂CH₂CH₂O— | | Cl | Cl | OH | 2 | 0 |
| CH₃ | CH₃ | —OCH₂CH₂CH₂O— | | Cl | H | OH | 2 | 0 |
| CH₃ | CH₃ | —OCH₂CH₂CH₂O— | | Cl | CH₃ | OH | 2 | 0 |
| CH₃ | H | —OCH₂CH₂CH₂O— | | CH₃ | CH₃ | OH | 2 | 0 |
| CH₃ | H | —OCH₂CH₂CH₂O— | | CH₃ | H | OH | 2 | 0 |
| CH₃ | H | —OCH₂CH₂CH₂O— | | H | H | OH | 2 | 0 |
| CH₃ | H | —OCH₂CH₂CH₂O— | | Cl | Cl | OH | 2 | 0 |
| CH₃ | H | —OCH₂CH₂CH₂O— | | Cl | H | OH | 2 | 0 |
| CH₃ | H | —OCH₂CH₂CH₂O— | | Cl | CH₃ | OH | 2 | 0 |
| H | H | —OCH₂CH₂O— | | CH₃ | CH₃ | OH | 2 | 2 |
| H | H | —OCH₂CH₂O— | | CH₃ | H | OH | 2 | 2 |
| H | H | —OCH₂CH₂O— | | H | H | OH | 2 | 2 |
| H | H | —OCH₂CH₂O— | | Cl | Cl | OH | 2 | 2 |

TABLE 1-continued

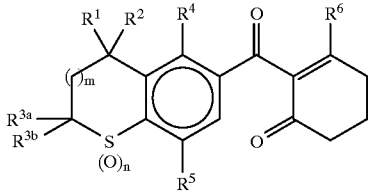
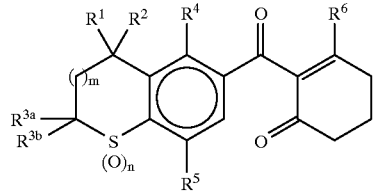

| R3a | R3b | R1 | R2 | R4 | R5 | R6 | n | m |
|---|---|---|---|---|---|---|---|---|
| H | H | —OCH$_2$CH$_2$O— | | Cl | H | OH | 2 | 2 |
| H | H | —OCH$_2$CH$_2$O— | | Cl | CH$_3$ | OH | 2 | 2 |
| CH$_3$ | CH$_3$ | —OCH$_2$CH$_2$O— | | CH$_3$ | CH$_3$ | OH | 2 | 2 |
| CH$_3$ | CH$_3$ | —OCH$_2$CH$_2$O— | | CH$_3$ | H | OH | 2 | 2 |
| CH$_3$ | CH$_3$ | —OCH$_2$CH$_2$O— | | H | H | OH | 2 | 2 |
| CH$_3$ | CH$_3$ | —OCH$_2$CH$_2$O— | | Cl | Cl | OH | 2 | 2 |
| CH$_3$ | CH$_3$ | —OCH$_2$CH$_2$O— | | Cl | H | OH | 2 | 2 |
| CH$_3$ | CH$_3$ | —OCH$_2$CH$_2$O— | | Cl | CH$_3$ | OH | 2 | 2 |
| CH$_3$ | H | —OCH$_2$CH$_2$O— | | CH$_3$ | CH$_3$ | OH | 2 | 2 |
| CH$_3$ | H | —OCH$_2$CH$_2$O— | | CH$_3$ | H | OH | 2 | 2 |
| CH$_3$ | H | —OCH$_2$CH$_2$O— | | H | H | OH | 2 | 2 |
| CH$_3$ | H | —OCH$_2$CH$_2$O— | | Cl | Cl | OH | 2 | 2 |
| CH$_3$ | H | —OCH$_2$CH$_2$O— | | Cl | H | OH | 2 | 2 |
| CH$_3$ | H | —OCH$_2$CH$_2$O— | | Cl | CH$_3$ | OH | 2 | 2 |
| H | H | —OCH$_2$CH(CH$_3$)O— | | CH$_3$ | CH$_3$ | OH | 2 | 2 |
| H | H | —OCH$_2$CH(CH$_3$)O— | | CH$_3$ | H | OH | 2 | 2 |
| H | H | —OCH$_2$CH(CH$_3$)O— | | H | H | OH | 2 | 2 |
| H | H | —OCH$_2$CH(CH$_3$)O— | | Cl | Cl | OH | 2 | 2 |
| H | H | —OCH$_2$CH(CH$_3$)O— | | Cl | H | OH | 2 | 2 |
| H | H | —OCH$_2$CH(CH$_3$)O— | | Cl | CH$_3$ | OH | 2 | 2 |
| CH$_3$ | CH$_3$ | —OCH$_2$CH(CH$_3$)O— | | CH$_3$ | CH$_3$ | OH | 2 | 2 |
| CH$_3$ | CH$_3$ | —OCH$_2$CH(CH$_3$)O— | | CH$_3$ | H | OH | 2 | 2 |
| CH$_3$ | CH$_3$ | —OCH$_2$CH(CH$_3$)O— | | H | H | OH | 2 | 2 |
| CH$_3$ | CH$_3$ | —OCH$_2$CH(CH$_3$)O— | | Cl | Cl | OH | 2 | 2 |
| CH$_3$ | CH$_3$ | —OCH$_2$CH(CH$_3$)O— | | Cl | H | OH | 2 | 2 |
| CH$_3$ | CH$_3$ | —OCH$_2$CH(CH$_3$)O— | | Cl | CH$_3$ | OH | 2 | 2 |
| CH$_3$ | H | —OCH$_2$CH(CH$_3$)O— | | CH$_3$ | CH$_3$ | OH | 2 | 2 |
| CH$_3$ | H | —OCH$_2$CH(CH$_3$)O— | | CH$_3$ | H | OH | 2 | 2 |
| CH$_3$ | H | —OCH$_2$CH(CH$_3$)O— | | H | H | OH | 2 | 2 |
| CH$_3$ | H | —OCH$_2$CH(CH$_3$)O— | | Cl | Cl | OH | 2 | 2 |
| CH$_3$ | H | —OCH$_2$CH(CH$_3$)O— | | Cl | H | OH | 2 | 2 |
| CH$_3$ | H | —OCH$_2$CH(CH$_3$)O— | | Cl | CH$_3$ | OH | 2 | 2 |
| H | H | —OCH$_2$CH$_2$CH$_2$O— | | CH$_3$ | CH$_3$ | OH | 2 | 2 |
| H | H | —OCH$_2$CH$_2$CH$_2$O— | | CH$_3$ | H | OH | 2 | 2 |
| H | H | —OCH$_2$CH$_2$CH$_2$O— | | H | H | OH | 2 | 2 |
| H | H | —OCH$_2$CH$_2$CH$_2$O— | | Cl | Cl | OH | 2 | 2 |
| H | H | —OCH$_2$CH$_2$CH$_2$O— | | Cl | H | OH | 2 | 2 |
| H | H | —OCH$_2$CH$_2$CH$_2$O— | | Cl | CH$_3$ | OH | 2 | 2 |
| CH$_3$ | CH$_3$ | —OCH$_2$CH$_2$CH$_2$O— | | CH$_3$ | CH$_3$ | OH | 2 | 2 |
| CH$_3$ | CH$_3$ | —OCH$_2$CH$_2$CH$_2$O— | | CH$_3$ | H | OH | 2 | 2 |
| CH$_3$ | CH$_3$ | —OCH$_2$CH$_2$CH$_2$O— | | H | H | OH | 2 | 2 |
| CH$_3$ | CH$_3$ | —OCH$_2$CH$_2$CH$_2$O— | | Cl | Cl | OH | 2 | 2 |
| CH$_3$ | CH$_3$ | —OCH$_2$CH$_2$CH$_2$O— | | Cl | H | OH | 2 | 2 |
| CH$_3$ | CH$_3$ | —OCH$_2$CH$_2$CH$_2$O— | | Cl | CH$_3$ | OH | 2 | 2 |
| CH$_3$ | H | —OCH$_2$CH$_2$CH$_2$O— | | CH$_3$ | CH$_3$ | OH | 2 | 2 |
| CH$_3$ | H | —OCH$_2$CH$_2$CH$_2$O— | | CH$_3$ | H | OH | 2 | 2 |
| CH$_3$ | H | —OCH$_2$CH$_2$CH$_2$O— | | H | H | OH | 2 | 2 |
| CH$_3$ | H | —OCH$_2$CH$_2$CH$_2$O— | | Cl | Cl | OH | 2 | 2 |
| CH$_3$ | H | —OCH$_2$CH$_2$CH$_2$O— | | Cl | H | OH | 2 | 2 |
| CH$_3$ | H | —OCH$_2$CH$_2$CH$_2$O— | | Cl | CH$_3$ | OH | 2 | 2 |
| H | H | —SCH$_2$CH$_2$S— | | CH$_3$ | CH$_3$ | OH | 2 | 1 |
| H | H | —SCH$_2$CH$_2$S— | | CH$_3$ | CH$_3$ | OH | 0 | 1 |
| H | H | —SCH$_2$CH$_2$S— | | CH$_3$ | H | OH | 2 | 1 |
| H | H | —SCH$_2$CH$_2$S— | | H | H | OH | 2 | 1 |
| H | H | —SCH$_2$CH$_2$S— | | Cl | Cl | OH | 2 | 1 |
| H | H | —SCH$_2$CH$_2$S— | | Cl | H | OH | 2 | 1 |
| H | H | —SCH$_2$CH$_2$S— | | Cl | CH$_3$ | OH | 2 | 1 |
| H | H | —SCH$_2$CH$_2$S— | | NO$_2$ | H | OH | 2 | 1 |
| CH$_3$ | CH$_3$ | —SCH$_2$CH$_2$S— | | CH$_3$ | CH$_3$ | OH | 2 | 1 |
| CH$_3$ | CH$_3$ | —SCH$_2$CH$_2$S— | | CH$_3$ | H | OH | 2 | 1 |
| CH$_3$ | CH$_3$ | —SCH$_2$CH$_2$S— | | H | H | OH | 2 | 1 |
| CH$_3$ | CH$_3$ | —SCH$_2$CH$_2$S— | | Cl | Cl | OH | 2 | 1 |
| CH$_3$ | CH$_3$ | —SCH$_2$CH$_2$S— | | Cl | H | OH | 2 | 1 |
| CH$_3$ | CH$_3$ | —SCH$_2$CH$_2$S— | | Cl | CH$_3$ | OH | 2 | 1 |
| CH$_3$ | H | —SCH$_2$CH$_2$S— | | CH$_3$ | CH$_3$ | OH | 2 | 1 |
| CH$_3$ | H | —SCH$_2$CH$_2$S— | | CH$_3$ | H | OH | 2 | 1 |
| CH$_3$ | H | —SCH$_2$CH$_2$S— | | H | H | OH | 2 | 1 |
| CH$_3$ | H | —SCH$_2$CH$_2$S— | | Cl | Cl | OH | 2 | 1 |
| CH$_3$ | H | —SCH$_2$CH$_2$S— | | Cl | H | OH | 2 | 1 |
| CH$_3$ | H | —SCH$_2$CH$_2$S— | | Cl | CH$_3$ | OH | 2 | 1 |
| H | H | —SCH$_2$CH$_2$O— | | CH$_3$ | CH$_3$ | OH | 2 | 1 |
| H | H | —SCH$_2$CH$_2$O— | | CH$_3$ | CH$_3$ | OH | 0 | 1 |
| H | H | —SCH$_2$CH$_2$O— | | CH$_3$ | H | OH | 2 | 1 |
| H | H | —SCH$_2$CH$_2$O— | | H | H | OH | 2 | 1 |
| H | H | —SCH$_2$CH$_2$O— | | Cl | Cl | OH | 2 | 1 |
| H | H | —SCH$_2$CH$_2$O— | | Cl | H | OH | 2 | 1 |
| H | H | —SCH$_2$CH$_2$O— | | Cl | CH$_3$ | OH | 2 | 1 |
| H | H | —SCH$_2$CH$_2$O— | | NO$_2$ | H | OH | 2 | 1 |
| CH$_3$ | CH$_3$ | —SCH$_2$CH$_2$O— | | CH$_3$ | CH$_3$ | OH | 2 | 1 |
| CH$_3$ | CH$_3$ | —SCH$_2$CH$_2$O— | | CH$_3$ | H | OH | 2 | 1 |
| CH$_3$ | CH$_3$ | —SCH$_2$CH$_2$O— | | H | H | OH | 2 | 1 |
| CH$_3$ | CH$_3$ | —SCH$_2$CH$_2$O— | | Cl | Cl | OH | 2 | 1 |
| CH$_3$ | CH$_3$ | —SCH$_2$CH$_2$O— | | Cl | H | OH | 2 | 1 |
| CH$_3$ | CH$_3$ | —SCH$_2$CH$_2$O— | | Cl | CH$_3$ | OH | 2 | 1 |
| CH$_3$ | H | —SCH$_2$CH$_2$O— | | CH$_3$ | CH$_3$ | OH | 2 | 1 |
| CH$_3$ | H | —SCH$_2$CH$_2$O— | | CH$_3$ | H | OH | 2 | 1 |
| CH$_3$ | H | —SCH$_2$CH$_2$O— | | H | H | OH | 2 | 1 |
| CH$_3$ | H | —SCH$_2$CH$_2$O— | | Cl | Cl | OH | 2 | 1 |
| CH$_3$ | H | —SCH$_2$CH$_2$O— | | Cl | H | OH | 2 | 1 |
| CH$_3$ | H | —SCH$_2$CH$_2$O— | | Cl | CH$_3$ | OH | 2 | 1 |
| H | H | —SCH$_2$CH$_2$CH$_2$S— | | CH$_3$ | CH$_3$ | OH | 2 | 1 |
| H | H | —SCH$_2$CH$_2$CH$_2$S— | | CH$_3$ | H | OH | 2 | 1 |
| H | H | —SCH$_2$CH$_2$CH$_2$S— | | H | H | OH | 2 | 1 |
| H | H | —SCH$_2$CH$_2$CH$_2$S— | | Cl | Cl | OH | 2 | 1 |
| H | H | —SCH$_2$CH$_2$CH$_2$S— | | Cl | H | OH | 2 | 1 |
| H | H | —SCH$_2$CH$_2$CH$_2$S— | | Cl | CH$_3$ | OH | 2 | 1 |
| H | H | —SCH$_2$CH$_2$CH$_2$S— | | NO$_2$ | H | OH | 2 | 1 |
| CH$_3$ | CH$_3$ | —SCH$_2$CH$_2$CH$_2$S— | | CH$_3$ | CH$_3$ | OH | 2 | 1 |
| CH$_3$ | CH$_3$ | —SCH$_2$CH$_2$CH$_2$S— | | CH$_3$ | H | OH | 2 | 1 |
| CH$_3$ | CH$_3$ | —SCH$_2$CH$_2$CH$_2$S— | | H | H | OH | 2 | 1 |
| CH$_3$ | CH$_3$ | —SCH$_2$CH$_2$CH$_2$S— | | Cl | Cl | OH | 2 | 1 |
| CH$_3$ | CH$_3$ | —SCH$_2$CH$_2$CH$_2$S— | | Cl | H | OH | 2 | 1 |
| CH$_3$ | CH$_3$ | —SCH$_2$CH$_2$CH$_2$S— | | Cl | CH$_3$ | OH | 2 | 1 |
| CH$_3$ | H | —SCH$_2$CH$_2$CH$_2$S— | | CH$_3$ | CH$_3$ | OH | 2 | 1 |
| CH$_3$ | H | —SCH$_2$CH$_2$CH$_2$S— | | CH$_3$ | H | OH | 2 | 1 |
| CH$_3$ | H | —SCH$_2$CH$_2$CH$_2$S— | | H | H | OH | 2 | 1 |
| CH$_3$ | H | —SCH$_2$CH$_2$CH$_2$S— | | Cl | Cl | OH | 2 | 1 |
| CH$_3$ | H | —SCH$_2$CH$_2$CH$_2$S— | | Cl | H | OH | 2 | 1 |
| CH$_3$ | H | —SCH$_2$CH$_2$CH$_2$S— | | Cl | CH$_3$ | OH | 2 | 1 |
| H | H | | oxo | CH$_3$ | CH$_3$ | OH | 2 | 1 |
| H | H | | oxo | CH$_3$ | H | OH | 2 | 1 |
| H | H | | oxo | H | H | OH | 2 | 1 |
| H | H | | oxo | Cl | Cl | OH | 2 | 1 |
| H | H | | oxo | Cl | H | OH | 2 | 1 |
| H | H | | oxo | Cl | CH$_3$ | OH | 2 | 1 |
| H | H | | oxo | NO$_2$ | H | OH | 2 | 1 |
| CH$_3$ | CH$_3$ | | oxo | CH$_3$ | CH$_3$ | OH | 2 | 1 |
| CH$_3$ | CH$_3$ | | oxo | CH$_3$ | H | OH | 2 | 1 |
| CH$_3$ | CH$_3$ | | oxo | H | H | OH | 2 | 1 |
| CH$_3$ | CH$_3$ | | oxo | Cl | Cl | OH | 2 | 1 |
| CH$_3$ | CH$_3$ | | oxo | Cl | H | OH | 2 | 1 |
| CH$_3$ | CH$_3$ | | oxo | Cl | CH$_3$ | OH | 2 | 1 |
| CH$_3$ | H | | oxo | CH$_3$ | CH$_3$ | OH | 2 | 1 |
| CH$_3$ | H | | oxo | CH$_3$ | H | OH | 2 | 1 |
| CH$_3$ | H | | oxo | H | H | OH | 2 | 1 |
| CH$_3$ | H | | oxo | Cl | Cl | OH | 2 | 1 |
| CH$_3$ | H | | oxo | Cl | H | OH | 2 | 1 |
| CH$_3$ | H | | oxo | Cl | CH$_3$ | OH | 2 | 1 |
| H | H | | oxo | CH$_3$ | CH$_3$ | OH | 1 | 1 |
| H | H | | oxo | CH$_3$ | H | OH | 1 | 1 |
| H | H | | oxo | H | H | OH | 1 | 1 |
| H | H | | oxo | Cl | Cl | OH | 1 | 1 |

TABLE 1-continued

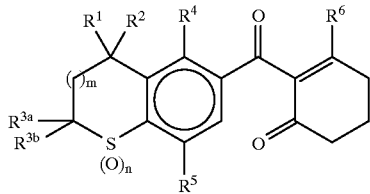

| R³ᵃ | R³ᵇ | R¹ | R² | R⁴ | R⁵ | R⁶ | n | m |
|---|---|---|---|---|---|---|---|---|
| H | H | oxo | | Cl | H | OH | 1 | 1 |
| H | H | oxo | | Cl | CH₃ | OH | 1 | 1 |
| CH₃ | CH₃ | oxo | | CH₃ | CH₃ | OH | 1 | 1 |
| CH₃ | CH₃ | oxo | | CH₃ | H | OH | 1 | 1 |
| CH₃ | CH₃ | oxo | | H | H | OH | 1 | 1 |
| CH₃ | CH₃ | oxo | | Cl | Cl | OH | 1 | 1 |
| CH₃ | CH₃ | oxo | | Cl | H | OH | 1 | 1 |
| CH₃ | CH₃ | oxo | | Cl | CH₃ | OH | 1 | 1 |
| CH₃ | H | oxo | | CH₃ | CH₃ | OH | 1 | 1 |
| CH₃ | H | oxo | | CH₃ | H | OH | 1 | 1 |
| CH₃ | H | oxo | | H | H | OH | 1 | 1 |
| CH₃ | H | oxo | | Cl | Cl | OH | 1 | 1 |
| CH₃ | H | oxo | | Cl | H | OH | 1 | 1 |
| CH₃ | H | oxo | | Cl | CH₃ | OH | 1 | 1 |

TABLE 2

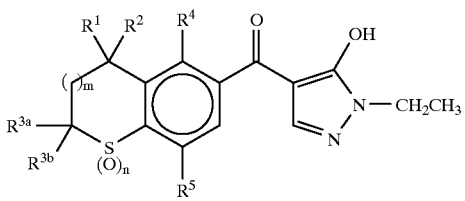

| R³ᵃ | R³ᵇ | R¹ | R² | R⁴ | R⁵ | n | m |
|---|---|---|---|---|---|---|---|
| H | H | —OCH₂CH₂O— | | CH₃ | CH₃ | 2 | 1 |
| H | H | —OCH₂CH₂O— | | CH₃ | H | 2 | 1 |
| H | H | —OCH₂CH₂O— | | H | H | 2 | 1 |
| H | H | —OCH₂CH₂O— | | Cl | Cl | 2 | 1 |
| H | H | —OCH₂CH₂O— | | Cl | H | 2 | 1 |
| H | H | —OCH₂CH₂O— | | Cl | CH₃ | 2 | 1 |
| H | H | —OCH₂CH₂O— | | NO₂ | H | 2 | 1 |
| CH₃ | CH₃ | —OCH₂CH₂O— | | CH₃ | CH₃ | 2 | 1 |
| CH₃ | CH₃ | —OCH₂CH₂O— | | CH₃ | H | 2 | 1 |
| CH₃ | CH₃ | —OCH₂CH₂O— | | H | H | 2 | 1 |
| CH₃ | CH₃ | —OCH₂CH₂O— | | Cl | Cl | 2 | 1 |
| CH₃ | CH₃ | —OCH₂CH₂O— | | Cl | H | 2 | 1 |
| CH₃ | CH₃ | —OCH₂CH₂O— | | Cl | CH₃ | 2 | 1 |
| CH₃ | H | —OCH₂CH₂O— | | CH₃ | CH₃ | 2 | 1 |
| CH₃ | H | —OCH₂CH₂O— | | CH₃ | H | 2 | 1 |
| CH₃ | H | —OCH₂CH₂O— | | H | H | 2 | 1 |
| CH₃ | H | —OCH₂CH₂O— | | Cl | Cl | 2 | 1 |
| CH₃ | H | —OCH₂CH₂O— | | Cl | H | 2 | 1 |
| CH₃ | H | —OCH₂CH₂O— | | Cl | CH₃ | 2 | 1 |
| H | H | —OCH₂CH(CH₃)O— | | CH₃ | CH₃ | 2 | 1 |
| H | H | —OCH₂CH(CH₃)O— | | CH₃ | H | 2 | 1 |
| H | H | —OCH₂CH(CH₃)O— | | H | H | 2 | 1 |
| H | H | —OCH₂CH(CH₃)O— | | Cl | Cl | 2 | 1 |
| H | H | —OCH₂CH(CH₃)O— | | Cl | H | 2 | 1 |
| H | H | —OCH₂CH(CH₃)O— | | Cl | CH₃ | 2 | 1 |
| CH₃ | CH₃ | —OCH₂CH(CH₃)O— | | CH₃ | CH₃ | 2 | 1 |
| CH₃ | CH₃ | —OCH₂CH(CH₃)O— | | CH₃ | H | 2 | 1 |
| CH₃ | CH₃ | —OCH₂CH(CH₃)O— | | H | H | 2 | 1 |
| CH₃ | CH₃ | —OCH₂CH(CH₃)O— | | Cl | Cl | 2 | 1 |
| CH₃ | CH₃ | —OCH₂CH(CH₃)O— | | Cl | H | 2 | 1 |
| CH₃ | CH₃ | —OCH₂CH(CH₃)O— | | Cl | CH₃ | 2 | 1 |
| CH₃ | H | —OCH₂CH(CH₃)O— | | CH₃ | CH₃ | 2 | 1 |
| CH₃ | H | —OCH₂CH(CH₃)O— | | CH₃ | H | 2 | 1 |
| CH₃ | H | —OCH₂CH(CH₃)O— | | H | H | 2 | 1 |

TABLE 2-continued

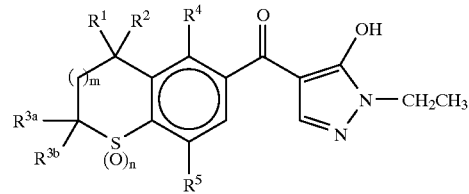

| R³ᵃ | R³ᵇ | R¹ | R² | R⁴ | R⁵ | n | m |
|---|---|---|---|---|---|---|---|
| CH₃ | H | —OCH₂CH(CH₃)O— | | Cl | Cl | 2 | 1 |
| CH₃ | H | —OCH₂CH(CH₃)O— | | Cl | H | 2 | 1 |
| CH₃ | H | —OCH₂CH(CH₃)O— | | Cl | CH₃ | 2 | 1 |
| H | H | —OCH₂CH₂CH₂O— | | CH₃ | CH₃ | 2 | 1 |
| H | H | —OCH₂CH₂CH₂O— | | CH₃ | H | 2 | 1 |
| H | H | —OCH₂CH₂CH₂O— | | H | H | 2 | 1 |
| H | H | —OCH₂CH₂CH₂O— | | Cl | Cl | 2 | 1 |
| H | H | —OCH₂CH₂CH₂O— | | Cl | H | 2 | 1 |
| H | H | —OCH₂CH₂CH₂O— | | Cl | CH₃ | 2 | 1 |
| CH₃ | CH₃ | —OCH₂CH₂CH₂O— | | CH₃ | CH₃ | 2 | 1 |
| CH₃ | CH₃ | —OCH₂CH₂CH₂O— | | CH₃ | H | 2 | 1 |
| CH₃ | CH₃ | —OCH₂CH₂CH₂O— | | H | H | 2 | 1 |
| CH₃ | CH₃ | —OCH₂CH₂CH₂O— | | Cl | Cl | 2 | 1 |
| CH₃ | CH₃ | —OCH₂CH₂CH₂O— | | Cl | H | 2 | 1 |
| CH₃ | CH₃ | —OCH₂CH₂CH₂O— | | Cl | CH₃ | 2 | 1 |
| CH₃ | H | —OCH₂CH₂CH₂O— | | CH₃ | CH₃ | 2 | 1 |
| CH₃ | H | —OCH₂CH₂CH₂O— | | CH₃ | H | 2 | 1 |
| CH₃ | H | —OCH₂CH₂CH₂O— | | H | H | 2 | 1 |
| CH₃ | H | —OCH₂CH₂CH₂O— | | Cl | Cl | 2 | 1 |
| CH₃ | H | —OCH₂CH₂CH₂O— | | Cl | H | 2 | 1 |
| CH₃ | H | —OCH₂CH₂CH₂O— | | Cl | CH₃ | 2 | 1 |
| H | H | CH₃O | CH₃O | CH₃ | CH₃ | 2 | 1 |
| H | H | CH₃O | CH₃O | CH₃ | H | 2 | 1 |
| H | H | CH₃O | CH₃O | H | H | 2 | 1 |
| H | H | CH₃O | CH₃O | Cl | Cl | 2 | 1 |
| H | H | CH₃O | CH₃O | Cl | H | 2 | 1 |
| H | H | CH₃O | CH₃O | Cl | CH₃ | 2 | 1 |
| CH₃ | CH₃ | CH₃O | CH₃O | CH₃ | CH₃ | 2 | 1 |
| CH₃ | CH₃ | CH₃O | CH₃O | CH₃ | H | 2 | 1 |
| CH₃ | CH₃ | CH₃O | CH₃O | H | H | 2 | 1 |
| CH₃ | CH₃ | CH₃O | CH₃O | Cl | Cl | 2 | 1 |
| CH₃ | CH₃ | CH₃O | CH₃O | Cl | H | 2 | 1 |
| CH₃ | CH₃ | CH₃O | CH₃O | Cl | CH₃ | 2 | 1 |
| CH₃ | H | CH₃O | CH₃O | CH₃ | CH₃ | 2 | 1 |
| CH₃ | H | CH₃O | CH₃O | CH₃ | H | 2 | 1 |
| CH₃ | H | CH₃O | CH₃O | H | H | 2 | 1 |
| CH₃ | H | CH₃O | CH₃O | Cl | Cl | 2 | 1 |
| CH₃ | H | CH₃O | CH₃O | Cl | H | 2 | 1 |
| CH₃ | H | CH₃O | CH₃O | Cl | CH₃ | 2 | 1 |
| H | H | H₅C₂O | H₅C₂O | CH₃ | CH₃ | 2 | 1 |
| H | H | H₅C₂O | H₅C₂O | CH₃ | H | 2 | 1 |
| H | H | H₅C₂O | H₅C₂O | H | H | 2 | 1 |
| H | H | H₅C₂O | H₅C₂O | Cl | Cl | 2 | 1 |
| H | H | H₅C₂O | H₅C₂O | Cl | H | 2 | 1 |
| H | H | H₅C₂O | H₅C₂O | Cl | CH₃ | 2 | 1 |
| CH₃ | CH₃ | H₅C₂O | H₅C₂O | CH₃ | CH₃ | 2 | 1 |
| CH₃ | CH₃ | H₅C₂O | H₅C₂O | CH₃ | H | 2 | 1 |
| CH₃ | CH₃ | H₅C₂O | H₅C₂O | H | H | 2 | 1 |
| CH₃ | CH₃ | H₅C₂O | H₅C₂O | Cl | Cl | 2 | 1 |
| CH₃ | CH₃ | H₅C₂O | H₅C₂O | Cl | H | 2 | 1 |
| CH₃ | CH₃ | H₅C₂O | H₅C₂O | Cl | CH₃ | 2 | 1 |
| CH₃ | H | H₅C₂O | H₅C₂O | CH₃ | CH₃ | 2 | 1 |
| CH₃ | H | H₅C₂O | H₅C₂O | CH₃ | H | 2 | 1 |
| CH₃ | H | H₅C₂O | H₅C₂O | H | H | 2 | 1 |
| CH₃ | H | H₅C₂O | H₅C₂O | Cl | Cl | 2 | 1 |
| CH₃ | H | H₅C₂O | H₅C₂O | Cl | H | 2 | 1 |
| CH₃ | H | H₅C₂O | H₅C₂O | Cl | CH₃ | 2 | 1 |
| H | H | —OCH₂CH₂O— | | CH₃ | CH₃ | 0 | 1 |
| H | H | —OCH₂CH(CH₃)O— | | CH₃ | CH₃ | 0 | 1 |
| H | H | —OCH₂CH₂CH₂O— | | CH₃ | CH₃ | 0 | 1 |
| H | H | CH₃O | CH₃O | CH₃ | CH₃ | 0 | 1 |
| H | H | H₅C₂O | H₅C₂O | CH₃ | CH₃ | 0 | 1 |
| H | H | —OCH₂CH₂O— | | CH₃ | CH₃ | 1 | 1 |
| H | H | —OCH₂CH(CH₃)O— | | CH₃ | CH₃ | 1 | 1 |
| H | H | —OCH₂CH₂CH₂O— | | CH₃ | CH₃ | 1 | 1 |
| H | H | CH₃O | CH₃O | CH₃ | CH₃ | 1 | 1 |
| H | H | H₅C₂O | H₅C₂O | CH₃ | CH₃ | 1 | 1 |

TABLE 2-continued

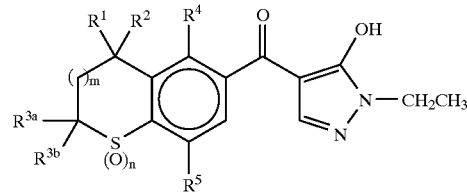

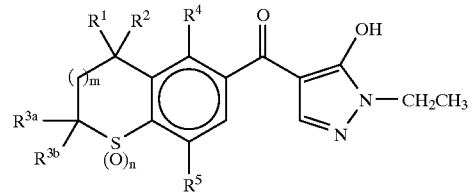

| R³ᵃ | R³ᵇ | R¹ | R² | R⁴ | R⁵ | n | m |
|---|---|---|---|---|---|---|---|
| H | H | —OCH₂CH₂O— | | CH₃ | CH₃ | 2 | 2 |
| H | H | —OCH₂CH(CH₃)O— | | CH₃ | CH₃ | 2 | 2 |
| H | H | —OCH₂CH₂CH₂O— | | CH₃ | CH₃ | 2 | 2 |
| H | H | CH₃O | CH₃O | CH₃ | CH₃ | 2 | 2 |
| H | H | H₅C₂O | H₅C₂O | CH₃ | CH₃ | 2 | 2 |
| H | H | —CH₂CH₂CH₂CH₂— | | CH₃ | CH₃ | 2 | 1 |
| H | H | —CH₂CH₂CH₂CH₂— | | CH₃ | H | 2 | 1 |
| H | H | —CH₂CH₂CH₂CH₂— | | H | H | 2 | 1 |
| H | H | —CH₂CH₂CH₂CH₂— | | Cl | Cl | 2 | 1 |
| H | H | —CH₂CH₂CH₂CH₂— | | Cl | H | 2 | 1 |
| H | H | —CH₂CH₂CH₂CH₂— | | Cl | CH₃ | 2 | 1 |
| CH₃ | CH₃ | —CH₂CH₂CH₂CH₂— | | CH₃ | CH₃ | 2 | 1 |
| CH₃ | CH₃ | —CH₂CH₂CH₂CH₂— | | CH₃ | H | 2 | 1 |
| CH₃ | CH₃ | —CH₂CH₂CH₂CH₂— | | H | H | 2 | 1 |
| CH₃ | CH₃ | —CH₂CH₂CH₂CH₂— | | Cl | Cl | 2 | 1 |
| CH₃ | CH₃ | —CH₂CH₂CH₂CH₂— | | Cl | H | 2 | 1 |
| CH₃ | CH₃ | —CH₂CH₂CH₂CH₂— | | Cl | CH₃ | 2 | 1 |
| CH₃ | H | —CH₂CH₂CH₂CH₂— | | CH₃ | CH₃ | 2 | 1 |
| CH₃ | H | —CH₂CH₂CH₂CH₂— | | CH₃ | H | 2 | 1 |
| CH₃ | H | —CH₂CH₂CH₂CH₂— | | H | H | 2 | 1 |
| CH₃ | H | —CH₂CH₂CH₂CH₂— | | Cl | Cl | 2 | 1 |
| CH₃ | H | —CH₂CH₂CH₂CH₂— | | Cl | H | 2 | 1 |
| CH₃ | H | —CH₂CH₂CH₂CH₂— | | Cl | CH₃ | 2 | 1 |
| H | H | —CH₂CH₂CH₂CH₂CH₂— | | CH₃ | CH₃ | 2 | 1 |
| H | H | —CH₂CH₂CH₂CH₂CH₂— | | CH₃ | H | 2 | 1 |
| H | H | —CH₂CH₂CH₂CH₂CH₂— | | H | H | 2 | 1 |
| H | H | —CH₂CH₂CH₂CH₂CH₂— | | Cl | Cl | 2 | 1 |
| H | H | —CH₂CH₂CH₂CH₂CH₂— | | Cl | H | 2 | 1 |
| H | H | —CH₂CH₂CH₂CH₂CH₂— | | Cl | CH₃ | 2 | 1 |
| CH₃ | CH₃ | —CH₂CH₂CH₂CH₂CH₂— | | CH₃ | CH₃ | 2 | 1 |
| CH₃ | CH₃ | —CH₂CH₂CH₂CH₂CH₂— | | CH₃ | H | 2 | 1 |
| CH₃ | CH₃ | —CH₂CH₂CH₂CH₂CH₂— | | H | H | 2 | 1 |
| CH₃ | CH₃ | —CH₂CH₂CH₂CH₂CH₂— | | Cl | Cl | 2 | 1 |
| CH₃ | CH₃ | —CH₂CH₂CH₂CH₂CH₂— | | Cl | H | 2 | 1 |
| CH₃ | CH₃ | —CH₂CH₂CH₂CH₂CH₂— | | Cl | CH₃ | 2 | 1 |
| CH₃ | H | —CH₂CH₂CH₂CH₂CH₂— | | CH₃ | CH₃ | 2 | 1 |
| CH₃ | H | —CH₂CH₂CH₂CH₂CH₂— | | CH₃ | H | 2 | 1 |
| CH₃ | H | —CH₂CH₂CH₂CH₂CH₂— | | H | H | 2 | 1 |
| CH₃ | H | —CH₂CH₂CH₂CH₂CH₂— | | Cl | Cl | 2 | 1 |
| CH₃ | H | —CH₂CH₂CH₂CH₂CH₂— | | Cl | H | 2 | 1 |
| CH₃ | H | —CH₂CH₂CH₂CH₂CH₂— | | Cl | CH₃ | 2 | 1 |
| H | H | —CH₂CH₂CH₂O— | | CH₃ | CH₃ | 2 | 1 |
| H | H | —CH₂CH₂CH₂O— | | CH₃ | H | 2 | 1 |
| H | H | —CH₂CH₂CH₂O— | | H | H | 2 | 1 |
| H | H | —CH₂CH₂CH₂O— | | Cl | Cl | 2 | 1 |
| H | H | —CH₂CH₂CH₂O— | | Cl | H | 2 | 1 |
| H | H | —CH₂CH₂CH₂O— | | Cl | CH₃ | 2 | 1 |
| CH₃ | CH₃ | —CH₂CH₂CH₂O— | | CH₃ | CH₃ | 2 | 1 |
| CH₃ | CH₃ | —CH₂CH₂CH₂O— | | CH₃ | H | 2 | 1 |
| CH₃ | CH₃ | —CH₂CH₂CH₂O— | | H | H | 2 | 1 |
| CH₃ | CH₃ | —CH₂CH₂CH₂O— | | Cl | Cl | 2 | 1 |
| CH₃ | CH₃ | —CH₂CH₂CH₂O— | | Cl | H | 2 | 1 |
| CH₃ | CH₃ | —CH₂CH₂CH₂O— | | Cl | CH₃ | 2 | 1 |
| CH₃ | H | —CH₂CH₂CH₂O— | | CH₃ | CH₃ | 2 | 1 |
| CH₃ | H | —CH₂CH₂CH₂O— | | CH₃ | H | 2 | 1 |
| CH₃ | H | —CH₂CH₂CH₂O— | | H | H | 2 | 1 |
| CH₃ | H | —CH₂CH₂CH₂O— | | Cl | Cl | 2 | 1 |
| CH₃ | H | —CH₂CH₂CH₂O— | | Cl | H | 2 | 1 |
| CH₃ | H | —CH₂CH₂CH₂O— | | Cl | CH₃ | 2 | 1 |
| H | H | —OCH₂CH₂O— | | CH₃ | CH₃ | 2 | 0 |
| H | H | —OCH₂CH₂O— | | CH₃ | H | 2 | 0 |
| H | H | —OCH₂CH₂O— | | H | H | 2 | 0 |
| H | H | —OCH₂CH₂O— | | Cl | Cl | 2 | 0 |
| H | H | —OCH₂CH₂O— | | Cl | H | 2 | 0 |
| H | H | —OCH₂CH₂O— | | Cl | CH₃ | 2 | 0 |
| CH₃ | CH₃ | —OCH₂CH₂O— | | CH₃ | CH₃ | 2 | 0 |
| CH₃ | CH₃ | —OCH₂CH₂O— | | CH₃ | H | 2 | 0 |
| CH₃ | CH₃ | —OCH₂CH₂O— | | H | H | 2 | 0 |
| CH₃ | CH₃ | —OCH₂CH₂O— | | Cl | Cl | 2 | 0 |
| CH₃ | CH₃ | —OCH₂CH₂O— | | Cl | H | 2 | 0 |
| CH₃ | CH₃ | —OCH₂CH₂O— | | Cl | CH₃ | 2 | 0 |
| CH₃ | H | —OCH₂CH₂O— | | CH₃ | CH₃ | 2 | 0 |
| CH₃ | H | —OCH₂CH₂O— | | CH₃ | H | 2 | 0 |
| CH₃ | H | —OCH₂CH₂O— | | H | H | 2 | 0 |
| CH₃ | H | —OCH₂CH₂O— | | Cl | Cl | 2 | 0 |
| CH₃ | H | —OCH₂CH₂O— | | Cl | H | 2 | 0 |
| CH₃ | H | —OCH₂CH₂O— | | Cl | CH₃ | 2 | 0 |
| H | H | —OCH₂CH₂O— | | CH₃ | CH₃ | 2 | 2 |
| H | H | —OCH₂CH₂O— | | CH₃ | H | 2 | 2 |
| H | H | —OCH₂CH₂O— | | H | H | 2 | 2 |
| H | H | —OCH₂CH₂O— | | Cl | Cl | 2 | 2 |
| H | H | —OCH₂CH₂O— | | Cl | H | 2 | 2 |
| H | H | —OCH₂CH₂O— | | Cl | CH₃ | 2 | 2 |
| CH₃ | CH₃ | —OCH₂CH₂O— | | CH₃ | CH₃ | 2 | 2 |
| CH₃ | CH₃ | —OCH₂CH₂O— | | CH₃ | H | 2 | 2 |
| CH₃ | CH₃ | —OCH₂CH₂O— | | H | H | 2 | 2 |
| CH₃ | CH₃ | —OCH₂CH₂O— | | Cl | Cl | 2 | 2 |
| CH₃ | CH₃ | —OCH₂CH₂O— | | Cl | H | 2 | 2 |
| CH₃ | CH₃ | —OCH₂CH₂O— | | Cl | CH₃ | 2 | 2 |
| CH₃ | H | —OCH₂CH₂O— | | CH₃ | CH₃ | 2 | 2 |
| CH₃ | H | —OCH₂CH₂O— | | CH₃ | H | 2 | 2 |
| CH₃ | H | —OCH₂CH₂O— | | H | H | 2 | 2 |
| CH₃ | H | —OCH₂CH₂O— | | Cl | Cl | 2 | 2 |
| CH₃ | H | —O—CH₂CH₂—O— | | Cl | H | 2 | 2 |
| CH₃ | H | —O—CH₂CH₂—O— | | Cl | CH₃ | 2 | 2 |
| H | H | —OCH₂CH₂CH₂—O— | | CH₃ | CH₃ | 2 | 0 |
| H | H | —OCH₂CH₂CH₂—O— | | CH₃ | H | 2 | 0 |
| H | H | —OCH₂CH₂CH₂—O— | | H | H | 2 | 0 |
| H | H | —OCH₂CH₂CH₂—O— | | Cl | Cl | 2 | 0 |
| H | H | —OCH₂CH₂CH₂—O— | | Cl | H | 2 | 0 |
| H | H | —OCH₂CH₂CH₂—O— | | Cl | CH₃ | 2 | 0 |
| CH₃ | CH₃ | —OCH₂CH₂CH₂—O— | | CH₃ | CH₃ | 2 | 0 |
| CH₃ | CH₃ | —OCH₂CH₂CH₂—O— | | CH₃ | H | 2 | 0 |
| CH₃ | CH₃ | —OCH₂CH₂CH₂—O— | | H | H | 2 | 0 |
| CH₃ | CH₃ | —OCH₂CH₂CH₂—O— | | Cl | Cl | 2 | 0 |
| CH₃ | CH₃ | —OCH₂CH₂CH₂—O— | | Cl | H | 2 | 0 |
| CH₃ | CH₃ | —OCH₂CH₂CH₂—O— | | Cl | CH₃ | 2 | 0 |
| CH₃ | H | —OCH₂CH₂CH₂—O— | | CH₃ | CH₃ | 2 | 0 |
| CH₃ | H | —OCH₂CH₂CH₂—O— | | CH₃ | H | 2 | 0 |
| CH₃ | H | —OCH₂CH₂CH₂—O— | | H | H | 2 | 0 |
| CH₃ | H | —OCH₂CH₂CH₂—O— | | Cl | Cl | 2 | 0 |
| CH₃ | H | —OCH₂CH₂CH₂—O— | | Cl | H | 2 | 0 |
| CH₃ | H | —OCH₂CH₂CH₂—O— | | Cl | CH₃ | 2 | 0 |
| H | H | —SCH₂CH₂S— | | CH₃ | CH₃ | 2 | 1 |
| H | H | —SCH₂CH₂S— | | CH₃ | CH₃ | 0 | 1 |
| H | H | —SCH₂CH₂S— | | CH₃ | H | 2 | 1 |
| H | H | —SCH₂CH₂S— | | H | H | 2 | 1 |
| H | H | —SCH₂CH₂S— | | Cl | Cl | 2 | 1 |
| H | H | —SCH₂CH₂S— | | Cl | H | 2 | 1 |
| H | H | —SCH₂CH₂S— | | Cl | CH₃ | 2 | 1 |
| H | H | —SCH₂CH₂S— | | NO₂ | H | 2 | 1 |
| CH₃ | CH₃ | —SCH₂CH₂S— | | CH₃ | CH₃ | 2 | 1 |
| CH₃ | CH₃ | —SCH₂CH₂S— | | CH₃ | H | 2 | 1 |
| CH₃ | CH₃ | —SCH₂CH₂S— | | H | H | 2 | 1 |
| CH₃ | CH₃ | —SCH₂CH₂S— | | Cl | Cl | 2 | 1 |
| CH₃ | CH₃ | —SCH₂CH₂S— | | Cl | H | 2 | 1 |
| CH₃ | CH₃ | —SCH₂CH₂S— | | Cl | CH₃ | 2 | 1 |
| CH₃ | H | —SCH₂CH₂S— | | CH₃ | CH₃ | 2 | 1 |
| CH₃ | H | —SCH₂CH₂S— | | CH₃ | H | 2 | 1 |
| CH₃ | H | —SCH₂CH₂S— | | H | H | 2 | 1 |
| CH₃ | H | —SCH₂CH₂S— | | Cl | Cl | 2 | 1 |
| CH₃ | H | —SCH₂CH₂S— | | Cl | H | 2 | 1 |

TABLE 2-continued

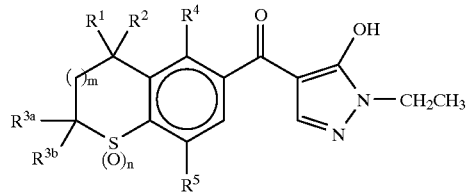

| R3a | R3b | R1 R2 | R4 | R5 | n | m |
|---|---|---|---|---|---|---|
| CH3 | H | —SCH2CH2S— | Cl | CH3 | 2 | 1 |
| H | H | —SCH2CH2O— | CH3 | CH3 | 2 | 1 |
| H | H | —SCH2CH2O— | CH3 | CH3 | 0 | 1 |
| H | H | —SCH2CH2O— | CH3 | H | 2 | 1 |
| H | H | —SCH2CH2O— | H | H | 2 | 1 |
| H | H | —SCH2CH2O— | Cl | Cl | 2 | 1 |
| H | H | —SCH2CH2O— | Cl | H | 2 | 1 |
| H | H | —SCH2CH2O— | Cl | CH3 | 2 | 1 |
| H | H | —SCH2CH2O— | NO2 | H | 2 | 1 |
| CH3 | CH3 | —SCH2CH2O— | CH3 | CH3 | 2 | 1 |
| CH3 | CH3 | —SCH2CH2O— | CH3 | H | 2 | 1 |
| CH3 | CH3 | —SCH2CH2O— | H | H | 2 | 1 |
| CH3 | CH3 | —SCH2CH2O— | Cl | Cl | 2 | 1 |
| CH3 | CH3 | —SCH2CH2O— | Cl | H | 2 | 1 |
| CH3 | CH3 | —SCH2CH2O— | Cl | CH3 | 2 | 1 |
| CH3 | H | —SCH2CH2O— | CH3 | CH3 | 2 | 1 |
| CH3 | H | —SCH2CH2O— | CH3 | H | 2 | 1 |
| CH3 | H | —SCH2CH2O— | H | H | 2 | 1 |
| CH3 | H | —SCH2CH2O— | Cl | Cl | 2 | 1 |
| CH3 | H | —SCH2CH2O— | Cl | H | 2 | 1 |
| CH3 | H | —SCH2CH2O— | Cl | CH3 | 2 | 1 |
| H | H | —SCH2CH2CH2S— | CH3 | CH3 | 2 | 1 |
| H | H | —SCH2CH2CH2S— | CH3 | H | 2 | 1 |
| H | H | —SCH2CH2CH2S— | H | H | 2 | 1 |
| H | H | —SCH2CH2CH2S— | Cl | Cl | 2 | 1 |
| H | H | —SCH2CH2CH2S— | Cl | H | 2 | 1 |
| H | H | —SCH2CH2CH2S— | Cl | CH3 | 2 | 1 |
| H | H | —SCH2CH2CH2S— | NO2 | H | 2 | 1 |
| CH3 | CH3 | —SCH2CH2CH2S— | CH3 | CH3 | 2 | 1 |
| CH3 | CH3 | —SCH2CH2CH2S— | CH3 | H | 2 | 1 |
| CH3 | CH3 | —SCH2CH2CH2S— | H | H | 2 | 1 |
| CH3 | CH3 | —SCH2CH2CH2S— | Cl | Cl | 2 | 1 |
| CH3 | CH3 | —SCH2CH2CH2S— | Cl | H | 2 | 1 |
| CH3 | CH3 | —SCH2CH2CH2S— | Cl | CH3 | 2 | 1 |
| CH3 | H | —SCH2CH2CH2S— | CH3 | CH3 | 2 | 1 |
| CH3 | H | —SCH2CH2CH2S— | CH3 | H | 2 | 1 |
| CH3 | H | —SCH2CH2CH2S— | H | H | 2 | 1 |
| CH3 | H | —SCH2CH2CH2S— | Cl | Cl | 2 | 1 |
| CH3 | H | —SCH2CH2CH2S— | Cl | H | 2 | 1 |
| CH3 | H | —SCH2CH2CH2S— | Cl | CH3 | 2 | 1 |
| H | H | oxo | CH3 | CH3 | 2 | 1 |
| H | H | oxo | CH3 | H | 2 | 1 |
| H | H | oxo | Cl | Cl | 2 | 1 |
| H | H | oxo | Cl | H | 2 | 1 |

TABLE 2-continued

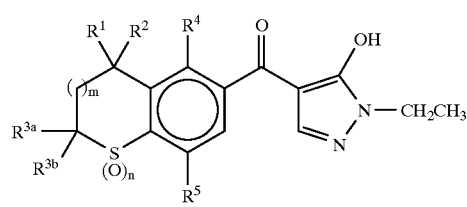

| R3a | R3b | R1 | R2 | R4 | R5 | n | m |
|---|---|---|---|---|---|---|---|
| H | H | oxo | | Cl | CH3 | 2 | 1 |
| H | H | oxo | | NO2 | H | 2 | 1 |
| CH3 | CH3 | oxo | | CH3 | CH3 | 2 | 1 |
| CH3 | CH3 | oxo | | CH3 | H | 2 | 1 |
| CH3 | CH3 | oxo | | H | H | 2 | 1 |
| CH3 | CH3 | oxo | | Cl | Cl | 2 | 1 |
| CH3 | CH3 | oxo | | Cl | H | 2 | 1 |
| CH3 | CH3 | oxo | | Cl | CH3 | 2 | 1 |
| CH3 | H | oxo | | CH3 | CH3 | 2 | 1 |
| CH3 | H | oxo | | CH3 | H | 2 | 1 |
| CH3 | H | oxo | | H | H | 2 | 1 |
| CH3 | H | oxo | | Cl | Cl | 2 | 1 |
| CH3 | H | oxo | | Cl | H | 2 | 1 |
| CH3 | H | oxo | | Cl | CH3 | 2 | 1 |
| H | H | oxo | | CH3 | CH3 | 1 | 1 |
| H | H | oxo | | CH3 | H | 1 | 1 |
| H | H | oxo | | H | H | 1 | 1 |
| H | H | oxo | | Cl | Cl | 1 | 1 |
| H | H | oxo | | Cl | H | 1 | 1 |
| H | H | oxo | | Cl | CH3 | 1 | 1 |
| CH3 | CH3 | oxo | | CH3 | CH3 | 1 | 1 |
| CH3 | CH3 | oxo | | CH3 | H | 1 | 1 |
| CH3 | CH3 | oxo | | H | H | 1 | 1 |
| CH3 | CH3 | oxo | | Cl | Cl | 1 | 1 |
| CH3 | CH3 | oxo | | Cl | H | 1 | 1 |
| CH3 | CH3 | oxo | | Cl | CH3 | 1 | 1 |
| CH3 | H | oxo | | CH3 | CH3 | 1 | 1 |
| CH3 | H | oxo | | CH3 | H | 1 | 1 |
| CH3 | H | oxo | | H | H | 1 | 1 |
| CH3 | H | oxo | | Cl | Cl | 1 | 1 |
| CH3 | H | oxo | | Cl | H | 1 | 1 |
| CH3 | H | oxo | | Cl | CH3 | 1 | 1 |

TABLE 3

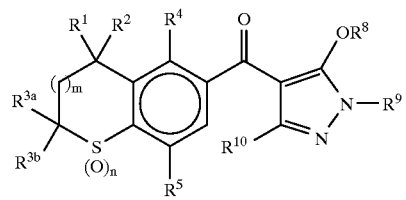

| R3a | R3b | R1 R2 | R4 | R5 | R8 | R9 | R10 | n | m |
|---|---|---|---|---|---|---|---|---|---|
| H | H | —OCH2CH2O— | CH3 | CH3 | SO2CH3 | C2H5 | H | 2 | 1 |
| H | H | —OCH2CH2O— | CH3 | CH3 | SO2CH2Cl | C2H5 | H | 2 | 1 |
| H | H | —OCH2CH2O— | CH3 | H | SO2CH3 | C2H5 | H | 2 | 1 |
| H | H | —OCH2CH2O— | H | H | SO2CH3 | C2H5 | H | 2 | 1 |

TABLE 3-continued

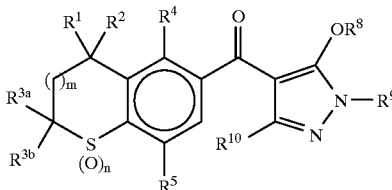

| R³ᵃ | R³ᵇ | R¹ | R² | R⁴ | R⁵ | R⁸ | R⁹ | R¹⁰ | n | m |
|---|---|---|---|---|---|---|---|---|---|---|
| H | H | —OCH₂CH₂O— | | Cl | Cl | SO₂CH₃ | C₂H₅ | H | 2 | 1 |
| H | H | —OCH₂CH₂O— | | Cl | H | SO₂CH₃ | C₂H₅ | H | 2 | 1 |
| H | H | —OCH₂CH₂O— | | Cl | CH₃ | SO₂CH₃ | C₂H₅ | H | 2 | 1 |
| H | H | —OCH₂CH₂O— | | CH₃ | CH₃ | SO₂C₂H₅ | C₂H₅ | H | 2 | 1 |
| H | H | —OCH₂CH₂O— | | CH₃ | H | SO₂C₂H₅ | C₂H₅ | H | 2 | 1 |
| H | H | —OCH₂CH₂O— | | H | H | SO₂C₂H₅ | C₂H₅ | H | 2 | 1 |
| H | H | —OCH₂CH₂O— | | Cl | Cl | SO₂C₂H₅ | C₂H₅ | H | 2 | 1 |
| H | H | —OCH₂CH₂O— | | Cl | H | SO₂C₂H₅ | C₂H₅ | H | 2 | 1 |
| H | H | —OCH₂CH₂O— | | Cl | CH₃ | SO₂C₂H₅ | C₂H₅ | H | 2 | 1 |
| H | H | —OCH₂CH₂O— | | CH₃ | CH₃ | SO₂-n-C₃H₇ | C₂H₅ | H | 2 | 1 |
| H | H | —OCH₂CH₂O— | | CH₃ | H | SO₂-n-C₃H₇ | C₂H₅ | H | 2 | 1 |
| H | H | —OCH₂CH₂O— | | H | H | SO₂-n-C₃H₇ | C₂H₅ | H | 2 | 1 |
| H | H | —OCH₂CH₂O— | | Cl | Cl | SO₂-n-C₃H₇ | C₂H₅ | H | 2 | 1 |
| H | H | —OCH₂CH₂O— | | Cl | H | SO₂-n-C₃H₇ | C₂H₅ | H | 2 | 1 |
| H | H | —OCH₂CH₂O— | | Cl | CH₃ | SO₂-n-C₃H₇ | C₂H₅ | H | 2 | 1 |
| H | H | —OCH₂CH₂O— | | CH₃ | CH₃ | SO₂-n-C₄H₉ | C₂H₅ | H | 2 | 1 |
| H | H | —OCH₂CH₂O— | | CH₃ | H | SO₂-n-C₄H₉ | C₂H₅ | H | 2 | 1 |
| H | H | —OCH₂CH₂O— | | H | H | SO₂-n-C₄H₉ | C₂H₅ | H | 2 | 1 |
| H | H | —OCH₂CH₂O— | | Cl | Cl | SO₂-n-C₄H₉ | C₂H₅ | H | 2 | 1 |
| H | H | —OCH₂CH₂O— | | Cl | H | SO₂-n-C₄H₉ | C₂H₅ | H | 2 | 1 |
| H | H | —OCH₂CH₂O— | | Cl | CH₃ | SO₂-n-C₄H₉ | C₂H₅ | H | 2 | 1 |
| H | H | —OCH₂CH₂O— | | CH₃ | CH₃ | SO₂-p-tolyl | C₂H₅ | H | 2 | 1 |
| H | H | —OCH₂CH₂O— | | CH₃ | H | SO₂-p-tolyl | C₂H₅ | H | 2 | 1 |
| H | H | —OCH₂CH₂O— | | H | H | SO₂-p-tolyl | C₂H₅ | H | 2 | 1 |
| H | H | —OCH₂CH₂O— | | Cl | Cl | SO₂-p-tolyl | C₂H₅ | H | 2 | 1 |
| H | H | —OCH₂CH₂O— | | Cl | H | SO₂-p-tolyl | C₂H₅ | H | 2 | 1 |
| H | H | —OCH₂CH₂O— | | Cl | CH₃ | SO₂-p-tolyl | C₂H₅ | H | 2 | 1 |
| H | H | —OCH₂CH₂O— | | CH₃ | CH₃ | SO₂-p-NO₂C₆H₄ | C₂H₅ | H | 2 | 1 |
| H | H | —OCH₂CH₂O— | | CH₃ | H | SO₂-p-NO₂C₆H₄ | C₂H₅ | H | 2 | 1 |
| H | H | —OCH₂CH₂O— | | H | H | SO₂-p-NO₂C₆H₄ | C₂H₅ | H | 2 | 1 |
| H | H | —OCH₂CH₂O— | | Cl | Cl | SO₂-p-NO₂C₆H₄ | C₂H₅ | H | 2 | 1 |
| H | H | —OCH₂CH₂O— | | Cl | H | SO₂-p-NO₂C₆H₄ | C₂H₅ | H | 2 | 1 |
| H | H | —OCH₂CH₂O— | | Cl | CH₃ | SO₂-p-NO₂C₆H₄ | C₂H₅ | H | 2 | 1 |
| H | H | —OCH₂CH₂O— | | CH₃ | CH₃ | SO₂-p-ClC₆H₄ | C₂H₅ | H | 2 | 1 |
| H | H | —OCH₂CH₂O— | | CH₃ | H | SO₂-p-ClC₆H₄ | C₂H₅ | H | 2 | 1 |
| H | H | —OCH₂CH₂O— | | H | H | SO₂-p-ClC₆H₄ | C₂H₅ | H | 2 | 1 |
| H | H | —OCH₂CH₂O— | | Cl | Cl | SO₂-p-ClC₆H₄ | C₂H₅ | H | 2 | 1 |
| H | H | —OCH₂CH₂O— | | Cl | H | SO₂-p-ClC₆H₄ | C₂H₅ | H | 2 | 1 |
| H | H | —OCH₂CH₂O— | | Cl | CH₃ | SO₂-p-ClC₆H₄ | C₂H₅ | H | 2 | 1 |
| H | H | —OCH₂CH₂O— | | CH₃ | CH₃ | C(=O)CH₃ | C₂H₅ | H | 2 | 1 |
| H | H | —OCH₂CH₂O— | | CH₃ | H | C(=O)CH₃ | C₂H₅ | H | 2 | 1 |
| H | H | —OCH₂CH₂O— | | H | H | C(=O)CH₃ | C₂H₅ | H | 2 | 1 |
| H | H | —OCH₂CH₂O— | | Cl | Cl | C(=O)CH₃ | C₂H₅ | H | 2 | 1 |
| H | H | —OCH₂CH₂O— | | Cl | H | C(=O)CH₃ | C₂H₅ | H | 2 | 1 |
| H | H | —OCH₂CH₂O— | | Cl | CH₃ | C(=O)CH₃ | C₂H₅ | H | 2 | 1 |
| H | H | —OCH₂CH₂O— | | CH₃ | CH₃ | C(=O)C₂H₅ | C₂H₅ | H | 2 | 1 |
| H | H | —OCH₂CH₂O— | | CH₃ | H | C(=O)C₂H₅ | C₂H₅ | H | 2 | 1 |
| H | H | —OCH₂CH₂O— | | H | H | C(=O)C₂H₅ | C₂H₅ | H | 2 | 1 |
| H | H | —OCH₂CH₂O— | | Cl | Cl | C(=O)C₂H₅ | C₂H₅ | H | 2 | 1 |
| H | H | —OCH₂CH₂O— | | Cl | H | C(=O)C₂H₅ | C₂H₅ | H | 2 | 1 |
| H | H | —OCH₂CH₂O— | | Cl | CH₃ | C(=O)C₂H₅ | C₂H₅ | H | 2 | 1 |
| H | H | —OCH₂CH₂O— | | CH₃ | CH₃ | SO₂CH₂Cl | CH₃ | H | 2 | 1 |
| H | H | —OCH₂CH₂O— | | CH₃ | H | SO₂CH₂Cl | CH₃ | H | 2 | 1 |
| H | H | —OCH₂CH₂O— | | H | H | SO₂CH₂Cl | CH₃ | H | 2 | 1 |
| H | H | —OCH₂CH₂O— | | Cl | Cl | SO₂CH₂Cl | CH₃ | H | 2 | 1 |
| H | H | —OCH₂CH₂O— | | Cl | H | SO₂CH₂Cl | CH₃ | H | 2 | 1 |
| H | H | —OCH₂CH₂O— | | Cl | CH₃ | SO₂CH₂Cl | CH₃ | H | 2 | 1 |
| H | H | —OCH₂CH₂O— | | CH₃ | CH₃ | SO₂-n-C₃H₇ | CH₃ | H | 2 | 1 |
| H | H | —OCH₂CH₂O— | | CH₃ | H | SO₂-n-C₃H₇ | CH₃ | H | 2 | 1 |
| H | H | —OCH₂CH₂O— | | H | H | SO₂-n-C₃H₇ | CH₃ | H | 2 | 1 |
| H | H | —OCH₂CH₂O— | | Cl | Cl | SO₂-n-C₃H₇ | CH₃ | H | 2 | 1 |
| H | H | —OCH₂CH₂O— | | Cl | H | SO₂-n-C₃H₇ | CH₃ | H | 2 | 1 |
| H | H | —OCH₂CH₂O— | | Cl | CH₃ | SO₂-n-C₃H₇ | CH₃ | H | 2 | 1 |
| H | H | —OCH₂CH₂O— | | CH₃ | CH₃ | SO₂-p-tolyl | CH₃ | H | 2 | 1 |
| H | H | —OCH₂CH₂O— | | CH₃ | H | SO₂-p-tolyl | CH₃ | H | 2 | 1 |
| H | H | —OCH₂CH₂O— | | H | H | SO₂-p-tolyl | CH₃ | H | 2 | 1 |

TABLE 3-continued

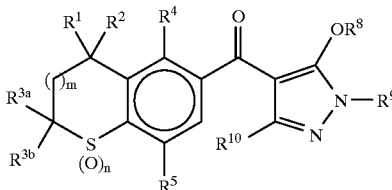

| R³ᵃ | R³ᵇ | R¹ | R² | R⁴ | R⁵ | R⁸ | R⁹ | R¹⁰ | n | m |
|---|---|---|---|---|---|---|---|---|---|---|
| H | H | —OCH₂CH₂O— | | Cl | Cl | SO₂-p-tolyl | CH₃ | H | 2 | 1 |
| H | H | —OCH₂CH₂O— | | Cl | H | SO₂-p-tolyl | CH₃ | H | 2 | 1 |
| H | H | —OCH₂CH₂O— | | Cl | CH₃ | SO₂-p-tolyl | CH₃ | H | 2 | 1 |
| H | H | —OCH₂CH₂O— | | CH₃ | CH₃ | SO₂CH₃ | C₂H₅ | H | 0 | 1 |
| H | H | —OCH₂CH₂O— | | CH₃ | CH₃ | SO₂C₂H₅ | C₂H₅ | H | 0 | 1 |
| H | H | —OCH₂CH₂O— | | CH₃ | CH₃ | SO₂-n-C₃H₇ | C₂H₅ | H | 0 | 1 |
| H | H | —OCH₂CH₂O— | | CH₃ | CH₃ | SO₂-n-C₄H₉ | C₂H₅ | H | 0 | 1 |
| H | H | —OCH₂CH₂O— | | CH₃ | CH₃ | SO₂-p-tolyl | C₂H₅ | H | 0 | 1 |
| H | H | —OCH₂CH₂O— | | CH₃ | CH₃ | SO₂-p-NO₂C₆H₄ | C₂H₅ | H | 0 | 1 |
| H | H | —OCH₂CH₂O— | | CH₃ | CH₃ | SO₂-p-ClC₆H₄ | C₂H₅ | H | 0 | 1 |
| H | H | —OCH₂CH₂O— | | CH₃ | CH₃ | C(=O)CH₃ | C₂H₅ | H | 0 | 1 |
| H | H | —OCH₂CH₂O— | | CH₃ | CH₃ | C(=O)C₂H₅ | C₂H₅ | H | 0 | 1 |
| H | H | —OCH₂CH₂O— | | CH₃ | CH₃ | SO₂CH₃ | C₂H₅ | H | 1 | 1 |
| H | H | —OCH₂CH₂O— | | CH₃ | CH₃ | SO₂C₂H₅ | C₂H₅ | H | 1 | 1 |
| H | H | —OCH₂CH₂O— | | CH₃ | CH₃ | SO₂-n-C₃H₇ | C₂H₅ | H | 1 | 1 |
| H | H | —OCH₂CH₂O— | | CH₃ | CH₃ | SO₂-n-C₄H₉ | C₂H₅ | H | 1 | 1 |
| H | H | —OCH₂CH₂O— | | CH₃ | CH₃ | SO₂-p-tolyl | C₂H₅ | H | 1 | 1 |
| H | H | —OCH₂CH₂O— | | CH₃ | CH₃ | SO₂-p-NO₂C₆H₄ | C₂H₅ | H | 1 | 1 |
| H | H | —OCH₂CH₂O— | | CH₃ | CH₃ | SO₂-p-ClC₆H₄ | C₂H₅ | H | 1 | 1 |
| H | H | —OCH₂CH₂O— | | CH₃ | CH₃ | C(=O)CH₃ | C₂H₅ | H | 1 | 1 |
| H | H | —OCH₂CH₂O— | | CH₃ | CH₃ | C(=O)C₂H₅ | C₂H₅ | H | 1 | 1 |
| H | H | —OCH₂CH₂O— | | CH₃ | CH₃ | SO₂CH₃ | C₂H₅ | H | 2 | 2 |
| H | H | —OCH₂CH₂O— | | CH₃ | CH₃ | SO₂C₂H₅ | C₂H₅ | H | 2 | 2 |
| H | H | —OCH₂CH₂O— | | CH₃ | CH₃ | SO₂-n-C₃H₇ | C₂H₅ | H | 2 | 2 |
| H | H | —OCH₂CH₂O— | | CH₃ | CH₃ | SO₂-n-C₄H₉ | C₂H₅ | H | 2 | 2 |
| H | H | —OCH₂CH₂O— | | CH₃ | CH₃ | SO₂-p-tolyl | C₂H₅ | H | 2 | 2 |
| H | H | —OCH₂CH₂O— | | CH₃ | CH₃ | SO₂-p-NO₂C₆H₄ | C₂H₅ | H | 2 | 2 |
| H | H | —OCH₂CH₂O— | | CH₃ | CH₃ | SO₂-p-ClC₆H₄ | C₂H₅ | H | 2 | 2 |
| H | H | —OCH₂CH₂O— | | CH₃ | CH₃ | C(=O)CH₃ | C₂H₅ | H | 2 | 2 |
| H | H | —OCH₂CH₂O— | | CH₃ | CH₃ | C(=O)C₂H₅ | C₂H₅ | H | 2 | 2 |

TABLE 4

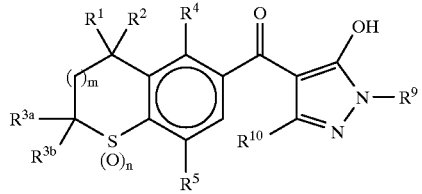

| R³ᵃ | R³ᵇ | R¹ | R² | R⁴ | R⁵ | n | m | R⁹ | R¹⁰ |
|---|---|---|---|---|---|---|---|---|---|
| H | H | —OCH₂CH₂O— | | CH₃ | CH₃ | 2 | 1 | CH₃ | H |
| H | H | —OCH₂CH₂O— | | CH₃ | H | 2 | 1 | CH₃ | H |
| H | H | —OCH₂CH₂O— | | H | H | 2 | 1 | CH₃ | H |
| H | H | —OCH₂CH₂O— | | Cl | Cl | 2 | 1 | CH₃ | H |
| H | H | —OCH₂CH₂O— | | Cl | H | 2 | 1 | CH₃ | H |
| H | H | —OCH₂CH₂O— | | Cl | CH₃ | 2 | 1 | CH₃ | H |
| CH₃ | CH₃ | —OCH₂CH₂O— | | CH₃ | CH₃ | 2 | 1 | CH₃ | H |
| CH₃ | CH₃ | —OCH₂CH₂O— | | CH₃ | H | 2 | 1 | CH₃ | H |
| CH₃ | CH₃ | —OCH₂CH₂O— | | H | H | 2 | 1 | CH₃ | H |
| CH₃ | CH₃ | —OCH₂CH₂O— | | Cl | Cl | 2 | 1 | CH₃ | H |
| CH₃ | CH₃ | —OCH₂CH₂O— | | Cl | H | 2 | 1 | CH₃ | H |
| CH₃ | CH₃ | —OCH₂CH₂O— | | Cl | CH₃ | 2 | 1 | CH₃ | H |
| CH₃ | H | —OCH₂CH₂O— | | CH₃ | CH₃ | 2 | 1 | CH₃ | H |
| CH₃ | H | —OCH₂CH₂O— | | CH₃ | H | 2 | 1 | CH₃ | H |
| CH₃ | H | —OCH₂CH₂O— | | H | H | 2 | 1 | CH₃ | H |
| CH₃ | H | —CCH₂CH₂O— | | Cl | Cl | 2 | 1 | CH₃ | H |
| CH₃ | H | —OCH₂CH₂O— | | Cl | H | 2 | 1 | CH₃ | H |
| CH₃ | H | —OCH₂CH₂O— | | Cl | CH₃ | 2 | 1 | CH₃ | H |
| H | H | —OCH₂CH₂O— | | CH₃ | CH₃ | 2 | 1 | CH₃ | CH₃ |

TABLE 4-continued

| R$^{3a}$ | R$^{3b}$ | R$^1$ R$^2$ | R$^4$ | R$^5$ | n | m | R$^9$ | R$^{10}$ |
|---|---|---|---|---|---|---|---|---|
| H | H | —OCH$_2$CH$_2$O— | CH$_3$ | H | 2 | 1 | CH$_3$ | CH$_3$ |
| H | H | —OCH$_2$CH$_2$O— | H | H | 2 | 1 | CH$_3$ | CH$_3$ |
| H | H | —OCH$_2$CH$_2$O— | Cl | Cl | 2 | 1 | CH$_3$ | CH$_3$ |
| H | H | —OCH$_2$CH$_2$O— | Cl | H | 2 | 1 | CH$_3$ | CH$_3$ |
| H | H | —OCH$_2$CH$_2$O— | Cl | CH$_3$ | 2 | 1 | CH$_3$ | CH$_3$ |
| CH$_3$ | CH$_3$ | —OCH$_2$CH$_2$O— | CH$_3$ | CH$_3$ | 2 | 1 | CH$_3$ | CH$_3$ |
| CH$_3$ | CH$_3$ | —OCH$_2$CH$_2$O— | CH$_3$ | H | 2 | 1 | CH$_3$ | CH$_3$ |
| CH$_3$ | CH$_3$ | —OCH$_2$CH$_2$O— | H | H | 2 | 1 | CH$_3$ | CH$_3$ |
| CH$_3$ | CH$_3$ | —OCH$_2$CH$_2$O— | Cl | Cl | 2 | 1 | CH$_3$ | CH$_3$ |
| CH$_3$ | CH$_3$ | —OCH$_2$CH$_2$O— | Cl | H | 2 | 1 | CH$_3$ | CH$_3$ |
| CH$_3$ | CH$_3$ | —OCH$_2$CH$_2$O— | Cl | CH$_3$ | 2 | 1 | CH$_3$ | CH$_3$ |
| CH$_3$ | H | —OCH$_2$CH$_2$O— | CH$_3$ | CH$_3$ | 2 | 1 | CH$_3$ | CH$_3$ |
| CH$_3$ | H | —OCH$_2$CH$_2$O— | CH$_3$ | H | 2 | 1 | CH$_3$ | CH$_3$ |
| CH$_3$ | H | —OCH$_2$CH$_2$O— | H | H | 2 | 1 | CH$_3$ | CH$_3$ |
| CH$_3$ | H | —OCH$_2$CH$_2$O— | Cl | Cl | 2 | 1 | CH$_3$ | CH$_3$ |
| CH$_3$ | H | —OCH$_2$CH$_2$O— | Cl | H | 2 | 1 | CH$_3$ | CH$_3$ |
| CH$_3$ | H | —OCH$_2$CH$_2$O— | Cl | CH$_3$ | 2 | 1 | CH$_3$ | CH$_3$ |
| H | H | —OCH$_2$CH$_2$O— | CH$_3$ | CH$_3$ | 2 | 1 | C$_2$H$_5$ | CH$_3$ |
| H | H | —OCH$_2$CH$_2$O— | CH$_3$ | H | 2 | 1 | C$_2$H$_5$ | CH$_3$ |
| H | H | —OCH$_2$CH$_2$O— | H | H | 2 | 1 | C$_2$H$_5$ | CH$_3$ |
| H | H | —CCH$_2$CH$_2$O— | Cl | Cl | 2 | 1 | C$_2$H$_5$ | CH$_3$ |
| H | H | —OCH$_2$CH$_2$O— | Cl | H | 2 | 1 | C$_2$H$_5$ | CH$_3$ |
| H | H | —OCH$_2$CH$_2$O— | Cl | CH$_3$ | 2 | 1 | C$_2$H$_5$ | CH$_3$ |
| CH$_3$ | CH$_3$ | —OCH$_2$CH$_2$O— | CH$_3$ | CH$_3$ | 2 | 1 | C$_2$H$_5$ | CH$_3$ |
| CH$_3$ | CH$_3$ | —OCH$_2$CH$_2$O— | CH$_3$ | H | 2 | 1 | C$_2$H$_5$ | CH$_3$ |
| CH$_3$ | CH$_3$ | —OCH$_2$CH$_2$O— | H | H | 2 | 1 | C$_2$H$_5$ | CH$_3$ |
| CH$_3$ | CH$_3$ | —OCH$_2$CH$_2$O— | Cl | Cl | 2 | 1 | C$_2$H$_5$ | CH$_3$ |
| CH$_3$ | CH$_3$ | —OCH$_2$CH$_2$O— | Cl | H | 2 | 1 | C$_2$H$_5$ | CH$_3$ |
| H | H | —OCH$_2$CH$_2$O— | CH$_3$ | CH$_3$ | 2 | 1 | CH$_3$ | OCH$_3$ |
| H | H | —OCH$_2$CH$_2$O— | CH$_3$ | H | 2 | 1 | CH$_3$ | OCH$_3$ |
| H | H | —OCH$_2$CH$_2$O— | H | H | 2 | 1 | CH$_3$ | OCH$_3$ |
| H | H | —OCH$_2$CH$_2$O— | Cl | Cl | 2 | 1 | CH$_3$ | OCH$_3$ |
| H | H | —OCH$_2$CH$_2$O— | Cl | H | 2 | 1 | CH$_3$ | OCH$_3$ |
| H | H | —OCH$_2$CH$_2$O— | Cl | CH$_3$ | 2 | 1 | CH$_3$ | 0CH$_3$ |
| CH$_3$ | CH$_3$ | —OCH$_2$CH$_2$O— | CH$_3$ | CH$_3$ | 2 | 1 | CH$_3$ | OCH$_3$ |
| CH$_3$ | CH$_3$ | —OCH$_2$CH$_2$O— | CH$_3$ | H | 2 | 1 | CH$_3$ | 0CH$_3$ |
| CH$_3$ | CH$_3$ | —OCH$_2$CH$_2$O— | H | H | 2 | 1 | CH$_3$ | OCH$_3$ |
| CH$_3$ | CH$_3$ | —OCH$_2$CH$_2$O— | Cl | Cl | 2 | 1 | CH$_3$ | OCH$_3$ |
| CH$_3$ | CH$_3$ | —OCH$_2$CH$_2$O— | Cl | H | 2 | 1 | CH$_3$ | OCH$_3$ |
| CH$_3$ | CH$_3$ | —OCH$_2$CH$_2$O— | Cl | CH$_3$ | 2 | 1 | CH$_3$ | OCH$_3$ |
| CH$_3$ | H | —OCH$_2$CH$_2$O— | CH$_3$ | CH$_3$ | 2 | 1 | CH$_3$ | OCH$_3$ |
| CH$_3$ | H | —OCH$_2$CH$_2$O— | CH$_3$ | H | 2 | 1 | CH$_3$ | OCH$_3$ |
| CH$_3$ | H | —OCH$_2$CH$_2$O— | H | H | 2 | 1 | CH$_3$ | OCH$_3$ |
| CH$_3$ | H | —OCH$_2$CH$_2$O— | Cl | Cl | 2 | 1 | CH$_3$ | OCH$_3$ |
| CH$_3$ | H | —OCH$_2$CH$_2$O— | Cl | H | 2 | 1 | CH$_3$ | OCH$_3$ |
| CH$_3$ | H | —OCH$_2$CH$_2$O— | Cl | CH$_3$ | 2 | 1 | CH$_3$ | OCH$_3$ |
| H | H | —OCH$_2$CH$_2$O— | CH$_3$ | CH$_3$ | 2 | 1 | C$_2$H$_5$ | OCH$_3$ |
| H | H | —OCH$_2$CH$_2$O— | CH$_3$ | H | 2 | 1 | C$_2$H$_5$ | OCH$_3$ |
| H | H | —OCH$_2$CH$_2$O— | H | H | 2 | 1 | C$_2$H$_5$ | OCH$_3$ |
| H | H | —OCH$_2$CH$_2$O— | Cl | Cl | 2 | 1 | C$_2$H$_5$ | OCH$_3$ |
| H | H | —OCH$_2$CH$_2$O— | Cl | H | 2 | 1 | C$_2$H$_5$ | OCH$_3$ |
| H | H | —OCH$_2$CH$_2$O— | Cl | CH$_3$ | 2 | 1 | C$_2$H$_5$ | OCH$_3$ |
| CH$_3$ | CH$_3$ | —OCH$_2$CH$_2$O— | CH$_3$ | CH$_3$ | 2 | 1 | C$_2$H$_5$ | OCH$_3$ |
| CH$_3$ | CH$_3$ | —OCH$_2$CH$_2$O— | CH$_3$ | H | 2 | 1 | C$_2$H$_5$ | OCH$_3$ |
| CH$_3$ | CH$_3$ | —OCH$_2$CH$_2$O— | H | H | 2 | 1 | C$_2$H$_5$ | OCH$_3$ |
| CH$_3$ | CH$_3$ | —OCH$_2$CH$_2$O— | Cl | Cl | 2 | 1 | C$_2$H$_5$ | OCH$_3$ |
| CH$_3$ | CH$_3$ | —OCH$_2$CH$_2$O— | Cl | H | 2 | 1 | C$_2$H$_5$ | OCH$_3$ |
| H | H | —OCH$_2$CH$_2$O— | CH$_3$ | CH$_3$ | 2 | 1 | CH$_3$ | CF$_3$ |
| H | H | —OCH$_2$CH$_2$O— | CH$_3$ | H | 2 | 1 | CH$_3$ | CF$_3$ |
| H | H | —OCH$_2$CH$_2$O— | H | H | 2 | 1 | CH$_3$ | CF$_3$ |
| H | H | —OCH$_2$CH$_2$O— | Cl | Cl | 2 | 1 | CH$_3$ | CF$_3$ |
| H | H | —OCH$_2$CH$_2$O— | Cl | H | 2 | 1 | CH$_3$ | CF$_3$ |
| H | H | —OCH$_2$CH$_2$O— | Cl | CH$_3$ | 2 | 1 | CH$_3$ | CF$_3$ |
| CH$_3$ | CH$_3$ | —OCH$_2$CH$_2$O— | CH$_3$ | CH$_3$ | 2 | 1 | CH$_3$ | CF$_3$ |
| CH$_3$ | CH$_3$ | —OCH$_2$CH$_2$O | CH$_3$ | H | 2 | 1 | CH$_3$ | CF$_3$ |
| CH$_3$ | CH$_3$ | —OCH$_2$CH$_2$O— | H | H | 2 | 1 | CH$_3$ | CF$_3$ |
| CH$_3$ | CH$_3$ | —OCH$_2$CH$_2$O— | Cl | Cl | 2 | 1 | CH$_3$ | CF$_3$ |

TABLE 4-continued

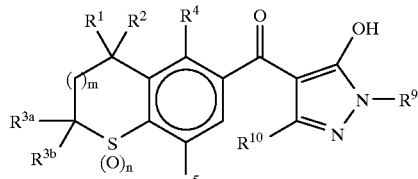

| R³ᵃ | R³ᵇ | R¹ R² | R⁴ | R⁵ | n | m | R⁹ | R¹⁰ |
|---|---|---|---|---|---|---|---|---|
| CH₃ | CH₃ | —OCH₂CH₂O— | Cl | H | 2 | 1 | CH₃ | CF₃ |
| CH₃ | CH₃ | —OCH₂CH₂O— | Cl | CH₃ | 2 | 1 | CH₃ | CF₃ |
| CH₃ | H | —OCH₂CH₂O— | CH₃ | CH₃ | 2 | 1 | CH₃ | CF₃ |
| CH₃ | H | —OCH₂CH₂O— | CH₃ | H | 2 | 1 | CH₃ | CF₃ |
| CH₃ | H | —OCH₂CH₂O— | H | H | 2 | 1 | CH₃ | CF₃ |
| CH₃ | H | —OCH₂CH₂O— | Cl | Cl | 2 | 1 | CH₃ | CF₃ |
| CH₃ | H | —OCH₂CH₂O— | Cl | H | 2 | 1 | CH₃ | CF₃ |
| CH₃ | H | —OCH₂CH₂O— | Cl | CH₃ | 2 | 1 | CH₃ | CF₃ |
| H | H | —OCH₂CH₂O— | CH₃ | CH₃ | 2 | 1 | C₂H₅ | CF₃ |
| H | H | —OCH₂CH₂O— | CH₃ | H | 2 | 1 | C₂H₅ | CF₃ |
| H | H | —OCH₂CH₂O— | H | H | 2 | 1 | C₂H₅ | CF₃ |
| H | H | —OCH₂CH₂O— | Cl | Cl | 2 | 1 | C₂H₅ | CF₃ |
| H | H | —OCH₂CH₂O— | Cl | H | 2 | 1 | C₂H₅ | CF₃ |
| H | H | —OCH₂CH₂O— | Cl | CH₃ | 2 | 1 | C₂H₅ | CF₃ |
| CH₃ | CH₃ | —OCH₂CH₂O— | CH₃ | CH₃ | 2 | 1 | C₂H₅ | CF₃ |
| CH₃ | CH₃ | —OCH₂CH₂O— | CH₃ | H | 2 | 1 | C₂H₅ | CF₃ |
| CH₃ | CH₃ | —OCH₂CH₂O— | H | H | 2 | 1 | C₂H₅ | CF₃ |
| CH₃ | CH₃ | —OCH₂CH₂O— | Cl | Cl | 2 | 1 | C₂H₅ | CF₃ |
| CH₃ | CH₃ | —OCH₂CH₂O— | Cl | H | 2 | 1 | C₂H₅ | CF₃ |
| CH₃ | CH₃ | —OCH₂CH₂O— | Cl | CH₃ | 2 | 1 | CH₂CH₂CH₃ | CH₃ |
| CH₃ | H | —OCH₂CH₂O— | CH₃ | CH₃ | 2 | 1 | CH₂CH₂CH₃ | CH₃ |
| CH₃ | H | —OCH₂CH₂O— | CH₃ | H | 2 | 1 | CH₂CH₂CH₃ | CH₃ |
| CH₃ | H | —OCH₂CH₂O— | H | H | 2 | 1 | CH₂CH₂CH₃ | CH₃ |
| CH₃ | H | —OCH₂CH₂O— | Cl | Cl | 2 | 1 | CH₂CH₂CH₃ | CH₃ |
| CH₃ | H | —OCH₂CH₂O— | Cl | H | 2 | 1 | CH₂CH₂CH₃ | CH₃ |
| CH₃ | H | —OCH₂CH₂O— | Cl | CH₃ | 2 | 1 | CH₂CH₂CH₃ | CH₃ |
| H | H | —OCH₂CH₂O— | CH₃ | CH₃ | 2 | 1 | CH₂CH₂CH₃ | CH₃ |
| H | H | —OCH₂CH₂O— | CH₃ | H | 2 | 1 | CH₂CH₂CH₃ | CH₃ |
| H | H | —OCH₂CH₂O— | Cl | Cl | 2 | 1 | CH₂CH₂CH₃ | CH₃ |
| H | H | —OCH₂CH₂O— | Cl | H | 2 | 1 | CH₂CH₂CH₃ | CH₃ |
| H | H | —OCH₂CH₂O— | Cl | CH₃ | 2 | 1 | CH₂CH₂CH₃ | CH₃ |
| CH₃ | CH₃ | —OCH₂CH₂O— | CH₃ | CH₃ | 2 | 1 | CH₂CH₂CH₃ | CH₃ |
| CH₃ | CH₃ | —OCH₂CH₂O— | CH₃ | H | 2 | 1 | CH₂CH₂CH₃ | CH₃ |
| CH₃ | CH₃ | —OCH₂CH₂O— | H | H | 2 | 1 | CH₂CH₂CH₃ | CH₃ |
| CH₃ | CH₃ | —OCH₂CH₂O— | Cl | Cl | 2 | 1 | CH₂CH₂CH₃ | CH₃ |
| CH₃ | CH₃ | —OCH₂CH₂O— | Cl | H | 2 | 1 | CH₂CH₂CH₃ | CH₃ |
| CH₃ | CH₃ | —OCH₂CH₂O— | Cl | CH₃ | 2 | 1 | CH₂CH₂CH₃ | CH₃ |
| CH₃ | H | —OCH₂CH₂O— | CH₃ | CH₃ | 2 | 1 | CH₂CH₂CH₃ | CH₃ |
| CH₃ | H | —OCH₂CH₂O— | CH₃ | H | 2 | 1 | CH₂CH₂CH₃ | CH₃ |
| CH₃ | H | —OCH₂CH₂O— | H | H | 2 | 1 | CH₂CH₂CH₃ | CH₃ |
| CH₃ | H | —OCH₂CH₂O— | Cl | Cl | 2 | 1 | CH₂CH₂CH₃ | CH₃ |
| CH₃ | H | —OCH₂CH₂O— | Cl | H | 2 | 1 | CH₂CH₂CH₃ | CH₃ |
| CH₃ | H | —OCH₂CH₂O— | Cl | CH₃ | 2 | 1 | CH₂CH₂CH₃ | CH₃ |
| H | H | —OCH₂CH₂O— | CH₃ | CH₃ | 2 | 1 | CH(CH₃)₂ | H |
| H | H | —OCH₂CH₂O— | CH₃ | H | 2 | 1 | CH(CH₃)₂ | H |
| H | H | —OCH₂CH₂O— | H | H | 2 | 1 | CH(CH₃)₂ | H |
| H | H | —OCH₂CH₂O— | Cl | Cl | 2 | 1 | CH(CH₃)₂ | H |
| H | H | —OCH₂CH₂O— | Cl | H | 2 | 1 | CH(CH₃)₂ | H |
| H | H | —OCH₂CH₂O— | Cl | CH₃ | 2 | 1 | CH(CH₃)₂ | H |
| CH₃ | CH₃ | —OCH₂CH₂O— | CH₃ | CH₃ | 2 | 1 | CH(CH₃)₂ | H |
| CH₃ | CH₃ | —OCH₂CH₂O— | CH₃ | H | 2 | 1 | CH(CH₃)₂ | H |
| CH₃ | CH₃ | —OCH₂CH₂O— | H | H | 2 | 1 | CH(CH₃)₂ | H |
| CH₃ | CH₃ | —OCH₂CH₂O— | Cl | Cl | 2 | 1 | CH(CH₃)₂ | H |
| CH₃ | CH₃ | —OCH₂CH₂O— | Cl | H | 2 | 1 | CH(CH₃)₂ | H |
| CH₃ | CH₃ | —OCH₂CH₂O— | Cl | CH₃ | 2 | 1 | CH(CH₃)₂ | H |
| CH₃ | H | —OCH₂CH₂O— | CH₃ | CH₃ | 2 | 1 | CH(CH₃)₂ | H |
| CH₃ | H | —OCH₂CH₂O— | CH₃ | H | 2 | 1 | CH(CH₃)₂ | H |
| CH₃ | H | —OCH₂CH₂O— | H | H | 2 | 1 | CH(CH₃)₂ | H |
| CH₃ | H | —OCH₂CH₂O— | Cl | Cl | 2 | 1 | CH(CH₃)₂ | H |
| CH₃ | H | —OCH₂CH₂O— | Cl | H | 2 | 1 | CH(CH₃)₂ | H |
| CH₃ | H | —OCH₂CH₂O— | Cl | CH₃ | 2 | 1 | CH(CH₃)₂ | H |
| H | H | —OCH₂CH₂O— | CH₃ | CH₃ | 2 | 1 | C₆H₅ | H |
| H | H | —OCH₂CH₂O— | CH₃ | H | 2 | 1 | C₆H₅ | H |
| H | H | —OCH₂CH₂O— | H | H | 2 | 1 | C₆H₅ | H |
| H | H | —OCH₂CH₂O— | Cl | Cl | 2 | 1 | C₆H₅ | H |
| H | H | —OCH₂CH₂O— | Cl | H | 2 | 1 | C₆H₅ | H |
| H | H | —OCH₂CH₂O— | Cl | CH₃ | 2 | 1 | C₆H₅ | H |

TABLE 4-continued

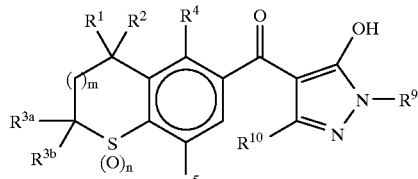

| $R^{3a}$ | $R^{3b}$ | $R^1$  $R^2$ | $R^4$ | $R^5$ | n | m | $R^9$ | $R^{10}$ |
|---|---|---|---|---|---|---|---|---|
| CH₃ | CH₃ | —OCH₂CH₂O— | CH₃ | CH₃ | 2 | 1 | C₆H₅ | H |
| CH₃ | CH₃ | —OCH₂CH₂O— | CH₃ | H | 2 | 1 | C₆H₅ | H |
| CH₃ | CH₃ | —OCH₂CH₂O— | H | H | 2 | 1 | C₆H₅ | H |
| CH₃ | CH₃ | —OCH₂CH₂O— | Cl | Cl | 2 | 1 | C₆H₅ | H |
| CH₃ | CH₃ | —OCH₂CH₂O— | Cl | H | 2 | 1 | C₆H₅ | H |
| CH₃ | CH₃ | —OCH₂CH₂O— | Cl | CH₃ | 2 | 1 | C₆H₅ | H |
| CH₃ | H | —OCH₂CH₂O— | CH₃ | CH₃ | 2 | 1 | C₆H₅ | H |
| CH₃ | H | —OCH₂CH₂O— | CH₃ | H | 2 | 1 | C₆H₅ | H |
| CH₃ | H | —CCH₂CH₂O— | H | H | 2 | 1 | C₆H₅ | H |
| CH₃ | H | —OCH₂CH₂O— | Cl | Cl | 2 | 1 | C₆H₅ | H |
| CH₃ | H | —OCH₂CH₂O— | Cl | H | 2 | 1 | C₆H₅ | H |
| CH₃ | H | —OCH₂CH₂O— | Cl | CH₃ | 2 | 1 | C₆H₅ | H |
| H | H | —CCH₂CH₂O— | CH₃ | CH₃ | 2 | 1 | C₆H₅ | CH₃ |
| H | H | —OCH₂CH₂O— | CH₃ | H | 2 | 1 | C₆H₅ | CH₃ |
| H | H | —OCH₂CH₂O— | H | H | 2 | 1 | C₆H₅ | CH₃ |
| H | H | —OCH₂CH₂O— | Cl | Cl | 2 | 1 | C₆H₅ | CH₃ |
| H | H | —OCH₂CH₂O— | Cl | H | 2 | 1 | C₆H₅ | CH₃ |
| H | H | —OCH₂CH₂O— | Cl | CH₃ | 2 | 1 | C₆H₅ | CH₃ |
| CH₃ | CH₃ | —OCH₂CH₂O— | CH₃ | CH₃ | 2 | 1 | C₆H₅ | CH₃ |
| CH₃ | CH₃ | —OCH₂CH₂O— | CH₃ | H | 2 | 1 | C₆H₅ | CH₃ |
| CH₃ | CH₃ | —OCH₂CH₂O— | H | H | 2 | 1 | C₆H₅ | CH₃ |
| CH₃ | CH₃ | —OCH₂CH₂O— | Cl | Cl | 2 | 1 | C₆H₅ | CH₃ |
| CH₃ | CH₃ | —OCH₂CH₂O— | Cl | H | 2 | 1 | C₆H₅ | CH₃ |
| CH₃ | CH₃ | —OCH₂CH₂O— | Cl | CH₃ | 2 | 1 | C₆H₅ | CH₃ |
| CH₃ | H | —OCH₂CH₂O— | CH₃ | CH₃ | 2 | 1 | C₆H₅ | CH₃ |
| CH₃ | H | —OCH₂CH₂O— | CH₃ | H | 2 | 1 | C₆H₅ | CH₃ |
| CH₃ | H | —OCH₂CH₂O— | H | H | 2 | 1 | C₆H₅ | CH₃ |
| CH₃ | H | —OCH₂CH₂O— | Cl | Cl | 2 | 1 | C₆H₅ | CH₃ |
| CH₃ | H | —OCH₂CH₂O— | Cl | H | 2 | 1 | C₆H₅ | CH₃ |
| CH₃ | H | —OCH₂CH₂O— | Cl | CH₃ | 2 | 1 | C₆H₅ | CH₃ |
| H | H | —CH₂CH₂CH₂O— | CH₃ | CH₃ | 2 | 1 | CH₃ | H |
| H | H | —CH₂CH₂CH₂O— | CH₃ | H | 2 | 1 | CH₃ | H |
| H | H | —CH₂CH₂CH₂O— | H | H | 2 | 1 | CH₃ | H |
| H | H | —CH₂CH₂CH₂O— | Cl | Cl | 2 | 1 | CH₃ | H |
| H | H | —CH₂CH₂CH₂O— | Cl | H | 2 | 1 | CH₃ | H |
| H | H | —CH₂CH₂CH₂O— | Cl | CH₃ | 2 | 1 | CH₃ | H |
| CH₃ | CH₃ | —CH₂CH₂CH₂O— | CH₃ | CH₃ | 2 | 1 | CH₃ | H |
| CH₃ | CH₃ | —CH₂CH₂CH₂O— | CH₃ | H | 2 | 1 | CH₃ | H |
| CH₃ | CH₃ | —CH₂CH₂CH₂O— | H | H | 2 | 1 | CH₃ | H |
| CH₃ | CH₃ | —CH₂CH₂CH₂O— | Cl | Cl | 2 | 1 | CH₃ | H |
| CH₃ | CH₃ | —CH₂CH₂CH₂O— | Cl | H | 2 | 1 | CH₃ | H |
| CH₃ | CH₃ | —CH₂CH₂CH₂O— | Cl | CH₃ | 2 | 1 | CH₃ | H |
| CH₃ | H | —CH₂CH₂CH₂O— | CH₃ | CH₃ | 2 | 1 | CH₃ | H |
| CH₃ | H | —CH₂CH₂CH₂O— | CH₃ | H | 2 | 1 | CH₃ | H |
| CH₃ | H | —CH₂CH₂CH₂O— | H | H | 2 | 1 | CH₃ | H |
| CH₃ | H | —CH₂CH₂CH₂O— | Cl | Cl | 2 | 1 | CH₃ | H |
| CH₃ | H | —CH₂CH₂CH₂O— | Cl | H | 2 | 1 | CH₃ | H |
| CH₃ | H | —CH₂CH₂CH₂O— | Cl | CH₃ | 2 | 1 | CH₃ | H |
| H | H | —OCH₂CH₂CH₂O— | CH₃ | CH₃ | 2 | 1 | CH₃ | Cl |
| H | H | —OCH₂CH₂CH₂O— | CH₃ | H | 2 | 1 | CH₃ | Cl |
| H | H | —OCH₂CH₂CH₂O— | H | H | 2 | 1 | CH₃ | Cl |
| H | H | —OCH₂CH₂CH₂O— | Cl | Cl | 2 | 1 | CH₃ | Cl |
| H | H | —OCH₂CH₂CH₂O— | Cl | H | 2 | 1 | CH₃ | Cl |
| H | H | —OCH₂CH₂CH₂O— | Cl | CH₃ | 2 | 1 | CH₃ | Cl |
| CH₃ | CH₃ | —OCH₂CH₂CH₂O— | CH₃ | CH₃ | 2 | 1 | CH₃ | Cl |
| CH₃ | CH₃ | —OCH₂CH₂CH₂O— | CH₃ | H | 2 | 1 | CH₃ | Cl |
| CH₃ | CH₃ | —OCH₂CH₂CH₂O— | H | H | 2 | 1 | CH₃ | Cl |
| CH₃ | CH₃ | —OCH₂CH₂CH₂O— | Cl | Cl | 2 | 1 | CH₃ | Cl |
| CH₃ | CH₃ | —OCH₂CH₂CH₂O— | Cl | H | 2 | 1 | CH₃ | Cl |
| CH₃ | CH₃ | —OCH₂CH₂CH₂O— | Cl | CH₃ | 2 | 1 | CH₃ | Cl |
| CH₃ | H | —OCH₂CH₂CH₂O— | CH₃ | CH₃ | 2 | 1 | CH₃ | Cl |
| CH₃ | H | —OCH₂CH₂CH₂O— | CH₃ | H | 2 | 1 | CH₃ | Cl |
| CH₃ | H | —OCH₂CH₂CH₂O— | H | H | 2 | 1 | CH₃ | Cl |
| CH₃ | H | —OCH₂CH₂CH₂O— | Cl | Cl | 2 | 1 | CH₃ | Cl |
| CH₃ | H | —OCH₂CH₂CH₂O— | Cl | H | 2 | 1 | CH₃ | Cl |
| CH₃ | H | —OCH₂CH₂CH₂O— | Cl | CH₃ | 2 | 1 | CH₃ | Cl |
| H | H | —OCH₂CH₂O— | CH₃ | CH₃ | 2 | 1 | C₂H₅ | Cl |

TABLE 4-continued

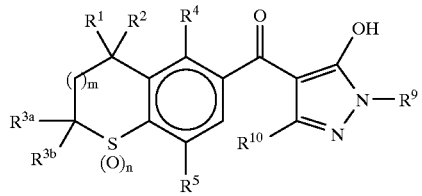

| $R^{3a}$ | $R^{3b}$ | $R^1$ $R^2$ | $R^4$ | $R^5$ | n | m | $R^9$ | $R^{10}$ |
|---|---|---|---|---|---|---|---|---|
| H | H | —OCH$_2$CH$_2$O— | CH$_3$ | H | 2 | 1 | C$_2$H$_5$ | Cl |
| H | H | —OCH$_2$CH$_2$O— | H | H | 2 | 1 | C$_2$H$_5$ | Cl |
| H | H | —OCH$_2$CH$_2$O— | Cl | Cl | 2 | 1 | C$_2$H$_5$ | Cl |
| H | H | —OCH$_2$CH$_2$O— | Cl | H | 2 | 1 | C$_2$H$_5$ | Cl |
| H | H | —OCH$_2$CH$_2$O— | Cl | CH$_3$ | 2 | 1 | C$_2$H$_5$ | Cl |
| CH$_3$ | CH$_3$ | —OCH$_2$CH$_2$O— | CH$_3$ | CH$_3$ | 2 | 1 | C$_2$H$_5$ | Cl |
| CH$_3$ | CH$_3$ | —OCH$_2$CH$_2$O— | CH$_3$ | H | 2 | 1 | C$_2$H$_5$ | Cl |
| CH$_3$ | CH$_3$ | —OCH$_2$CH$_2$O— | H | H | 2 | 1 | C$_2$H$_5$ | Cl |
| CH$_3$ | CH$_3$ | —OCH$_2$CH$_2$O— | Cl | Cl | 2 | 1 | C$_2$H$_5$ | Cl |
| CH$_3$ | CH$_3$ | —OCH$_2$CH$_2$O— | Cl | H | 2 | 1 | C$_2$H$_5$ | Cl |
| CH$_3$ | CH$_3$ | —OCH$_2$CH$_2$O— | Cl | CH$_3$ | 2 | 1 | C$_2$H$_5$ | Cl |
| CH$_3$ | H | —OCH$_2$CH$_2$O— | CH$_3$ | CH$_3$ | 2 | 1 | C$_2$H$_5$ | Cl |
| CH$_3$ | H | —OCH$_2$CH$_2$O— | CH$_3$ | H | 2 | 1 | C$_2$H$_5$ | Cl |
| CH$_3$ | H | —OCH$_2$CH$_2$O— | H | H | 2 | 1 | C$_2$H$_5$ | Cl |
| CH$_3$ | H | —OCH$_2$CH$_2$O— | Cl | Cl | 2 | 1 | C$_2$H$_5$ | Cl |
| CH$_3$ | H | —OCH$_2$CH$_2$CH$_2$O— | Cl | H | 2 | 1 | C$_2$H$_5$ | Cl |
| CH$_3$ | H | —OCH$_2$CH$_2$O— | Cl | CH$_3$ | 2 | 1 | C$_2$H$_5$ | Cl |
| H | H | —OCH$_2$CH$_2$CH$_2$O— | CH$_3$ | CH$_3$ | 2 | 1 | CH$_3$ | H |
| H | H | OCH$_2$CH$_2$CH$_2$O | CH$_3$ | H | 2 | 1 | CH$_3$ | H |
| H | H | OCH$_2$CH$_2$CH$_2$O | H | H | 2 | 1 | CH$_3$ | H |
| H | H | OCH$_2$CH$_2$CH$_2$O | Cl | Cl | 2 | 1 | CH$_3$ | H |
| H | H | OCH$_2$CH$_2$CH$_2$O | Cl | H | 2 | 1 | CH$_3$ | H |
| H | H | OCH$_2$CH$_2$CH$_2$O | Cl | CH$_3$ | 2 | 1 | CH$_3$ | H |
| CH$_3$ | CH$_3$ | OCH$_2$CH$_2$CH$_2$O | CH$_3$ | CH$_3$ | 2 | 1 | CH$_3$ | H |
| CH$_3$ | CH$_3$ | OCH$_2$CH$_2$CH$_2$O | CH$_3$ | H | 2 | 1 | CH$_3$ | H |
| CH$_3$ | CH$_3$ | OCH$_2$CH$_2$CH$_2$O | H | H | 2 | 1 | CH$_3$ | H |
| CH$_3$ | CH$_3$ | OCH$_2$CH$_2$CH$_2$O | Cl | Cl | 2 | 1 | CH$_3$ | H |
| CH$_3$ | CH$_3$ | OCH$_2$CH$_2$CH$_2$O | Cl | H | 2 | 1 | CH$_3$ | H |
| CH$_3$ | CH$_3$ | OCH$_2$CH$_2$CH$_2$O | Cl | CH$_3$ | 2 | 1 | CH$_3$ | H |
| CH$_3$ | H | OCH$_2$CH$_2$CH$_2$O | CH$_3$ | CH$_3$ | 2 | 1 | CH$_3$ | H |
| CH$_3$ | H | OCH$_2$CH$_2$CH$_2$O | CH$_3$ | H | 2 | 1 | CH$_3$ | H |
| CH$_3$ | H | OCH$_2$CH$_2$CH$_2$O | H | H | 2 | 1 | CH$_3$ | H |
| CH$_3$ | H | OCH$_2$CH$_2$CH$_2$O | Cl | Cl | 2 | 1 | CH$_3$ | H |
| CH$_3$ | H | OCH$_2$CH$_2$CH$_2$O | Cl | H | 2 | 1 | CH$_3$ | H |
| CH$_3$ | H | OCH$_2$CH$_2$CH$_2$O | Cl | CH$_3$ | 2 | 1 | CH$_3$ | H |
| H | H | —SCH$_2$CH$_2$S— | CH$_3$ | CH$_3$ | 2 | 1 | CH$_3$ | H |
| H | H | —SCH$_2$CH$_2$S— | CH$_3$ | CH$_3$ | 0 | 1 | CH$_3$ | H |
| H | H | —SCH$_2$CH$_2$S— | CH$_3$ | H | 2 | 1 | CH$_3$ | H |
| H | H | —SCH$_2$CH$_2$S— | H | H | 2 | 1 | CH$_3$ | H |
| H | H | —SCH$_2$CH$_2$S— | Cl | Cl | 2 | 1 | CH$_3$ | H |
| H | H | —SCH$_2$CH$_2$S— | Cl | H | 2 | 1 | CH$_3$ | H |
| H | H | —SCH$_2$CH$_2$S— | Cl | CH$_3$ | 2 | 1 | CH$_3$ | H |
| CH$_3$ | CH$_3$ | —SCH$_2$CH$_2$S— | CH$_3$ | CH$_3$ | 2 | 1 | CH$_3$ | H |
| CH$_3$ | CH$_3$ | —SCH$_2$CH$_2$S— | CH$_3$ | H | 2 | 1 | CH$_3$ | H |
| CH$_3$ | CH$_3$ | —SCH$_2$CH$_2$S— | H | H | 2 | 1 | CH$_3$ | H |
| CH$_3$ | CH$_3$ | —SCH$_2$CH$_2$S— | Cl | Cl | 2 | 1 | CH$_3$ | H |
| CH$_3$ | CH$_3$ | —SCH$_2$CH$_2$S— | Cl | H | 2 | 1 | CH$_3$ | H |
| CH$_3$ | CH$_3$ | —SCH$_2$CH$_2$S— | Cl | CH$_3$ | 2 | 1 | CH$_3$ | H |
| CH$_3$ | H | —SCH$_2$CH$_2$S— | CH$_3$ | CH$_3$ | 2 | 1 | CH$_3$ | H |
| CH$_3$ | H | —SCH$_2$CH$_2$S— | CH$_3$ | H | 2 | 1 | CH$_3$ | H |
| CH$_3$ | H | —SCH$_2$CH$_2$S— | H | H | 2 | 1 | CH$_3$ | H |
| CH$_3$ | H | —SCH$_2$CH$_2$S— | Cl | Cl | 2 | 1 | CH$_3$ | H |
| CH$_3$ | H | —SCH$_2$CH$_2$S— | Cl | H | 2 | 1 | CH$_3$ | H |
| CH$_3$ | H | —SCH$_2$CH$_2$S— | Cl | CH$_3$ | 2 | 1 | CH$_3$ | H |
| H | H | —SCH$_2$CH$_2$O— | CH$_3$ | CH$_3$ | 2 | 1 | CH$_3$ | H |
| H | H | —SCH$_2$CH$_2$O— | CH$_3$ | CH$_3$ | 0 | 1 | CH$_3$ | H |
| H | H | —SCH$_2$CH$_2$O— | CH$_3$ | H | 2 | 1 | CH$_3$ | H |
| H | H | —SCH$_2$CH$_2$O— | H | H | 2 | 1 | CH$_3$ | H |
| H | H | —SCH$_2$CH$_2$O— | Cl | Cl | 2 | 1 | CH$_3$ | H |
| H | H | —SCH$_2$CH$_2$O— | Cl | H | 2 | 1 | CH$_3$ | H |
| H | H | —SCH$_2$CH$_2$O— | Cl | CH$_3$ | 2 | 1 | CH$_3$ | H |
| CH$_3$ | CH$_3$ | —SCH$_2$CH$_2$O— | CH$_3$ | CH$_3$ | 2 | 1 | CH$_3$ | H |
| CH$_3$ | CH$_3$ | —SCH$_2$CH$_2$O— | CH$_3$ | H | 2 | 1 | CH$_3$ | H |
| CH$_3$ | CH$_3$ | —SCH$_2$CH$_2$O— | H | H | 2 | 1 | CH$_3$ | H |
| CH$_3$ | CH$_3$ | —SCH$_2$CH$_2$O— | Cl | Cl | 2 | 1 | CH$_3$ | H |
| CH$_3$ | CH$_3$ | —SCH$_2$CH$_2$O— | Cl | H | 2 | 1 | CH$_3$ | H |
| CH$_3$ | CH$_3$ | —SCH$_2$CH$_2$O— | Cl | CH$_3$ | 2 | 1 | CH$_3$ | H |

TABLE 4-continued

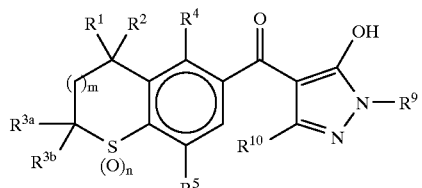

| R³ᵃ | R³ᵇ | R¹ R² | R⁴ | R⁵ | n | m | R⁹ | R¹⁰ |
|---|---|---|---|---|---|---|---|---|
| CH₃ | H | —SCH₂CH₂O— | CH₃ | CH₃ | 2 | 1 | CH₃ | H |
| CH₃ | H | —SCH₂CH₂O— | CH₃ | H | 2 | 1 | CH₃ | H |
| CH₃ | H | —SCH₂CH₂O— | H | H | 2 | 1 | CH₃ | H |
| CH₃ | H | —SCH₂CH₂O— | Cl | Cl | 2 | 1 | CH₃ | H |
| CH₃ | H | —SCH₂CH₂O— | Cl | H | 2 | 1 | CH₃ | H |
| CH₃ | H | —SCH₂CH₂O— | Cl | CH₃ | 2 | 1 | CH₃ | H |
| H | H | —SCH₂CH₂CH₂S— | CH₃ | CH₃ | 2 | 1 | CH₃ | H |
| H | H | —SCH₂CH₂CH₂S— | CH₃ | H | 2 | 1 | CH₃ | H |
| H | H | —SCH₂CH₂CH₂S— | H | H | 2 | 1 | CH₃ | H |
| H | H | —SCH₂CH₂CH₂S— | Cl | Cl | 2 | 1 | CH₃ | H |
| H | H | —SCH₂CH₂CH₂S— | Cl | H | 2 | 1 | CH₃ | H |
| H | H | —SCH₂CH₂CH₂S— | Cl | CH₃ | 2 | 1 | CH₃ | H |
| CH₃ | CH₃ | —SCH₂CH₂CH₂S— | CH₃ | CH₃ | 2 | 1 | CH₃ | H |
| CH₃ | CH₃ | —SCH₂CH₂CH₂S— | CH₃ | H | 2 | 1 | CH₃ | H |
| CH₃ | CH₃ | —SCH₂CH₂CH₂S— | H | H | 2 | 1 | CH₃ | H |
| CH₃ | CH₃ | —SCH₂CH₂CH₂S— | Cl | Cl | 2 | 1 | CH₃ | H |
| CH₃ | CH₃ | —SCH₂CH₂CH₂S— | Cl | H | 2 | 1 | CH₃ | H |
| CH₃ | CH₃ | —SCH₂CH₂CH₂S— | Cl | CH₃ | 2 | 1 | CH₃ | H |
| CH₃ | H | —SCH₂CH₂CH₂S— | CH₃ | CH₃ | 2 | 1 | CH₃ | H |
| CH₃ | H | —SCH₂CH₂CH₂S— | CH₃ | H | 2 | 1 | CH₃ | H |
| CH₃ | H | —SCH₂CH₂CH₂S— | H | H | 2 | 1 | CH₃ | H |
| CH₃ | H | —SCH₂CH₂CH₂S— | Cl | Cl | 2 | 1 | CH₃ | H |
| CH₃ | H | —SCH₂CH₂CH₂S— | Cl | H | 2 | 1 | CH₃ | H |
| CH₃ | H | —SCH₂CH₂CH₂S— | Cl | CH₃ | 2 | 1 | CH₃ | H |
| H | H | oxo | CH₃ | CH₃ | 2 | 1 | CH₃ | H |
| H | H | oxo | CH₃ | H | 2 | 1 | CH₃ | H |
| H | H | oxo | Cl | Cl | 2 | 1 | CH₃ | H |
| H | H | oxo | Cl | H | 2 | 1 | CH₃ | H |
| H | H | oxo | Cl | CH₃ | 2 | 1 | CH₃ | H |
| CH₃ | CH₃ | oxo | CH₃ | CH₃ | 2 | 1 | CH₃ | H |
| CH₃ | CH₃ | oxo | CH₃ | H | 2 | 1 | CH₃ | H |
| CH₃ | CH₃ | oxo | H | H | 2 | 1 | CH₃ | H |
| CH₃ | CH₃ | oxo | Cl | Cl | 2 | 1 | CH₃ | H |
| CH₃ | CH₃ | oxo | Cl | H | 2 | 1 | CH₃ | H |
| CH₃ | CH₃ | oxo | Cl | CH₃ | 2 | 1 | CH₃ | H |
| CH₃ | H | oxo | CH₃ | CH₃ | 2 | 1 | CH₃ | H |
| CH₃ | H | oxo | CH₃ | H | 2 | 1 | CH₃ | H |
| CH₃ | H | oxo | H | H | 2 | 1 | CH₃ | H |
| CH₃ | H | oxo | Cl | Cl | 2 | 1 | CH₃ | H |
| CH₃ | H | oxo | Cl | H | 2 | 1 | CH₃ | H |
| CH₃ | H | oxo | Cl | CH₃ | 2 | 1 | CH₃ | H |
| H | H | oxo | CH₃ | CH₃ | 1 | 1 | CH₃ | H |
| H | H | oxo | CH₃ | H | 1 | 1 | CH₃ | H |
| H | H | oxo | H | H | 1 | 1 | CH₃ | H |
| H | H | oxo | Cl | Cl | 1 | 1 | CH₃ | H |
| H | H | oxo | Cl | H | 1 | 1 | CH₃ | H |
| H | H | oxo | Cl | CH₃ | 1 | 1 | CH₃ | H |
| CH₃ | CH₃ | oxo | CH₃ | CH₃ | 1 | 1 | CH₃ | H |
| CH₃ | CH₃ | oxo | CH₃ | H | 1 | 1 | CH₃ | H |
| CH₃ | CH₃ | oxo | H | H | 1 | 1 | CH₃ | H |
| CH₃ | CH₃ | oxo | Cl | Cl | 1 | 1 | CH₃ | H |
| CH₃ | CH₃ | oxo | Cl | H | 1 | 1 | CH₃ | H |
| CH₃ | CH₃ | oxo | Cl | CH₃ | 1 | 1 | CH₃ | H |
| CH₃ | H | oxo | CH₃ | CH₃ | 1 | 1 | CH₃ | H |
| CH₃ | H | oxo | CH₃ | H | 1 | 1 | CH₃ | H |
| CH₃ | H | oxo | H | H | 1 | 1 | CH₃ | H |
| CH₃ | H | oxo | Cl | Cl | 1 | 1 | CH₃ | H |
| CH₃ | H | oxo | Cl | H | 1 | 1 | CH₃ | H |
| CH₃ | H | oxo | Cl | CH₃ | 1 | 1 | CH₃ | H |

TABLE 5

| R³ᵃ | R³ᵇ | R¹ R² | R⁴ | R⁵ | R⁶ | n | m |
|---|---|---|---|---|---|---|---|
| H | H | —OCH₂CH₂O— | CH₃ | CH₃ | OH | 2 | 1 |
| H | H | —OCH₂CH₂O— | CH₃ | H | OH | 2 | 1 |
| H | H | —OCH₂CH₂O— | H | H | OH | 2 | 1 |
| H | H | —OCH₂CH₂O— | Cl | Cl | OH | 2 | 1 |
| H | H | —OCH₂CH₂O— | Cl | H | OH | 2 | 1 |
| H | H | —OCH₂CH₂O— | Cl | CH₃ | OH | 2 | 1 |
| H | H | —OCH₂CH₂O— | NO₂ | H | OH | 2 | 1 |
| CH₃ | CH₃ | —OCH₂CH₂O— | CH₃ | CH₃ | OH | 2 | 1 |
| CH₃ | CH₃ | —OCH₂CH₂O— | CH₃ | H | OH | 2 | 1 |
| CH₃ | CH₃ | —OCH₂CH₂O— | H | H | OH | 2 | 1 |
| CH₃ | CH₃ | —OCH₂CH₂O— | Cl | Cl | OH | 2 | 1 |
| CH₃ | CH₃ | —OCH₂CH₂O— | Cl | H | OH | 2 | 1 |
| CH₃ | CH₃ | —OCH₂CH₂O— | Cl | CH₃ | OH | 2 | 1 |
| CH₃ | H | —OCH₂CH₂O— | CH₃ | CH₃ | OH | 2 | 1 |
| CH₃ | H | —OCH₂CH₂O— | CH₃ | H | OH | 2 | 1 |
| CH₃ | H | —OCH₂CH₂O— | H | H | OH | 2 | 1 |
| CH₃ | H | —OCH₂CH₂O— | Cl | Cl | OH | 2 | 1 |
| CH₃ | H | —OCH₂CH₂O— | Cl | H | OH | 2 | 1 |
| CH₃ | H | —OCH₂CH₂O— | Cl | CH₃ | OH | 2 | 1 |
| H | H | —OCH₂CH(CH₃)O— | CH₃ | CH₃ | OH | 2 | 1 |
| H | H | —OCH₂CH(CH₃)O— | CH₃ | H | OH | 2 | 1 |
| H | H | —OCH₂CH(CH₃)O— | H | H | OH | 2 | 1 |
| H | H | —OCH₂CH(CH₃)O— | Cl | Cl | OH | 2 | 1 |
| H | H | —OCH₂CH(CH₃)O— | Cl | H | OH | 2 | 1 |
| H | H | —OCH₂CH(CH₃)O— | Cl | CH₃ | OH | 2 | 1 |
| CH₃ | CH₃ | —OCH₂CH(CH₃)O— | CH₃ | CH₃ | OH | 2 | 1 |
| CH₃ | CH₃ | —OCH₂CH(CH₃)O— | CH₃ | H | OH | 2 | 1 |
| CH₃ | CH₃ | —OCH₂CH(CH₃)O— | H | H | OH | 2 | 1 |
| CH₃ | CH₃ | —OCH₂CH(CH₃)O— | Cl | Cl | OH | 2 | 1 |
| CH₃ | CH₃ | —OCH₂CH(CH₃)O— | Cl | H | OH | 2 | 1 |
| CH₃ | CH₃ | —OCH₂CH(CH₃)O— | Cl | CH₃ | OH | 2 | 1 |
| CH₃ | H | —OCH₂CH(CH₃)O— | CH₃ | CH₃ | OH | 2 | 1 |
| CH₃ | H | —OCH₂CH(CH₃)O— | CH₃ | H | OH | 2 | 1 |
| CH₃ | H | —OCH₂CH(CH₃)O— | H | H | OH | 2 | 1 |
| CH₃ | H | —OCH₂CH(CH₃)O— | Cl | Cl | OH | 2 | 1 |
| CH₃ | H | —OCH₂CH(CH₃)O— | Cl | H | OH | 2 | 1 |
| CH₃ | H | —OCH₂CH(CH₃)O— | Cl | CH₃ | OH | 2 | 1 |
| H | H | —OCH₂CH₂CH₂O— | CH₃ | CH₃ | OH | 2 | 1 |
| H | H | —OCH₂CH₂CH₂O— | CH₃ | H | OH | 2 | 1 |
| H | H | —OCH₂CH₂CH₂O— | H | H | OH | 2 | 1 |
| H | H | —OCH₂CH₂CH₂O— | Cl | Cl | OH | 2 | 1 |
| H | H | —OCH₂CH₂CH₂O— | Cl | H | OH | 2 | 1 |
| H | H | —OCH₂CH₂CH₂O— | Cl | CH₃ | OH | 2 | 1 |
| CH₃ | CH₃ | —OCH₂CH₂CH₂O— | CH₃ | CH₃ | OH | 2 | 1 |
| CH₃ | CH₃ | —OCH₂CH₂CH₂O— | CH₃ | H | OH | 2 | 1 |
| CH₃ | CH₃ | —OCH₂CH₂CH₂O— | H | H | OH | 2 | 1 |
| CH₃ | CH₃ | —OCH₂CH₂CH₂O— | Cl | Cl | OH | 2 | 1 |
| CH₃ | CH₃ | —OCH₂CH₂CH₂O— | Cl | H | OH | 2 | 1 |
| CH₃ | CH₃ | —OCH₂CH₂CH₂O— | Cl | CH₃ | OH | 2 | 1 |
| CH₃ | H | —OCH₂CH₂CH₂O— | CH₃ | CH₃ | OH | 2 | 1 |
| CH₃ | H | —OCH₂CH₂CH₂O— | CH₃ | H | OH | 2 | 1 |
| CH₃ | H | —OCH₂CH₂CH₂O— | H | H | OH | 2 | 1 |
| CH₃ | H | —OCH₂CH₂CH₂O— | Cl | Cl | OH | 2 | 1 |
| CH₃ | H | —OCH₂CH₂CH₂O— | Cl | H | OH | 2 | 1 |
| CH₃ | H | —OCH₂CH₂CH₂O— | Cl | CH₃ | OH | 2 | 1 |
| H | H | —CH₂CH₂CH₂O— | CH₃ | CH₃ | OH | 2 | 1 |
| H | H | —CH₂CH₂CH₂O— | CH₃ | H | OH | 2 | 1 |
| H | H | —CH₂CH₂CH₂O— | H | H | OH | 2 | 1 |
| H | H | —CH₂CH₂CH₂O— | Cl | Cl | OH | 2 | 1 |
| H | H | —CH₂CH₂CH₂O— | Cl | H | OH | 2 | 1 |
| H | H | —CH₂CH₂CH₂O— | Cl | CH₃ | OH | 2 | 1 |
| CH₃ | CH₃ | —CH₂CH₂CH₂O— | CH₃ | CH₃ | OH | 2 | 1 |
| CH₃ | CH₃ | —CH₂CH₂CH₂O— | CH₃ | H | OH | 2 | 1 |
| CH₃ | CH₃ | —CH₂CH₂CH₂O— | H | H | OH | 2 | 1 |
| CH₃ | CH₃ | —CH₂CH₂CH₂O— | Cl | Cl | OH | 2 | 1 |
| CH₃ | CH₃ | —CH₂CH₂CH₂O— | Cl | H | OH | 2 | 1 |
| CH₃ | CH₃ | —CH₂CH₂CH₂O— | Cl | CH₃ | OH | 2 | 1 |
| CH₃ | H | —CH₂CH₂CH₂O— | CH₃ | CH₃ | OH | 2 | 1 |
| CH₃ | H | —CH₂CH₂CH₂O— | CH₃ | H | OH | 2 | 1 |
| CH₃ | H | —CH₂CH₂CH₂O— | H | H | OH | 2 | 1 |
| CH₃ | H | —CH₂CH₂CH₂O— | Cl | Cl | OH | 2 | 1 |
| CH₃ | H | —CH₂CH₂CH₂O— | Cl | H | OH | 2 | 1 |
| CH₃ | H | —CH₂CH₂CH₂O— | Cl | CH₃ | OH | 2 | 1 |
| H | H | —OCH₂CH₂O— | CH₃ | CH₃ | OH | 2 | 0 |
| H | H | —OCH₂CH₂O— | CH₃ | H | OH | 2 | 0 |
| H | H | —OCH₂CH₂O— | H | H | OH | 2 | 0 |
| H | H | —OCH₂CH₂O— | Cl | Cl | OH | 2 | 0 |
| H | H | —OCH₂CH₂O— | Cl | H | OH | 2 | 0 |
| H | H | —OCH₂CH₂O— | Cl | CH₃ | OH | 2 | 0 |
| CH₃ | CH₃ | —OCH₂CH₂O— | CH₃ | CH₃ | OH | 2 | 0 |
| CH₃ | CH₃ | —OCH₂CH₂O— | CH₃ | H | OH | 2 | 0 |
| CH₃ | CH₃ | —OCH₂CH₂O— | H | H | OH | 2 | 0 |
| CH₃ | CH₃ | —OCH₂CH₂O— | Cl | Cl | OH | 2 | 0 |
| CH₃ | CH₃ | —OCH₂CH₂O— | Cl | H | OH | 2 | 0 |
| CH₃ | CH₃ | —OCH₂CH₂O— | Cl | CH₃ | OH | 2 | 0 |
| CH₃ | H | —OCH₂CH₂O— | CH₃ | CH₃ | OH | 2 | 0 |
| CH₃ | H | —OCH₂CH₂O— | CH₃ | H | OH | 2 | 0 |
| CH₃ | H | —OCH₂CH₂O— | H | H | OH | 2 | 0 |
| CH₃ | H | —OCH₂CH₂O— | Cl | Cl | OH | 2 | 0 |
| CH₃ | H | —OCH₂CH₂O— | Cl | H | OH | 2 | 0 |
| CH₃ | H | —OCH₂CH₂O— | Cl | CH₃ | OH | 2 | 0 |
| H | H | —OCH₂CH(CH₃)O— | CH₃ | CH₃ | OH | 2 | 0 |
| H | H | —OCH₂CH(CH₃)O— | CH₃ | H | OH | 2 | 0 |
| H | H | —OCH₂CH(CH₃)O— | H | H | OH | 2 | 0 |
| H | H | —OCH₂CH(CH₃)O— | Cl | Cl | OH | 2 | 0 |
| H | H | —OCH₂CH(CH₃)O— | Cl | H | OH | 2 | 0 |
| H | H | —OCH₂CH(CH₃)O— | Cl | CH₃ | OH | 2 | 0 |
| CH₃ | CH₃ | —OCH₂CH(CH₃)O— | CH₃ | CH₃ | OH | 2 | 0 |
| CH₃ | CH₃ | —OCH₂CH(CH₃)O— | CH₃ | H | OH | 2 | 0 |
| CH₃ | CH₃ | —OCH₂CH(CH₃)O— | H | H | OH | 2 | 0 |
| CH₃ | CH₃ | —OCH₂CH(CH₃)O— | Cl | Cl | OH | 2 | 0 |
| CH₃ | CH₃ | —OCH₂CH(CH₃)O— | Cl | H | OH | 2 | 0 |
| CH₃ | CH₃ | —OCH₂CH(CH₃)O— | Cl | CH₃ | OH | 2 | 0 |
| CH₃ | H | —OCH₂CH(CH₃)O— | CH₃ | CH₃ | OH | 2 | 0 |
| CH₃ | H | —OCH₂CH(CH₃)O— | CH₃ | H | OH | 2 | 0 |
| CH₃ | H | —OCH₂CH(CH₃)O— | H | H | OH | 2 | 0 |
| CH₃ | H | —OCH₂CH(CH₃)O— | Cl | Cl | OH | 2 | 0 |
| CH₃ | H | —OCH₂CH(CH₃)O— | Cl | H | OH | 2 | 0 |
| CH₃ | H | —OCH₂CH(CH₃)O— | Cl | CH₃ | OH | 2 | 0 |
| H | H | —OCH₂CH₂CH₂O— | CH₃ | CH₃ | OH | 2 | 0 |
| H | H | —OCH₂CH₂CH₂O— | CH₃ | H | OH | 2 | 0 |
| H | H | —OCH₂CH₂CH₂O— | H | H | OH | 2 | 0 |
| H | H | —OCH₂CH₂CH₂O— | Cl | Cl | OH | 2 | 0 |
| H | H | —OCH₂CH₂CH₂O— | Cl | H | OH | 2 | 0 |
| H | H | —OCH₂CH₂CH₂O— | Cl | CH₃ | OH | 2 | 0 |
| CH₃ | CH₃ | —OCH₂CH₂CH₂O— | CH₃ | CH₃ | OH | 2 | 0 |
| CH₃ | CH₃ | —OCH₂CH₂CH₂O— | CH₃ | H | OH | 2 | 0 |
| CH₃ | CH₃ | —OCH₂CH₂CH₂O— | H | H | OH | 2 | 0 |
| CH₃ | CH₃ | —OCH₂CH₂CH₂O— | Cl | Cl | OH | 2 | 0 |
| CH₃ | CH₃ | —OCH₂CH₂CH₂O— | Cl | H | OH | 2 | 0 |
| CH₃ | CH₃ | —OCH₂CH₂CH₂O— | Cl | CH₃ | OH | 2 | 0 |
| CH₃ | H | —OCH₂CH₂CH₂O— | CH₃ | CH₃ | OH | 2 | 0 |
| CH₃ | H | —OCH₂CH₂CH₂O— | CH₃ | H | OH | 2 | 0 |
| CH₃ | H | —OCH₂CH₂CH₂O— | H | H | OH | 2 | 0 |
| CH₃ | H | —OCH₂CH₂CH₂O— | Cl | Cl | OH | 2 | 0 |
| CH₃ | H | —OCH₂CH₂CH₂O— | Cl | H | OH | 2 | 0 |
| CH₃ | H | —OCH₂CH₂CH₂O— | Cl | CH₃ | OH | 2 | 0 |
| H | H | —SCH₂CH₂S— | CH₃ | CH₃ | OH | 2 | 0 |
| H | H | —SCH₂CH₂S— | CH₃ | CH₃ | OH | 0 | 0 |
| H | H | —SCH₂CH₂S— | CH₃ | H | OH | 2 | 0 |
| H | H | —SCH₂CH₂S— | H | H | OH | 2 | 0 |
| H | H | —SCH₂CH₂S— | Cl | Cl | OH | 2 | 0 |

TABLE 5-continued

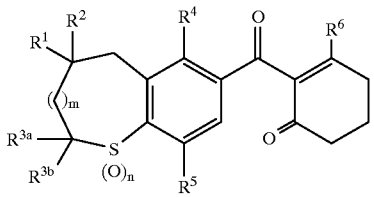

| R³ᵃ | R³ᵇ | R¹ R² | R⁴ | R⁵ | R⁶ | n | m |
|---|---|---|---|---|---|---|---|
| H | H | —SCH₂CH₂S— | Cl | H | OH | 2 | 0 |
| H | H | —SCH₂CH₂S— | Cl | CH₃ | OH | 2 | 0 |
| H | H | —SCH₂CH₂S— | NO₂ | H | OH | 2 | 0 |
| CH₃ | CH₃ | —SCH₂CH₂S— | CH₃ | CH₃ | OH | 2 | 0 |
| CH₃ | CH₃ | —SCH₂CH₂S— | CH₃ | H | OH | 2 | 0 |
| CH₃ | CH₃ | —SCH₂CH₂S— | H | H | OH | 2 | 0 |
| CH₃ | CH₃ | —SCH₂CH₂S— | Cl | Cl | OH | 2 | 0 |
| CH₃ | CH₃ | —SCH₂CH₂S— | Cl | H | OH | 2 | 0 |
| CH₃ | CH₃ | —SCH₂CH₂S— | Cl | CH₃ | OH | 2 | 0 |
| CH₃ | H | —SCH₂CH₂S— | CH₃ | CH₃ | OH | 2 | 0 |
| CH₃ | H | —SCH₂CH₂S— | CH₃ | H | OH | 2 | 0 |
| CH₃ | H | —SCH₂CH₂S— | H | H | OH | 2 | 0 |
| CH₃ | H | —SCH₂CH₂S— | Cl | Cl | OH | 2 | 0 |
| CH₃ | H | —SCH₂CH₂S— | Cl | H | OH | 2 | 0 |
| CH₃ | H | —SCH₂CH₂S— | Cl | CH₃ | OH | 2 | 0 |
| H | H | —SCH₂CH₂O— | CH₃ | CH₃ | OH | 2 | 0 |
| H | H | —SCH₂CH₂O— | CH₃ | CH₃ | OH | 0 | 0 |
| H | H | oxo | CH₃ | CH₃ | OH | 2 | 1 |
| H | H | oxo | CH₃ | H | OH | 2 | 1 |
| H | H | oxo | H | H | OH | 2 | 1 |
| H | H | oxo | Cl | Cl | OH | 2 | 1 |
| H | H | oxo | Cl | H | OH | 2 | 1 |
| H | H | oxo | Cl | CH₃ | OH | 2 | 1 |
| H | H | oxo | NO₂ | H | OH | 2 | 1 |
| CH₃ | CH₃ | oxo | CH₃ | CH₃ | OH | 2 | 1 |
| CH₃ | CH₃ | oxo | CH₃ | H | OH | 2 | 1 |
| CH₃ | CH₃ | oxo | H | H | OH | 2 | 1 |
| CH₃ | CH₃ | oxo | Cl | Cl | OH | 2 | 1 |
| CH₃ | CH₃ | oxo | Cl | H | OH | 2 | 1 |
| CH₃ | CH₃ | oxo | Cl | CH₃ | OH | 2 | 1 |
| CH₃ | H | oxo | CH₃ | CH₃ | OH | 2 | 1 |
| CH₃ | H | oxo | CH₃ | H | OH | 2 | 1 |
| CH₃ | H | oxo | H | H | OH | 2 | 1 |
| CH₃ | H | oxo | Cl | Cl | OH | 2 | 1 |
| CH₃ | H | oxo | Cl | H | OH | 2 | 1 |
| CH₃ | H | oxo | Cl | CH₃ | OH | 2 | 1 |
| H | H | oxo | CH₃ | CH₃ | OH | 1 | 1 |
| H | H | oxo | CH₃ | H | OH | 1 | 1 |
| H | H | oxo | H | H | OH | 1 | 1 |
| H | H | oxo | Cl | Cl | OH | 1 | 1 |
| H | H | oxo | Cl | H | OH | 1 | 1 |
| H | H | oxo | Cl | CH₃ | OH | 1 | 1 |
| CH₃ | CH₃ | oxo | CH₃ | CH₃ | OH | 1 | 1 |
| CH₃ | CH₃ | oxo | CH₃ | H | OH | 1 | 1 |
| CH₃ | CH₃ | oxo | H | H | OH | 1 | 1 |
| CH₃ | CH₃ | oxo | Cl | Cl | OH | 1 | 1 |
| CH₃ | CH₃ | oxo | Cl | H | OH | 1 | 1 |
| CH₃ | CH₃ | oxo | Cl | CH₃ | OH | 1 | 1 |
| CH₃ | H | oxo | CH₃ | CH₃ | OH | 1 | 1 |
| CH₃ | H | oxo | CH₃ | H | OH | 1 | 1 |
| CH₃ | H | oxo | H | H | OH | 1 | 1 |
| CH₃ | H | oxo | Cl | Cl | OH | 1 | 1 |
| CH₃ | H | oxo | Cl | H | OH | 1 | 1 |
| CH₃ | H | oxo | Cl | CH₃ | OH | 1 | 1 |

TABLE 6

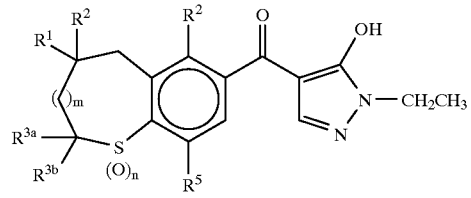

| R³ᵃ | R³ᵇ | R¹ R² | R⁴ | R⁵ | n | m |
|---|---|---|---|---|---|---|
| H | H | —OCH₂CH₂O— | CH₃ | CH₃ | 2 | 1 |
| H | H | —OCH₂CH₂O— | CH₃ | H | 2 | 1 |
| H | H | —OCH₂CH₂O— | H | H | 2 | 1 |
| H | H | —OCH₂CH₂O— | Cl | Cl | 2 | 1 |
| H | H | —OCH₂CH₂O— | Cl | H | 2 | 1 |
| H | H | —OCH₂CH₂O— | Cl | CH₃ | 2 | 1 |
| H | H | —OCH₂CH₂O— | NO₂ | H | 2 | 1 |
| CH₃ | CH₃ | —OCH₂CH₂O— | CH₃ | CH₃ | 2 | 1 |
| CH₃ | CH₃ | —OCH₂CH₂O— | CH₃ | H | 2 | 1 |
| CH₃ | CH₃ | —OCH₂CH₂O— | H | H | 2 | 1 |
| CH₃ | CH₃ | —OCH₂CH₂O— | Cl | Cl | 2 | 1 |
| CH₃ | CH₃ | —CCH₂CH₂O— | Cl | H | 2 | 1 |
| CH₃ | CH₃ | —OCH₂CH₂O— | Cl | CH₃ | 2 | 1 |
| CH₃ | H | —OCH₂CH₂O— | CH₃ | CH₃ | 2 | 1 |
| CH₃ | H | —OCH₂CH₂O— | CH₃ | H | 2 | 1 |
| CH₃ | H | —OCH₂CH₂O— | H | H | 2 | 1 |
| CH₃ | H | —OCH₂CH₂O— | Cl | Cl | 2 | 1 |
| CH₃ | H | —OCH₂CH₂O— | Cl | H | 2 | 1 |
| CH₃ | H | —OCH₂CH₂O— | Cl | CH₃ | 2 | 1 |
| H | H | —OCH₂CH(CH₃)O— | CH₃ | CH₃ | 2 | 1 |
| H | H | —OCH₂CH(CH₃)O— | CH₃ | H | 2 | 1 |
| H | H | —OCH₂CH(CH₃)O— | H | H | 2 | 1 |
| H | H | —OCH₂CH(CH₃)O— | Cl | Cl | 2 | 1 |
| H | H | —OCH₂CH(CH₃)O— | Cl | H | 2 | 1 |
| H | H | —OCH₂CH(CH₃)O— | Cl | CH₃ | 2 | 1 |
| CH₃ | CH₃ | —OCH₂CH(CH₃)O— | CH₃ | CH₃ | 2 | 1 |
| CH₃ | CH₃ | —OCH₂CH(CH₃)O— | CH₃ | H | 2 | 1 |
| CH₃ | CH₃ | —OCH₂CH(CH₃)O— | H | H | 2 | 1 |
| CH₃ | CH₃ | —OCH₂CH(CH₃)O— | Cl | Cl | 2 | 1 |
| CH₃ | CH₃ | —OCH₂CH(CH₃)O— | Cl | H | 2 | 1 |
| CH₃ | CH₃ | —OCH₂CH(CH₃)O— | Cl | CH₃ | 2 | 1 |
| CH₃ | H | —OCH₂CH(CH₃)O— | CH₃ | CH₃ | 2 | 1 |
| CH₃ | H | —OCH₂CH(CH₃)O— | CH₃ | H | 2 | 1 |
| CH₃ | H | —OCH₂CH(CH₃)O— | H | H | 2 | 1 |
| CH₃ | H | —OCH₂CH(CH₃)O— | Cl | Cl | 2 | 1 |
| CH₃ | H | —OCH₂CH(CH₃)O— | Cl | H | 2 | 1 |
| CH₃ | H | —OCH₂CH(CH₃)O— | Cl | CH₃ | 2 | 1 |
| H | H | —OCH₂CH₂CH₂O— | CH₃ | CH₃ | 2 | 1 |
| H | H | —OCH₂CH₂CH₂O— | CH₃ | H | 2 | 1 |
| H | H | —OCH₂CH₂CH₂O— | H | H | 2 | 1 |
| H | H | —OCH₂CH₂CH₂O— | Cl | Cl | 2 | 1 |
| H | H | —OCH₂CH₂CH₂O— | Cl | H | 2 | 1 |
| H | H | —OCH₂CH₂CH₂O— | Cl | CH₃ | 2 | 1 |
| CH₃ | CH₃ | —OCH₂CH₂CH₂O— | CH₃ | CH₃ | 2 | 1 |
| CH₃ | CH₃ | —OCH₂CH₂CH₂O— | CH₃ | H | 2 | 1 |
| CH₃ | CH₃ | —OCH₂CH₂CH₂O— | H | H | 2 | 1 |
| CH₃ | CH₃ | —OCH₂CH₂CH₂O— | Cl | Cl | 2 | 1 |
| CH₃ | CH₃ | —OCH₂CH₂CH₂O— | Cl | H | 2 | 1 |
| CH₃ | CH₃ | —OCH₂CH₂CH₂O— | Cl | CH₃ | 2 | 1 |
| CH₃ | H | —OCH₂CH₂CH₂O— | CH₃ | CH₃ | 2 | 1 |
| CH₃ | H | —OCH₂CH₂CH₂O— | CH₃ | H | 2 | 1 |
| CH₃ | H | —OCH₂CH₂CH₂O— | H | H | 2 | 1 |
| CH₃ | H | —OCH₂CH₂CH₂O— | Cl | Cl | 2 | 1 |
| CH₃ | H | —OCH₂CH₂CH₂O— | Cl | H | 2 | 1 |
| CH₃ | H | —OCH₂CH₂CH₂O— | Cl | CH₃ | 2 | 1 |
| H | H | —CH₂CH₂CH₂O— | CH₃ | CH₃ | 2 | 1 |
| H | H | —CH₂CH₂CH₂O— | CH₃ | H | 2 | 1 |
| H | H | —CH₂CH₂CH₂O— | H | H | 2 | 1 |
| H | H | —CH₂CH₂CH₂O— | Cl | Cl | 2 | 1 |
| H | H | —CH₂CH₂CH₂O— | Cl | H | 2 | 1 |
| H | H | —CH₂CH₂CH₂O— | Cl | CH₃ | 2 | 1 |
| CH₃ | CH₃ | —CH₂CH₂CH₂O— | CH₃ | CH₃ | 2 | 1 |
| CH₃ | CH₃ | —CH₂CH₂CH₂O— | CH₃ | H | 2 | 1 |
| CH₃ | CH₃ | —CH₂CH₂CH₂O— | H | H | 2 | 1 |
| CH₃ | CH₃ | —CH₂CH₂CH₂O— | Cl | Cl | 2 | 1 |
| CH₃ | CH₃ | —CH₂CH₂CH₂O— | Cl | H | 2 | 1 |

TABLE 6-continued

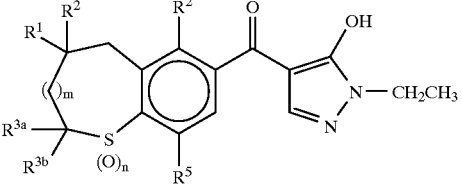

| R3a | R3b | R1 R2 | R4 | R5 | n | m |
|---|---|---|---|---|---|---|
| CH3 | CH3 | —CH2CH2CH2O— | Cl | CH3 | 2 | 1 |
| CH3 | H | —CH2CH2CH2O— | CH3 | CH3 | 2 | 1 |
| CH3 | H | —CH2CH2CH2O— | CH3 | H | 2 | 1 |
| CH3 | H | —CH2CH2CH2O— | H | H | 2 | 1 |
| CH3 | H | —CH2CH2CH2O— | Cl | Cl | 2 | 1 |
| CH3 | H | —CH2CH2CH2O— | Cl | H | 2 | 1 |
| CH3 | H | —CH2CH2CH2O— | Cl | CH3 | 2 | 1 |
| H | H | —OCH2CH2O— | CH3 | CH3 | 2 | 0 |
| H | H | —OCH2CH2O— | CH3 | H | 2 | 0 |
| H | H | —OCH2CH2O— | H | H | 2 | 0 |
| H | H | —OCH2CH2O— | Cl | Cl | 2 | 0 |
| H | H | —OCH2CH2O— | Cl | H | 2 | 0 |
| H | H | —OCH2CH2O— | Cl | CH3 | 2 | 0 |
| CH3 | CH3 | —OCH2CH2O— | CH3 | CH3 | 2 | 0 |
| CH3 | CH3 | —OCH2CH2O— | CH3 | H | 2 | 0 |
| CH3 | CH3 | —OCH2CH2O— | H | H | 2 | 0 |
| CH3 | CH3 | —OCH2CH2O— | Cl | Cl | 2 | 0 |
| CH3 | CH3 | —OCH2CH2O— | Cl | H | 2 | 0 |
| CH3 | CH3 | —OCH2CH2O— | Cl | CH3 | 2 | 0 |
| CH3 | H | —OCH2CH2O— | CH3 | CH3 | 2 | 0 |
| CH3 | H | —OCH2CH2O— | CH3 | H | 2 | 0 |
| CH3 | H | —OCH2CH2O— | H | H | 2 | 0 |
| CH3 | H | —OCH2CH2O— | Cl | Cl | 2 | 0 |
| CH3 | H | —OCH2CH2O— | Cl | H | 2 | 0 |
| CH3 | H | —OCH2CH2O— | Cl | CH3 | 2 | 0 |
| H | H | oxo | NO2 | H | 2 | 1 |
| CH3 | CH3 | oxo | CH3 | CH3 | 2 | 1 |
| CH3 | CH3 | oxo | CH3 | H | 2 | 1 |
| CH3 | CH3 | oxo | H | H | 2 | 1 |
| CH3 | CH3 | oxo | Cl | Cl | 2 | 1 |
| CH3 | CH3 | oxo | Cl | H | 2 | 1 |
| CH3 | CH3 | oxo | Cl | CH3 | 2 | 1 |
| CH3 | H | oxo | CH3 | CH3 | 2 | 1 |

TABLE 6-continued

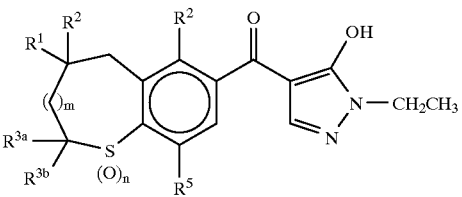

| R3a | R3b | R1 R2 | R4 | R5 | n | m |
|---|---|---|---|---|---|---|
| CH3 | H | oxo | CH3 | H | 2 | 1 |
| CH3 | H | oxo | H | H | 2 | 1 |
| CH3 | H | oxo | Cl | Cl | 2 | 1 |
| CH3 | H | oxo | Cl | H | 2 | 1 |
| CH3 | H | oxo | Cl | CH3 | 2 | 1 |
| H | H | oxo | CH3 | CH3 | 1 | 1 |
| H | H | oxo | CH3 | H | 1 | 1 |
| H | H | oxo | H | H | 1 | 1 |
| H | H | oxo | Cl | Cl | 1 | 1 |
| H | H | oxo | Cl | H | 1 | 1 |
| H | H | oxo | Cl | CH3 | 1 | 1 |
| CH3 | CH3 | oxo | CH3 | CH3 | 1 | 1 |
| CH3 | CH3 | oxo | CH3 | H | 1 | 1 |
| CH3 | CH3 | oxo | H | H | 1 | 1 |
| CH3 | CH3 | oxo | Cl | Cl | 1 | 1 |
| CH3 | CH3 | oxo | Cl | H | 1 | 1 |
| CH3 | CH3 | oxo | Cl | CH3 | 1 | 1 |
| CH3 | H | oxo | CH3 | CH3 | 1 | 1 |
| CH3 | H | oxo | CH3 | H | 1 | 1 |
| CH3 | H | oxo | H | H | 1 | 1 |
| CH3 | H | oxo | Cl | Cl | 1 | 1 |
| CH3 | H | oxo | Cl | H | 1 | 1 |
| CH3 | H | oxo | Cl | CH3 | 1 | 1 |

TABLE 7

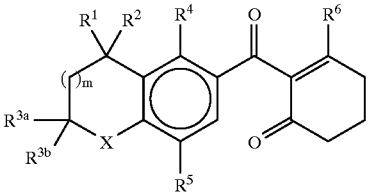

| R3a | R3b | R1 R2 | R4 | R5 | R6 | n | m | X |
|---|---|---|---|---|---|---|---|---|
| H | H | —OCH2CH2O— | CH3 | CH3 | OH | 2 | 1 | NSO2CH3 |
| H | H | —OCH2CH2O— | CH3 | H | OH | 2 | 1 | NSO2CH3 |
| H | H | —OCH2CH2O— | H | H | OH | 2 | 1 | NSO2CH3 |
| H | H | —OCH2CH2O— | Cl | Cl | OH | 2 | 1 | NSO2CH3 |
| H | H | —OCH2CH2O— | Cl | H | OH | 2 | 1 | NSO2CH3 |
| H | H | —OCH2CH2O— | Cl | CH3 | OH | 2 | 1 | NSO2CH3 |
| H | H | —OCH2CH2O— | NO2 | H | OH | 2 | 1 | NSO2CH3 |
| H | H | —OCH2CH2O— | CH3 | CH3 | OH | 2 | 1 | O |
| H | H | —OCH2CH2O— | CH3 | H | OH | 2 | 1 | O |
| H | H | —OCH2CH2O— | H | H | OH | 2 | 1 | O |
| H | H | —OCH2CH2O— | Cl | Cl | OH | 2 | 1 | O |
| H | H | —OCH2CH2O— | Cl | H | OH | 2 | 1 | O |
| H | H | —OCH2CH2O— | Cl | CH3 | OH | 2 | 1 | O |
| H | H | —OCH2CH2O— | CH3 | CH3 | OH | 2 | 1 | NH |

TABLE 7-continued

| R$^{3a}$ | R$^{3b}$ | R$^1$ R$^2$ | R$^4$ | R$^5$ | R$^6$ | n | m | X |
|---|---|---|---|---|---|---|---|---|
| H | H | —OCH$_2$CH$_2$O— | CH$_3$ | H | OH | 2 | 1 | NH |
| H | H | —OCH$_2$CH$_2$O— | H | H | OH | 2 | 1 | NH |
| H | H | —OCH$_2$CH$_2$O— | Cl | Cl | OH | 2 | 1 | NH |
| H | H | —OCH$_2$CH$_2$O— | Cl | H | OH | 2 | 1 | NH |
| H | H | —OCH$_2$CH$_2$O— | Cl | CH$_3$ | OH | 2 | 1 | NH |
| H | H | —OCH$_2$CH(CH$_3$)O— | CH$_3$ | CH$_3$ | OH | 2 | 1 | NSO$_2$CH$_3$ |
| H | H | —OCH$_2$CH(CH$_3$)O— | CH$_3$ | H | OH | 2 | 1 | NSO$_2$CH$_3$ |
| H | H | —OCH$_2$CH(CH$_3$)O— | H | H | OH | 2 | 1 | NSO$_2$CH$_3$ |
| H | H | —OCH$_2$CH(CH$_3$)O— | Cl | Cl | OH | 2 | 1 | NSO$_2$CH$_3$ |
| H | H | —OCH$_2$CH(CH$_3$)O— | Cl | H | OH | 2 | 1 | NSO$_2$CH$_3$ |
| H | H | —OCH$_2$CH(CH$_3$)O— | Cl | CH$_3$ | OH | 2 | 1 | NSO$_2$CH$_3$ |
| H | CH$_3$ | —OCH$_2$CH(CH$_3$)O— | CH$_3$ | CH$_3$ | OH | 2 | 1 | O |
| H | CH$_3$ | —OCH$_2$CH(CH$_3$)O— | CH$_3$ | H | OH | 2 | 1 | O |
| H | CH$_3$ | —OCH$_2$CH(CH$_3$)O— | H | H | OH | 2 | 1 | O |
| H | CH$_3$ | —OCH$_2$CH(CH$_3$)O— | Cl | Cl | OH | 2 | 1 | O |
| H | CH$_3$ | —OCH$_2$CH(CH$_3$)O— | Cl | H | OH | 2 | 1 | O |
| H | CH$_3$ | —CCH$_2$CH(CH$_3$)O— | Cl | CH$_3$ | OH | 2 | 1 | O |
| H | H | —OCH$_2$CH(CH$_3$)O— | CH$_3$ | CH$_3$ | OH | 2 | 1 | NH |
| H | H | —OCH$_2$CH(CH$_3$)O— | CH$_3$ | H | OH | 2 | 1 | NH |
| H | H | —OCH$_2$CH(CH$_3$)O— | H | H | OH | 2 | 1 | NH |
| H | H | —OCH$_2$CH(CH$_3$)O— | Cl | Cl | OH | 2 | 1 | NH |
| H | H | —OCH$_2$CH(CH$_3$)O— | Cl | H | OH | 2 | 1 | NH |
| H | H | —OCH$_2$CH(CH$_3$)O— | Cl | CH$_3$ | OH | 2 | 1 | NH |
| H | H | —OCH$_2$CH$_2$CH$_2$O— | CH$_3$ | CH$_3$ | OH | 2 | 1 | NSO$_2$CH$_3$ |
| H | H | —OCH$_2$CH$_2$CH$_2$O— | CH$_3$ | H | OH | 2 | 1 | NSO$_2$CH$_3$ |
| H | H | —OCH$_2$CH$_2$CH$_2$O— | H | H | OH | 2 | 1 | NSO$_2$CH$_3$ |
| H | H | —OCH$_2$CH$_2$CH$_2$O— | Cl | Cl | OH | 2 | 1 | NSO$_2$CH$_3$ |
| H | H | oxo | CH$_3$ | CH$_3$ | OH | 2 | 1 | NSO$_2$CH$_3$ |
| H | H | oxo | CH$_3$ | H | OH | 2 | 1 | NSO$_2$CH$_3$ |
| H | H | oxo | H | H | OH | 2 | 1 | NSO$_2$CH$_3$ |
| H | H | oxo | Cl | Cl | OH | 2 | 1 | NSO$_2$CH$_3$ |
| H | H | oxo | Cl | H | OH | 2 | 1 | NSO$_2$CH$_3$ |
| H | H | oxo | Cl | CH$_3$ | OH | 2 | 1 | NSO$_2$CH$_3$ |
| H | H | oxo | NO$_2$ | H | OH | 2 | 1 | NSO$_2$CH$_3$ |
| H | H | oxo | CH$_3$ | CH$_3$ | OH | 2 | 1 | O |
| H | H | oxo | CH$_3$ | H | OH | 2 | 1 | O |
| H | H | oxo | H | H | OH | 2 | 1 | O |
| H | H | oxo | Cl | Cl | OH | 2 | 1 | O |
| H | H | oxo | Cl | H | OH | 2 | 1 | O |
| H | H | oxo | Cl | CH$_3$ | OH | 2 | 1 | O |
| H | H | oxo | CH$_3$ | CH$_3$ | OH | 2 | 1 | NH |
| H | H | oxo | CH$_3$ | H | OH | 2 | 1 | NH |
| H | H | oxo | H | H | OH | 2 | 1 | NH |
| H | H | oxo | Cl | Cl | OH | 2 | 1 | NH |
| H | H | oxo | Cl | H | OH | 2 | 1 | NH |
| H | H | oxo | Cl | CH$_3$ | OH | 2 | 1 | NH |
| H | H | oxo | CH$_3$ | CH$_3$ | OH | 1 | 1 | NSO$_2$C$_2$H$_5$ |
| H | H | oxo | CH$_3$ | H | OH | 1 | 1 | NSO$_2$C$_2$H$_5$ |
| H | H | oxo | H | H | OH | 1 | 1 | NSO$_2$C$_2$H$_5$ |
| H | H | oxo | Cl | Cl | OH | 1 | 1 | NSO$_2$C$_2$H$_5$ |
| H | H | oxo | Cl | H | OH | 1 | 1 | NSO$_2$C$_2$H$_5$ |
| H | H | oxo | Cl | CH$_3$ | OH | 1 | 1 | NSO$_2$C$_2$H$_5$ |

TABLE 8

| R³ᵃ | R³ᵇ | R¹ R² | R⁴ | R⁵ | n | m | X |
|---|---|---|---|---|---|---|---|
| H | H | —OCH₂CH₂O— | CH₃ | CH₃ | 2 | 1 | NSO₂CH₃ |
| H | H | —OCH₂CH₂O— | CH₃ | H | 2 | 1 | NSO₂CH₃ |
| H | H | —OCH₂CH₂O— | H | H | 2 | 1 | NSO₂CH₃ |
| H | H | —OCH₂CH₂O— | Cl | Cl | 2 | 1 | NSO₂CH₃ |
| H | H | —OCH₂CH₂O— | Cl | H | 2 | 1 | NSO₂CH₃ |
| H | H | —OCH₂CH₂O— | Cl | CH₃ | 2 | 1 | NSO₂CH₃ |
| H | H | —OCH₂CH₂O— | NO₂ | H | 2 | 1 | NSO₂CH₃ |
| H | H | —OCH₂CH₂O— | CH₃ | CH₃ | 2 | 1 | O |
| H | H | —OCH₂CH₂O— | CH₃ | H | 2 | 1 | O |
| H | H | —OCH₂CH₂O— | H | H | 2 | 1 | O |
| H | H | —OCH₂CH₂O— | Cl | Cl | 2 | 1 | O |
| H | H | —OCH₂CH₂O— | Cl | H | 2 | 1 | O |
| H | H | —OCH₂CH₂O— | Cl | CH₃ | 2 | 1 | O |
| CH₃ | H | —CCH₂CH₂O— | CH₃ | CH₃ | 2 | 1 | NH |
| H | H | —OCH₂CH₂O— | CH₃ | H | 2 | 1 | NH |
| H | H | —OCH₂CH₂O— | H | H | 2 | 1 | NH |
| H | H | —OCH₂CH₂O— | Cl | Cl | 2 | 1 | NH |
| H | H | —OCH₂CH₂O— | Cl | H | 2 | 1 | NH |
| H | H | —OCH₂CH₂O— | Cl | CH₃ | 2 | 1 | NH |
| H | H | —OCH₂CH(CH₃)O— | CH₃ | CH₃ | 2 | 1 | NSO₂CH₃ |
| H | H | —OCH₂CH(CH₃)O— | CH₃ | H | 2 | 1 | NSO₂CH₃ |
| H | H | —OCH₂CH(CH₃)O— | H | H | 2 | 1 | NSO₂CH₃ |
| H | H | —OCH₂CH(CH₃)O— | Cl | Cl | 2 | 1 | NSO₂CH₃ |
| H | H | —OCH₂CH(CH₃)O— | Cl | H | 2 | 1 | NSO₂CH₃ |
| H | H | —OCH₂CH(CH₃)O— | Cl | CH₃ | 2 | 1 | NSO₂CH₃ |

TABLE 9

| R³ᵃ | R³ᵇ | R¹ R² | R⁴ | R⁵ | n | m | R⁹ | R¹⁰ |
|---|---|---|---|---|---|---|---|---|
| H | H | —OCH₂CH₂O— | CH₃ | CH₃ | 2 | 1 | CH₃ | H |
| H | H | —OCH₂CH₂O— | CH₃ | H | 2 | 1 | CH₃ | H |
| H | H | —OCH₂CH₂O— | H | H | 2 | 1 | CH₃ | H |
| H | H | —OCH₂CH₂O— | Cl | Cl | 2 | 1 | CH₃ | H |
| H | H | —OCH₂CH₂O— | Cl | H | 2 | 1 | CH₃ | H |
| H | H | —OCH₂CH₂O— | Cl | CH₃ | 2 | 1 | CH₃ | H |
| CH₃ | CH₃ | —OCH₂CH₂O— | CH₃ | CH₃ | 2 | 1 | CH₃ | H |
| CH₃ | CH₃ | —OCH₂CH₂O— | CH₃ | H | 2 | 1 | CH₃ | H |
| CH₃ | CH₃ | —OCH₂CH₂O— | H | H | 2 | 1 | CH₃ | H |
| CH₃ | CH₃ | —OCH₂CH₂O— | Cl | Cl | 2 | 1 | CH₃ | H |
| CH₃ | CH₃ | —OCH₂CH₂O— | Cl | H | 2 | 1 | CH₃ | H |
| CH₃ | CH₃ | —OCH₂CH₂O— | Cl | CH₃ | 2 | 1 | CH₃ | H |
| CH₃ | H | —OCH₂CH₂O— | CH₃ | CH₃ | 2 | 1 | CH₃ | H |
| CH₃ | H | —OCH₂CH₂O— | CH₃ | H | 2 | 1 | CH₃ | H |
| CH₃ | H | —OCH₂CH₂O— | H | H | 2 | 1 | CH₃ | H |
| CH₃ | H | —OCH₂CH₂O— | Cl | Cl | 2 | 1 | CH₃ | H |
| CH₃ | H | —OCH₂CH₂O— | Cl | H | 2 | 1 | CH₃ | H |
| CH₃ | H | —OCH₂CH₂O— | Cl | CH₃ | 2 | 1 | CH₃ | H |
| H | H | —OCH₂CH₂O— | CH₃ | CH₃ | 2 | 1 | CH₃ | CH₃ |
| H | H | —OCH₂CH₂O— | CH₃ | H | 2 | 1 | CH₃ | CH₃ |
| H | H | —OCH₂CH₂O— | H | H | 2 | 1 | CH₃ | CH₃ |
| H | H | —OCH₂CH₂O— | Cl | Cl | 2 | 1 | CH₃ | CH₃ |
| H | H | —OCH₂CH₂O— | Cl | H | 2 | 1 | CH₃ | CH₃ |
| H | H | —OCH₂CH₂O— | Cl | CH₃ | 2 | 1 | CH₃ | CH₃ |
| CH₃ | CH₃ | —OCH₂CH₂O— | CH₃ | CH₃ | 2 | 1 | CH₃ | CH₃ |
| CH₃ | CH₃ | —OCH₂CH₂O— | CH₃ | H | 2 | 1 | CH₃ | CH₃ |
| CH₃ | CH₃ | —OCH₂CH₂O— | H | H | 2 | 1 | CH₃ | CH₃ |
| CH₃ | CH₃ | —OCH₂CH₂O— | Cl | Cl | 2 | 1 | CH₃ | CH₃ |
| CH₃ | CH₃ | —OCH₂CH₂O— | Cl | H | 2 | 1 | CH₃ | CH₃ |
| CH₃ | CH₃ | —OCH₂CH₂O— | Cl | CH₃ | 2 | 1 | CH₃ | CH₃ |
| CH₃ | H | —OCH₂CH₂O— | CH₃ | CH₃ | 2 | 1 | CH₃ | CH₃ |
| CH₃ | H | —OCH₂CH₂O— | CH₃ | H | 2 | 1 | CH₃ | CH₃ |
| CH₃ | H | —OCH₂CH₂O— | H | H | 2 | 1 | CH₃ | CH₃ |
| CH₃ | H | —OCH₂CH₂O— | Cl | Cl | 2 | 1 | CH₃ | CH₃ |
| CH₃ | H | —OCH₂CH₂O— | Cl | H | 2 | 1 | CH₃ | CH₃ |
| CH₃ | H | —CCH₂CH₂O— | Cl | CH₃ | 2 | 1 | CH₃ | CH₃ |
| H | H | —OCH₂CH₂O— | CH₃ | CH₃ | 2 | 0 | CH₃ | H |
| H | H | —OCH₂CH₂O— | CH₃ | H | 2 | 0 | CH₃ | H |
| H | H | —OCH₂CH₂O— | H | H | 2 | 0 | CH₃ | H |
| H | H | —OCH₂CH₂O— | Cl | Cl | 2 | 0 | CH₃ | H |
| H | H | —OCH₂CH₂O— | Cl | H | 2 | 0 | CH₃ | H |
| H | H | —OCH₂CH₂O— | Cl | CH₃ | 2 | 0 | CH₃ | H |
| CH₃ | CH₃ | —OCH₂CH₂O— | CH₃ | CH₃ | 2 | 0 | CH₃ | H |
| CH₃ | CH₃ | —OCH₂CH₂O— | CH₃ | H | 2 | 0 | CH₃ | H |
| CH₃ | CH₃ | —OCH₂CH₂O— | H | H | 2 | 0 | CH₃ | H |
| CH₃ | CH₃ | —OCH₂CH₂O— | Cl | Cl | 2 | 0 | CH₃ | H |
| CH₃ | CH₃ | —OCH₂CH₂O— | Cl | H | 2 | 0 | CH₃ | H |
| CH₃ | CH₃ | —OCH₂CH₂O— | Cl | CH₃ | 2 | 0 | CH₃ | H |
| CH₃ | H | —OCH₂CH₂O— | CH₃ | CH₃ | 2 | 0 | CH₃ | CH₃ |
| CH₃ | H | —OCH₂CH₂O— | CH₃ | H | 2 | 0 | CH₃ | CH₃ |
| CH₃ | H | —OCH₂CH₂O— | H | H | 2 | 0 | CH₃ | CH₃ |
| CH₃ | H | —OCH₂CH₂O— | Cl | Cl | 2 | 0 | CH₃ | CH₃ |
| CH₃ | H | —OCH₂CH₂O— | Cl | H | 2 | 0 | CH₃ | CH₃ |
| CH₃ | H | —OCH₂CH₂O— | Cl | CH₃ | 2 | 0 | CH₃ | CH₃ |
| H | H | —OCH₂CH₂O— | CH₃ | CH₃ | 2 | 0 | CH₃ | CH₃ |
| H | H | —OCH₂CH₂O— | CH₃ | H | 2 | 0 | CH₃ | CH₃ |
| H | H | —OCH₂CH₂O— | H | H | 2 | 0 | CH₃ | CH₃ |
| H | H | —OCH₂CH₂O— | Cl | Cl | 2 | 0 | CH₃ | CH₃ |
| H | H | —OCH₂CH₂O— | Cl | H | 2 | 0 | CH₃ | CH₃ |
| H | H | —OCH₂CH₂O— | Cl | CH₃ | 2 | 0 | CH₃ | CH₃ |
| CH₃ | CH₃ | —OCH₂CH₂O— | CH₃ | CH₃ | 2 | 0 | CH₃ | CH₃ |
| CH₃ | CH₃ | —OCH₂CH₂O— | CH₃ | H | 2 | 0 | CH₃ | CH₃ |
| CH₃ | CH₃ | —OCH₂CH₂O— | H | H | 2 | 0 | CH₃ | CH₃ |
| CH₃ | CH₃ | —OCH₂CH₂O— | Cl | Cl | 2 | 0 | CH₃ | CH₃ |

Formulation/Utility

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges which add up to 100 percent by weight.

|  | Weight Percent | | |
|---|---|---|---|
|  | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers,* 2nd Ed., Dorland Books, Caldwell, N.J. Typical liquid diluents are described in Marsden, *Solvents Guide,* 2nd Ed., Interscience, New York, 1950. *McCutcheon's Detergents and Emulsifiers Annual,* Allured Publ. Corp., Ridgewood, N.J., as well as Sisely and Wood, *Encyclopedia of Surface Active Agents,* Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, org anosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147–48, *Perry's Chemical Engineer's Handbook*, 4th Ed., McGraw-Hill, New York, 1963, pages 8–57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and U.S. Pat. No. 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 14; Klingman, *Weed Control as a Science*, John Wiley and Sons, Inc., New York, 1961, pp 81–96; and Hance et al., *Weed Control Handbook,* 8th Ed., Blackwell Scientific Publications, Oxford, 1989.

In the following Examples, all percentages are by weight and all formulations are prepared in conventional ways. Compound numbers refer to compounds in Index Tables A–C.

Example A

High Strength Concentrate

| | |
|---|---|
| Compound 2 | 98.5% |
| silica aerogel | 0.5% |
| synthetic amorphous fine silica | 1.0%. |

Example B

Wettable Powder

| | |
|---|---|
| Compound 8 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example C

Granule

| | |
|---|---|
| Compound 2 | 10.0% |
| attapulgite granules (low volatile matter, 0.71/0.30 mm; U.S.S. No. 25–50 sieves) | 90.0%. |

Example D

Extruded Pellet

| | |
|---|---|
| Compound 8 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Test results indicate that the compounds of the present invention are highly active preemergent and postemergent herbicides or plant growth regulants. Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Some of the compounds are useful for the control of selected grass and broadleaf weeds with tolerance to important agronomic crops which include but are not limited to alfalfa, barley, cotton, wheat, rape, sugar beets, corn (maize), sorghum, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as eucalyptus and conifers (e.g., loblolly pine), and turf species (e.g., Kentucky bluegrass, St. Augustine grass, Kentucky fescue and Bermuda grass). Those skilled in the art will appreciate that not all compounds are equally effective against all weeds. Alternatively, the subject compounds are useful to modify plant growth.

Compounds of this invention can be used alone or in combination with other commercial herbicides, insecticides or fungicides. Compounds of this invention can also be used in combination with commercial herbicide safeners such as benoxacor, dichlormid and furilazole to increase safety to certain crops. A mixture of one or more of the following herbicides with a compound of this invention may be particularly useful for weed control: acetochlor, acifluorfen and its sodium salt, aclonifen, acrolein (2-propenal), alachlor, ametryn, amidosulfuron, amitrole, ammonium sulfamate, anilofos, asulam, atrazine, azimsulfuron, benazolin, benazolin-ethyl, benfluralin, benfuresate, bensulfuron-methyl, bensulide, bentazone, bifenox, bromacil, bromoxynil, bromoxynil octanoate, butachlor, butralin, butylate, chlomethoxyfen, chloramben, chlorbromuron, chloridazon, chlorimuron-ethyl, chlornitrofen, chlorotoluron, chlorpropham, chlorsulfuron, chlorthal-dimethyl, cinmethylin, cinosulfuron, clethodim, clomazone, clopyralid, clopyralid-olamine, cyanazine, cycloate, cyclosulfamuron, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, 2-[4,5-dihydro-4-methyl-4-(1-methyletbyl)-5-oxo-1H-imidazol-2-yl]-5-methyl-3-pyridinecarboxylic acid (AC 263,222), difenzoquat metilsulfate, diflufenican, dimepiperate, dimethenamid, dimethylarsinic acid and its sodium salt, dinitramine, diphenamid, diquat dibromide, dithiopyr, diuron, DNOC, endothal, EPTC, esprocarb, ethalfluralin, ethametsulfuron-methyl, ethofumesate, ethyl α,2-dichloro-5-[4-(difluoromethyl)4,5-dihydro-3-methyl-5-oxo-1H-1,2,4-triazol-1-yl]-4-fluorobenzenepropanoate (F8426), fenoxaprop-ethyl, fenoxaprop-P-ethyl, fenuron, fenuron-TCA, flamprop-methyl, flamprop-M-isopropyl, flamprop-M-methyl, flazasulfuron, fluazifop-butyl, fluazifop-P-butyl, fluchloralin, flumetsulam, flumiclorac-pentyl, flumioxazin, fluometuron, fluoroglycofen-ethyl, flupoxam, fluridone, flurochloridone, fluroxypyr, fomesafen, fosamine-ammonium, glufosinate, glufosinate-ammonium, glyphosate, glyphosate-isopropylammonium, glyphosate-sesquisodium, glyphosate-trimesium, halosulfuron-methyl, haloxyfop-etotyl, haloxyfop-methyl, hexazinone, imazamethabenz-methyl, imazamox (AC 299 263), imazapyr, imazaquin, imazaquin-ammonium, imazethapyr, imazethapyr-ammonium, imazosulfuron, ioxynil, ioxynil octanoate, ioxynil-sodium, isoproturon, isouron, isoxaben, isoxaflutole (RPA 201772), lactofen, lenacil, linuron, maleic hydrazide, MCPA and its dimethylammonium, potassium and sodium salts, MCPA-isoctyl, mecoprop, mecoprop-P, mefenacet, mefluidide, metam-sodium, methabenzthiazuron, methyl [[2-chloro-4-fluoro-5-[(tetrahydro-3-oxo-1H,3H-[1,3,4]thiadiazolo[3,4a]-pyridazin-1-ylidene)amino]phenyl]thioacetate (KIH 9201), methylarsonic acid and its calcium, monoammonium, monosodium and disodium salts, methyl [[[1-[5-[2-chloro-4-(trifluoromethyl)phenoxy]-2-nitrophenyl]-2-methoxyethylidene]amino]oxy]acetate (AKH-7088), methyl 5-[[[[(4,6-dimethyl-2-pyrimidinyl)amino]carbonyl] amino]sulfonyl]-1-(2-pyridinyl)-1H-pyrazole4-carboxylate (NC-330), metobenzuron, metolachlor, metosulam, metoxuron, metribuzin, metsulfuron-methyl, molinate, monolinuron, napropamide, naptalam, neburon, nicosulfuron, norflurazon, oryzalin, oxadiazon, 3-oxetanyl 2-[[[[(4,6-dimethyl-2-pyrimidinyl)amino]carbonyl]amino] sulfonyl]benzoate (CGA 277476), oxyfluorfen, paraquat dichloride, pebulate, pendimethalin, perfluidone, phenmedipham, picloram, picloram-potassium, pretilachlor, primisulfuron-methyl, prometon, prometryn, propachlor, propanil, propaquizafop, propazine, propham, propyzamide, prosulfuron, pyrazolynate, pyrazosulfuron-ethyl, pyridate, pyrithiobac, pyrithiobac-sodium, quinclorac, quizalofop-ethyl, quizalofop-P-ethyl, quizalofop-P-tefuryl, rimsulfuron, sethoxydim, siduron, simazine, sulcotrione (ICIA0051), sulfentrazone, sulfometuron-methyl, TCA, TCA-sodium, tebuthiuron, terbacil, terbuthylazine, terbutryn, thenylchlor, thiafluamide (BAY 11390), thifensulfuron-methyl, thiobencarb, tralkoxydim, tri-allate, triasulfuron, tribenuron-methyl, triclopyr, triclopyr-butotyl, triclopyr-triethylammonium, tridiphane, trifluralin, triflusulfuron-methyl, and vernolate.

In certain instances, combinations with other herbicides having a similar spectrum of control but a different mode of action will be particularly advantageous for preventing the development of resistant weeds.

Preferred for better control of undesired vegetation (e.g., lower use rate, broader spectrum of weeds controlled, or enhanced crop safety) or for preventing the development of resistant weeds are mixtures of a compound of this invention with a herbicide selected from the group atrazine, cyanazine, imazethapyr and its salt imazethapyr-ammonium, nicosulfuron, primisulfuron-methyl, pyrazosulfuron-ethyl, and rimsulfuron. Specifically preferred mixtures (compound numbers refer to compounds in Index Tables A–C) are selected from the group: compound 1 and atrazine; compound 1 and cyanazine; compound 1 and imazethapyr; compound 1 and nicosulfuron; compound 1 and primisulfuron-methyl; compound 1 and pyrazosulfuron-ethyl; compound 1 and rimsulfuron; compound 2 and atrazine; compound 2 and cyanazine; compound 2 and imazethapyr; compound 2 and nicosulfuron; compound 2 and primisulfuron-methyl; compound 2 and pyrazosulfuron-ethyl; compound 2 and rimsulfuron; compound 7 and atrazine; compound 7 and cyanazine; compound 7 and imazethapyr; compound 7 and nicosulfuron; compound 7 and primisulfuron-methyl; compound 7 and pyrazosulfuron-ethyl; compound 7 and rimsulfuron; compound 8 and atrazine; compound 8 and cyanazine; compound 8 and imazethapyr; compound 8 and nicosulfuron; compound 8 and primisulfuron-methyl; compound 8 and pyrazosulfuron-ethyl; compound 8 and rimsulfuron; compound 10 and atrazine; compound 10 and cyanazine; compound 10 and imazethapyr; compound 10 and nicosulfuron; compound 10 and primisulfuron-methyl; compound 10 and pyrazosulfuron-ethyl; and compound 10 and rimsulfuron.

A herbicidally effective amount of the compounds of this invention is determined by a number of factors. These factors include: formulation selected, method of application, amount and type of vegetation present, growing conditions, etc. In general, a herbicidally effective amount of compounds of this invention is 0.001 to 20 kg/ha with a preferred range of 0.004 to 1.0 kg/ha. One skilled in the art can easily determine the herbicidally effective amount necessary for the desired level of weed control.

The following Tests demonstrate the control efficacy of the compounds of this invention against specific weeds. The weed control afforded by the compounds is not limited, however, to these species. See Index Tables A–C for compound descriptions. The abbreviation "dec" indicates that the compound appeared to decompose on melting. The abbreviation "Ex." stands for "Example" and is followed by a number indicating in which example the compound is prepared.

INDEX TABLE A

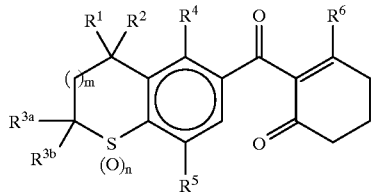

Formula I wherein Q is Q-1, X is S(O)$_n$,
Y and Z are CH$_2$, k is 0 and x is 1

| Cmpd | R$^{3a}$ | R$^{3b}$ | R$^1$ R$^2$ | R$^4$ | R$^5$ | R$^6$ | n | m | m.p. (° C.) |
|---|---|---|---|---|---|---|---|---|---|
| 1 (Ex. 1) | H | H | —OCH$_2$CH$_2$O— | H | H | OH | 2 | 1 | 131 (dec) |
| 2 (Ex. 5) | H | H | —OCH$_2$CH$_2$O— | CH$_3$ | CH$_3$ | OH | 2 | 1 | 130 (dec) |
| 3 | H | H | —OCH$_2$CH(CH$_3$)O— | CH$_3$ | CH$_3$ | OH | 2 | 1 | 159–160 |
| 4 (Ex. 3) | H | H | —OCH$_2$CH$_2$O— | Cl | Cl | OH | 2 | 1 | 140 (dec) |
| 5 | H | H | oxo | H | H | OH | 2 | 1 | 168 (dec) |
| 6$^a$ (Ex. 6) | H | H | —SCH$_2$CH$_2$S— | CH$_3$ | CH$_3$ | OH | 2 | 1 | 217–222 |

$^a$Compound contains approximately 16% by weight of 2,3-dihydro-5,8-dimethylspiro[4H-1-benzothiopyran-4,2'-[1,3]dithiolane]-6-carboxylic acid.

INDEX TABLE B

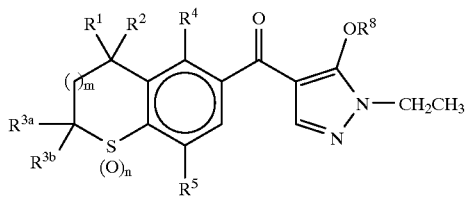

Formula I wherein Q is Q-2, X is S(O)$_n$, and k is 0

| Cmpd | R$^{3a}$ | R$^{3b}$ | R$^1$ R$^2$ | R$^4$ | R$^5$ | R$^8$ | n | m | m.p. (° C.) |
|---|---|---|---|---|---|---|---|---|---|
| 7 (Ex. 2) | H | H | —OCH$_2$CH$_2$O— | H | H | H | 2 | 1 | oil* |
| 8 (Ex. 4) | H | H | —OCH$_2$CH$_2$O— | CH$_3$ | CH$_3$ | H | 2 | 1 | 111 (dec) |
| 9 | H | H | —OCH$_2$CH$_2$O— | Cl | Cl | H | 2 | 1 | 130 (dec) |
| 10 | H | H | oxo | CH$_3$ | CH$_3$ | H | 2 | 1 | semi-solid* |

*See Index Table C for $^1$H NMR data.

INDEX TABLE C

| Cmpd No. | $^1$H NMR Data (CDCl$_3$ solution unless indicated otherwise)$^a$ |
|---|---|
| 7 | δ 1.46(t, 3H), 2.7(m, 2H), 3.7(m, 2H), 4.1(q, 2H), 4.2–4.3 (m, 4H), 7.7–8.0(4H). |
| 10 | δ 1.5(t, 3H), 2.5(s, 3H), 2.8(s, 3H), 3.3(m, 2H), 3.7 (m, 2H), 4.1(q, 2H), 7.3–7.46(2H). |

$^a$$^1$H NMR data are in ppm downfield from tetramethylsilane. Couplings are designated by (s)-singlet, (t)-triplet, (q)-quartet, (m)-multiplet.

BIOLOGICAL EXAMPLES OF THE INVENTION

Test A

Seeds of barley (*Hordeum vulgare*), barnyardgrass (*Echinochloa crus-galli*), bedstraw (*Galium aparine*), blackgrass (*Alopecurus myosuroides*), chickweed (*Stellaria media*), cocklebur (*Xanthium strumarium*), corn (*Zea mays*), cotton (*Gossypium hirsutum*), crabgrass (*Digitaria sanguinalis*), downy brome (*Bromus tectorum*), giant foxtail (*Setaria faberii*), lambsquarters (*Chenopodium album*), morningglory (*Ipomoea hederacea*), rape (*Brassica napus*), rice (*Oryza sativa*), sorghum (*Sorghum bicolor*), soybean (*Glycine max*), sugar beet (*Beta vulgaris*), velvetleaf (*Abutilon theophrasti*), wheat (*Triticum aestivum*), wild buckwheat (*Polygonum convolvulus*), wild oat (*Avena fatua*) and purple nutsedge (*Cyperus rotundus*) tubers were planted and treated preemergence with test chemicals formulated in a non-phytotoxic solvent mixture which includes a surfactant.

At the same time, these crop and weed species were also treated with postemergence applications of test chemicals formulated in the same manner. Plants ranged in height from two to eighteen cm (one to four leaf stage) for postemergence treatments. Treated plants and controls were maintained in a greenhouse for twelve to sixteen days, after which all species were compared to controls and visually evaluated. Plant response ratings, summarized in Table A, are based on a scale of 0 to 10 where 0 is no effect and 10 is complete control. A dash (-) response means no test result.

TABLE A

POSTEMERGENCE

COMPOUND

| | Rate 2000 g/ha | | | Rate 400 g/ha | | | | | | | | | Rate 200 g/ha | Rate 100 g/ha | | | | | | Rate 50 g/ha | | Rate 10 g/ha |
|---|---|---|---|---|---|---|---|---|---|---|---|---|---|---|---|---|---|---|---|---|---|---|
| | 1 | 5 | 7 | 1 | 2 | 3 | 4 | 5 | 6 | 7 | 8 | 9 | 6 | 2 | 3 | 4 | 6 | 8 | 9 | 3 | 6 | 3 |
| Barley | 0 | 0 | 0 | 0 | 9 | 9 | 5 | 0 | 5 | 0 | 0 | 2 | 0 | 7 | 8 | 4 | 3 | 0 | 0 | 4 | 1 | 2 |
| Barnyardgrass | 8 | 0 | 9 | 2 | 9 | 10 | 9 | 0 | 9 | 9 | 9 | 9 | 0 | 9 | 9 | 8 | 9 | 9 | 9 | 9 | 9 | 9 |
| Bedstraw | 6 | 0 | 8 | 5 | 9 | 9 | 9 | 0 | 9 | 7 | 9 | 9 | 2 | 9 | 9 | 9 | 8 | 9 | 6 | 9 | 8 | 7 |
| Blackgrass | 1 | 0 | 0 | 0 | 9 | 9 | 7 | 0 | 4 | 0 | 2 | 3 | 0 | 5 | 8 | 5 | 1 | 0 | 2 | 6 | 0 | 3 |
| Chickweed | 9 | 0 | 9 | 8 | 9 | 10 | 8 | 0 | 9 | 7 | 9 | 7 | 4 | 9 | 9 | 7 | 9 | 9 | 7 | 9 | 9 | 7 |
| Cocklebur | 9 | 0 | 9 | 7 | 9 | 9 | 9 | 0 | 9 | 9 | 9 | 9 | 3 | 9 | 9 | 9 | 9 | 9 | 8 | 9 | 9 | 9 |
| Corn | 0 | 0 | 1 | 0 | 9 | 5 | 2 | 0 | 1 | 1 | 7 | 1 | 0 | 7 | 3 | 1 | 0 | 5 | 0 | 1 | 0 | 0 |
| Cotton | 9 | 0 | 9 | 7 | 10 | 10 | 10 | 0 | 9 | 9 | 9 | 9 | 0 | 10 | 10 | 10 | 9 | 9 | 9 | 10 | 9 | 10 |
| Crabgrass | 8 | 0 | 9 | 3 | 10 | 9 | 7 | 0 | 6 | 9 | 9 | 3 | 6 | 9 | 9 | 2 | 3 | 9 | 2 | 9 | 3 | 8 |
| Downy brome | 0 | 0 | 0 | 0 | 9 | 9 | 6 | 0 | 0 | 0 | 2 | 2 | 0 | 6 | 9 | 5 | 0 | 0 | 0 | 7 | 0 | 0 |
| Giant foxtail | 2 | 0 | 8 | 1 | 9 | 9 | 5 | 0 | 1 | 3 | 9 | 6 | 0 | 9 | 9 | 3 | 1 | 9 | 4 | 8 | 0 | 2 |
| Lambsquarter | 9 | 0 | 9 | 6 | 9 | 9 | 9 | 0 | 9 | 8 | 9 | 9 | 9 | 9 | 9 | 9 | 9 | 9 | 8 | 9 | 9 | 9 |
| Morningglory | 9 | 0 | 2 | 7 | 10 | 10 | 10 | 0 | 9 | 2 | 8 | 6 | 1 | 10 | 10 | 10 | 9 | 8 | 1 | 10 | 9 | 9 |
| Nutsedge | 1 | — | 2 | 0 | 7 | 9 | 2 | 0 | 2 | 0 | — | 1 | — | 7 | 6 | 2 | 0 | 6 | 0 | 6 | 1 | 0 |
| Rape | 9 | 0 | 9 | 8 | 8 | 10 | 10 | 0 | 10 | 8 | 10 | 10 | 0 | 3 | 7 | 8 | 6 | 8 | 8 | 6 | — | 0 |
| Rice | 8 | 0 | 8 | 7 | 9 | 10 | 9 | 0 | 9 | 7 | 9 | 9 | — | 9 | 10 | 9 | 8 | 8 | 6 | 10 | 9 | 9 |
| Sorghum | 2 | 0 | 3 | 0 | 9 | 9 | 9 | 0 | 2 | 2 | 9 | 2 | 0 | 9 | 9 | 9 | 2 | 9 | 0 | 9 | 1 | 3 |
| Soybean | 9 | 0 | 9 | 8 | 10 | 10 | 9 | 0 | 9 | 8 | 9 | 4 | 0 | 10 | 10 | 8 | 8 | 8 | 3 | 10 | 8 | 7 |
| Sugar beet | 10 | 0 | 10 | 10 | 10 | 10 | 10 | 0 | 10 | 10 | 10 | 10 | 8 | 10 | 10 | 10 | 10 | 10 | 9 | 10 | 10 | 10 |
| Velvetleaf | 9 | 0 | 9 | 9 | 10 | 10 | 10 | 0 | 10 | 9 | 9 | 9 | — | 10 | 10 | 10 | 10 | 9 | 2 | 10 | 10 | 10 |
| Wheat | 0 | 0 | 0 | 0 | 10 | 9 | 8 | 0 | 3 | 0 | 6 | 2 | 0 | 8 | 8 | 6 | 2 | 2 | 1 | 8 | 2 | 2 |
| Wild buckwheat | 7 | 0 | 7 | 2 | 8 | 9 | 6 | 0 | 5 | 6 | 9 | 6 | 0 | 7 | 9 | 6 | 3 | 7 | 6 | 8 | 3 | 2 |
| Wild oat | 0 | 0 | 0 | 0 | 9 | 9 | 4 | 0 | 4 | 0 | 8 | 3 | 0 | 4 | 6 | 3 | 2 | 4 | 2 | 6 | 2 | 1 |

PREEMERGENCE

COMPOUND

| | Rate 2000 g/ha | | | Rate 400 g/ha | | | | | | | | | Rate 200 g/ha | Rate 100 g/ha | | | | | | Rate 50 g/ha | | Rate 10 g/ha |
|---|---|---|---|---|---|---|---|---|---|---|---|---|---|---|---|---|---|---|---|---|---|---|
| | 1 | 5 | 7 | 1 | 2 | 3 | 4 | 5 | 6 | 7 | 8 | 9 | 6 | 2 | 3 | 4 | 6 | 8 | 9 | 3 | 6 | 3 |
| Barley | 0 | 0 | 0 | 0 | 3 | 0 | 0 | 0 | 0 | 0 | 0 | 0 | 5 | 0 | 0 | 0 | 0 | 0 | 0 | 0 | 0 | 0 |
| Barnyardgrass | 0 | 0 | 2 | 0 | 10 | 9 | 5 | 0 | 0 | 0 | 9 | 2 | 9 | 10 | 8 | 1 | 0 | 0 | 0 | 5 | 0 | 0 |
| Bedstraw | 5 | — | 2 | — | 9 | 8 | 5 | 0 | 4 | 0 | 7 | 2 | 9 | 8 | 8 | 6 | 0 | 3 | 0 | 2 | 0 | 0 |
| Blackgrass | 0 | 0 | 1 | 0 | 2 | 2 | 2 | 0 | 0 | 0 | 0 | 0 | 3 | 0 | 0 | 1 | 0 | 0 | 0 | 0 | 0 | 0 |
| Chickweed | 7 | 0 | 3 | 0 | 8 | 10 | 4 | — | 7 | 0 | 8 | 7 | 9 | 8 | 8 | 3 | 0 | 6 | 7 | 7 | 0 | 0 |
| Cocklebur | 4 | 0 | 0 | 0 | 6 | 9 | 6 | 0 | 2 | 0 | 0 | 3 | 9 | 2 | 3 | 2 | 0 | 0 | 0 | 3 | 0 | 1 |
| Corn | 0 | 0 | 0 | 0 | 0 | 0 | 0 | 0 | 0 | 0 | 0 | 0 | 1 | 0 | 0 | 0 | 0 | 0 | 0 | 0 | 0 | 0 |
| Cotton | 1 | 0 | 0 | 0 | 6 | 4 | 8 | 0 | 2 | 0 | 1 | 7 | 9 | 3 | 4 | 3 | 0 | 0 | 0 | 0 | 0 | 0 |
| Crabgrass | 6 | 0 | 7 | 0 | 10 | 10 | 8 | 0 | 4 | 1 | 8 | 2 | 5 | 9 | 9 | 7 | 1 | 6 | 0 | 8 | 1 | 2 |
| Downy brome | 0 | — | 2 | 0 | 6 | 1 | 6 | 0 | 0 | 0 | 0 | 0 | 0 | 0 | 0 | 0 | 0 | 0 | 0 | 0 | 0 | 0 |
| Giant foxtail | 1 | 0 | 3 | 0 | 6 | 3 | 2 | 0 | 0 | 0 | 6 | 1 | 2 | 1 | 2 | 1 | 0 | 4 | 0 | 2 | 0 | 0 |
| Lambsquarter | 9 | — | 10 | 5 | 10 | 10 | 10 | — | 9 | 9 | 9 | 9 | 9 | 9 | 10 | 9 | 8 | 9 | 8 | 10 | 8 | 10 |
| Morningglory | 2 | 0 | 0 | 0 | 7 | 9 | 6 | — | 1 | 0 | 2 | 0 | 9 | 2 | 2 | 5 | 0 | 0 | 0 | 0 | 0 | 0 |
| Nutsedge | 0 | 0 | 0 | — | 10 | 10 | 3 | 0 | 0 | 0 | 0 | — | 2 | 0 | 1 | — | 0 | — | — | 0 | 0 | 0 |
| Rape | 10 | — | 7 | 0 | 3 | 3 | 9 | 0 | 0 | 0 | 0 | 0 | 10 | 0 | 0 | 3 | 0 | 0 | 0 | 0 | 0 | 0 |
| Rice | 9 | 0 | 3 | 0 | 9 | 10 | 7 | 0 | 1 | 0 | 6 | 3 | 9 | 9 | 8 | 7 | 0 | 2 | 0 | 8 | 0 | 1 |
| Sorghum | 0 | 0 | 0 | 0 | 6 | 3 | 2 | 0 | 0 | 0 | 5 | 0 | 2 | 3 | 0 | 1 | 0 | 0 | 0 | 0 | 0 | 0 |
| Soybean | 2 | 0 | 3 | 0 | 9 | 9 | 6 | 0 | 0 | 0 | 3 | 0 | 8 | 8 | 9 | 5 | 0 | 0 | 0 | 6 | 0 | 2 |
| Sugar beet | 9 | — | 8 | 9 | 10 | 10 | 10 | 0 | 8 | 0 | 9 | 9 | 10 | 10 | 10 | 10 | 0 | 9 | 9 | 10 | 0 | 9 |
| Velvetleaf | 6 | 0 | 1 | 0 | 10 | 10 | 10 | 0 | 6 | 0 | 10 | 0 | 10 | 10 | 9 | 9 | 0 | 5 | 0 | 7 | 0 | 2 |
| Wheat | 0 | 0 | 0 | 0 | 7 | 2 | 0 | 0 | 0 | 0 | 0 | 0 | 3 | 0 | 0 | 0 | 0 | 0 | 0 | 0 | 0 | 0 |
| Wild buckwheat | 0 | — | 0 | 0 | 7 | 9 | 6 | — | 0 | 0 | 0 | 3 | 5 | 3 | 2 | 2 | 0 | 0 | 0 | 0 | 0 | 0 |
| Wild oat | 0 | 0 | 0 | 0 | 4 | 2 | 0 | 0 | 0 | 0 | 0 | 0 | 4 | 1 | 0 | 0 | 0 | 0 | 0 | 0 | 0 | 0 |

Test B

The compounds evaluated in this test were formulated in a non-phytotoxic solvent mixture which includes a surfactant and applied to the soil surface before plant seedlings emerged (preemergence application), to water that covered the soil surface (flood application), and to plants that were in the one-to-four leaf stage (postemergence application). A sandy loam soil was used for the preemergence and postemergence tests, while a silt loam soil was used in the flood test. Water depth was approximately 2.5 cm for the flood test and was maintained at this level for the duration of the test.

Plant species in the preemergence and postemergence tests consisted of barnyardgrass (*Echinochloa crus-galli*), barley (*Hordeum vulgare*), bedstraw (*Galium aparine*), blackgrass (*Alopecurus myosuroides*), chickweed (*Stellaria media*), cocklebur (*Xanthium strumarium*), corn (*Zea mays*), cotton (*Gossypium hirsutum*), crabgrass (*Digitaria sanguinalis*), downy brome (*Bromus tectorum*), giant foxtail (*Setaria faberii*), johnsongrass (*Sorghum halpense*), lambsquarters (*Chenopodium album*), morningglory (*Ipomoea hederacea*), pigweed (*Amaranthus retroflexus*), rape (*Brassica napus*), ryegrass (*Lolium multiflorum*), soybean (*Glycine max*), speedwell (*Veronica persica*), sugar beet (*Beta vulgaris*), velvetleaf (*Abutilon theophrasti*), wheat (*Triticum aestivum*), wild buckwheat (*Polygonum convolvulus*), and wild oat (*Avena fatua*). All plant species were planted one day before application of the compound for the preemergence portion of this test. Plantings of these species were adjusted to produce plants of appropriate size for the postemergence portion of the test. Plant species in the flood test consisted of rice (*Oryza sativa*), umbrella sedge (*Cyperus difformis*), duck salad (*Heteranthera limosa*), barnyardgrass (*Echinochloa crus-galli*) and late watergrass (*Echinochloa oryzicola*) grown to the 2 leaf stage for testing.

All plant species were grown using normal greenhouse practices. Visual evaluations of injury expressed on treated plants, when compared to untreated controls, were recorded approximately fourteen to twenty one days after application of the test compound. Plant response this ratings, summarized in Table B, were recorded on a 0 to 100 scale where 0 is no effect and 100 is complete control. A dash (-) response means no test result.

TABLE B

POSTEMERGENCE

COMPOUND

| | Rate 500 g/ha | Rate 250 g/ha | | Rate 125 g/ha | | | | Rate 62 g/ha | | | | | | Rate 31 g/ha | | |
|---|---|---|---|---|---|---|---|---|---|---|---|---|---|---|---|---|
| | 7 | 4 | 7 | 2 | 4 | 7 | 8 | 2 | 3 | 4 | 7 | 8 | 9 | 2 | 3 | 4 |
| Barley Igri | — | 15 | — | 75 | 0 | — | 0 | 65 | 0 | 10 | — | 0 | 0 | 35 | 0 | 10 |
| Barnyardgr Flood | 20 | 70 | 10 | 100 | 60 | 10 | 95 | 95 | 85 | 35 | 0 | 95 | 0 | 85 | 85 | 20 |
| Barnyardgrass | 95 | 80 | 90 | 90 | 70 | 90 | 90 | 90 | 90 | 55 | 80 | 90 | 70 | 90 | 90 | 40 |
| Bedstraw | — | 90 | — | 100 | 90 | — | 85 | 80 | 95 | 90 | — | 80 | 45 | 80 | 85 | 80 |
| Blackgrass | — | 40 | — | 80 | 30 | — | 40 | 80 | 55 | 30 | — | 35 | 0 | 40 | 30 | 30 |
| Chickweed | — | 65 | — | 95 | 65 | — | 100 | 95 | 85 | 65 | — | 100 | 60 | 80 | 85 | 60 |
| Cocklebur | 85 | 90 | 85 | 90 | 90 | 85 | 90 | 90 | 90 | 90 | 70 | 90 | 70 | 80 | 90 | 90 |
| Corn | 0 | 0 | 0 | 0 | 0 | 0 | 35 | 0 | 0 | 30 | 0 | 0 | 10 | 0 | 0 | 0 |
| Cotton | 40 | 90 | 30 | 100 | 90 | 30 | 95 | 90 | 90 | 100 | 20 | 95 | 30 | 90 | 90 | 90 |
| Crabgrass | 95 | 85 | 90 | 90 | 75 | 80 | 90 | 90 | 90 | 75 | 50 | 90 | 30 | 90 | 90 | 60 |
| Downy Brome | — | 25 | — | 60 | 20 | — | 0 | 50 | 10 | 25 | — | 0 | 0 | 20 | 0 | 10 |
| Duck salad | 30 | 45 | 20 | 35 | 30 | 15 | 35 | 25 | 15 | 15 | 0 | 35 | 0 | 20 | 15 | 0 |
| Giant foxtail | 75 | 50 | 50 | 90 | 40 | 40 | 90 | 90 | 80 | 30 | 10 | 90 | 50 | 90 | 50 | 20 |
| Italn Ryegrass | — | 0 | — | 70 | 0 | — | 0 | 50 | 10 | 0 | — | 0 | 0 | 40 | 10 | 0 |
| Johnsongrass | 30 | — | 20 | 90 | — | 20 | 90 | 90 | — | 55 | 20 | 90 | 10 | 70 | — | 45 |
| Lambsquarter | — | 95 | — | 100 | 95 | — | 100 | 100 | 100 | 100 | — | 100 | 95 | 95 | 100 | 95 |
| Morningglory | 80 | 90 | 80 | 90 | 90 | 50 | 90 | 90 | 90 | 90 | 20 | 90 | 80 | 90 | 90 | 90 |
| Rape | — | 95 | — | 70 | 95 | — | 90 | 40 | 65 | 90 | — | 90 | 60 | 30 | 20 | 90 |
| Redroot Pigweed | 80 | 90 | 80 | 90 | 90 | 70 | 95 | 80 | 90 | 90 | 60 | 95 | 80 | 70 | 90 | 80 |
| Rice Japonica | 70 | 60 | 30 | 95 | 40 | 30 | 70 | 90 | 50 | 25 | 25 | 50 | 0 | 65 | 35 | 25 |
| Soybean | 85 | 90 | 70 | 90 | 80 | 70 | 90 | 90 | 90 | 90 | 50 | 85 | 40 | 90 | 90 | 90 |
| Speedwell | — | 100 | — | 100 | 95 | — | 100 | 95 | 100 | 95 | — | 100 | 60 | 70 | 95 | 80 |
| Sugar beet | — | 100 | — | 100 | 100 | — | 100 | 100 | 100 | 100 | — | 100 | 100 | 100 | 100 | 100 |
| Umbrella sedge | 30 | 50 | 0 | 75 | 40 | 0 | 85 | 65 | 40 | 15 | 0 | 60 | 0 | 30 | 25 | 0 |
| Velvetleaf | 90 | 100 | 90 | 95 | 100 | 85 | 100 | 95 | 100 | 100 | 70 | 100 | 60 | 95 | 100 | 95 |
| Watergrass 2 | 0 | 75 | 0 | 95 | 65 | 0 | 80 | 95 | 80 | 20 | 0 | 65 | 0 | 80 | 30 | 0 |
| Wheat | — | 25 | — | 75 | 0 | — | 0 | 70 | 50 | 30 | — | 0 | 0 | 55 | 35 | 25 |
| Wild buckwheat | — | 65 | — | 70 | 65 | — | 70 | 50 | 65 | 45 | — | 70 | 20 | 50 | 35 | 30 |
| Wild oat | — | 0 | — | 50 | 0 | — | 65 | 40 | 0 | 0 | — | 45 | 0 | 20 | 0 | 0 |

COMPOUND

| | Rate 31 g/ha | | Rate 16 g/ha | | | | | Rate 8 g/ha | | | | Rate 4 g/ha | | | Rate 2 g/ha | Rate 1 g/ha |
|---|---|---|---|---|---|---|---|---|---|---|---|---|---|---|---|---|
| | 2 | 3 | 2 | 3 | 4 | 8 | 9 | 3 | 4 | 8 | 9 | 4 | 8 | 9 | 8 | 8 |
| Barley Igri | 0 | 0 | 0 | 0 | 10 | 0 | 0 | 0 | 10 | 0 | 0 | 10 | 0 | 0 | 0 | 0 |
| Barnyardgr Flood | 80 | 0 | 20 | 40 | 0 | 65 | 0 | 25 | 0 | — | 0 | 0 | — | 0 | — | — |
| Barnyardgrass | 90 | 50 | 90 | 90 | 20 | 90 | 20 | 90 | 15 | 90 | 10 | 0 | 90 | 0 | 90 | 80 |
| Bedstraw | 80 | 0 | 70 | 85 | 40 | 65 | 0 | 80 | 20 | 50 | 0 | 20 | 35 | 0 | 10 | 0 |
| Blackgrass | 25 | 0 | 20 | 15 | 10 | 5 | 0 | 10 | 0 | 0 | 0 | 0 | 0 | 0 | 0 | 0 |
| Chickweed | 100 | 50 | 70 | 85 | 10 | 100 | 10 | 85 | 0 | 95 | 0 | 0 | 80 | 0 | 25 | 0 |
| Cocklebur | 90 | 70 | 80 | 90 | 90 | 90 | 50 | 90 | 80 | 90 | 35 | 65 | 80 | 10 | 80 | 70 |
| Corn | 0 | 0 | 0 | 0 | 0 | 0 | 0 | 0 | 0 | 0 | 0 | 0 | 0 | 0 | 0 | 0 |
| Cotton | 95 | 30 | 90 | 90 | 90 | 95 | 20 | 80 | 80 | 90 | 20 | 10 | 90 | 0 | 50 | 20 |
| Crabgrass | 90 | 20 | 85 | 90 | 40 | 90 | 10 | 90 | 30 | 80 | 0 | 10 | 70 | 0 | 40 | 10 |
| Downy Brome | 0 | 0 | 10 | 0 | 0 | 0 | 0 | 0 | 0 | 0 | 0 | 0 | 0 | 0 | 0 | 0 |
| Duck salad | 0 | 0 | 0 | 0 | 0 | 0 | 0 | 0 | 0 | — | 0 | 0 | — | 0 | — | — |
| Giant foxtail | 90 | 30 | 70 | 40 | 10 | 95 | 10 | 30 | 0 | 85 | 0 | 0 | 60 | 0 | 20 | 10 |
| Italn Ryegrass | 0 | 0 | 10 | 10 | 0 | 0 | 0 | 0 | 0 | 0 | 0 | 0 | 0 | 0 | 0 | 0 |
| Johnsongrass | 85 | 10 | 60 | — | 35 | 65 | 0 | — | 20 | 40 | 0 | 10 | 30 | 0 | 10 | 0 |
| Lambsguarter | 100 | 95 | 95 | 95 | 90 | 100 | 90 | 95 | 80 | 95 | 85 | 80 | 80 | 80 | 30 | 0 |
| Morningglory | 90 | 80 | 90 | 90 | 90 | 95 | 40 | 90 | 90 | 90 | 40 | 40 | 80 | 30 | 80 | 40 |
| Rape | 70 | 35 | 20 | 15 | 70 | 35 | 20 | 15 | 50 | 0 | 0 | 10 | 0 | 0 | 0 | 0 |
| Redroot Pigweed | 95 | 60 | 50 | 90 | 60 | 100 | 30 | 90 | 20 | 85 | 20 | 10 | 70 | 10 | — | 10 |

TABLE B-continued

| | | | | | | | | | | | | | | | | | |
|---|---|---|---|---|---|---|---|---|---|---|---|---|---|---|---|---|---|
| Rice Japonica | 30 | 0 | 30 | 25 | 0 | 20 | 0 | 20 | 0 | — | 0 | 0 | — | 0 | — | — |
| Soybean | 75 | 30 | 90 | 80 | 80 | 75 | 30 | 80 | 70 | 70 | 20 | 50 | 70 | 10 | 40 | 10 |
| Speedwell | 100 | 15 | 70 | 90 | 40 | 100 | 0 | 80 | 10 | 80 | 0 | 0 | 70 | 0 | 10 | 0 |
| Sugar beet | 100 | 90 | 100 | 100 | 100 | 100 | 80 | 100 | 100 | 100 | 10 | 100 | 100 | 10 | 70 | 40 |
| Umbrella sedge | 20 | 0 | 30 | 0 | 0 | 0 | 0 | 0 | 0 | — | 0 | 0 | — | 0 | — | — |
| Velvetleaf | 100 | 50 | 95 | 100 | 90 | 100 | 30 | 90 | 90 | 100 | 30 | 90 | 100 | 20 | 100 | 80 |
| Watergrass 2 | 25 | 0 | 0 | 15 | 0 | 15 | 0 | 15 | 0 | — | 0 | 0 | — | 0 | — | — |
| Wheat | 0 | 0 | 40 | 0 | 0 | 0 | 0 | 0 | 0 | 0 | 0 | 0 | 0 | 0 | 0 | 0 |
| Wild buckwheat | 50 | 20 | 30 | 35 | 20 | 45 | 10 | 35 | 0 | 40 | 0 | 0 | 40 | 0 | 0 | 0 |
| Wild oat | 20 | 0 | 10 | 0 | 0 | 10 | 0 | 0 | 0 | 0 | 0 | 0 | 0 | 0 | 0 | 0 |

PREEMERGENCE

COMPOUND

| | Rate 500 g/ha | Rate 250 g/ha | Rate 125 g/ha | | | | Rate 62 g/ha | | | | | | Rate 31 g/ha | | |
|---|---|---|---|---|---|---|---|---|---|---|---|---|---|---|---|---|
| | 7 | 4 | 7 | 2 | 4 | 7 | 8 | 2 | 3 | 4 | 7 | 8 | 9 | 2 | 3 | 4 |
| Barley Igri | 0 | 0 | 0 | 0 | 0 | 0 | 0 | 0 | 0 | 0 | 0 | 0 | 0 | 0 | 0 | 0 |
| Barnyardgrass | 30 | 95 | 10 | 95 | 50 | 10 | 100 | 85 | 90 | 20 | 0 | 70 | 0 | 50 | 30 | 0 |
| Bedstraw | 0 | 80 | 0 | 95 | 65 | 0 | 0 | 50 | 70 | 10 | 0 | 0 | 0 | 0 | 20 | 10 |
| Blackgrass | 0 | 0 | 0 | 10 | 0 | 0 | 0 | 0 | 0 | 0 | 0 | 0 | 0 | 0 | 0 | 0 |
| Chickweed | 0 | 0 | 0 | 100 | 0 | 0 | 95 | 100 | 85 | 0 | 0 | 75 | 0 | 0 | 70 | 0 |
| Cocklebur | 0 | 50 | 0 | 70 | 40 | 0 | 30 | 50 | 70 | 20 | 0 | 20 | 10 | 40 | 50 | 10 |
| Corn | 10 | 0 | 10 | 0 | 0 | 0 | 20 | 0 | 25 | 0 | 0 | 10 | 0 | 0 | 0 | 0 |
| Cotton | 0 | 70 | 0 | 90 | 40 | 0 | 20 | 90 | 50 | 30 | 0 | — | 0 | 10 | 50 | 10 |
| Crabgrass | 95 | 100 | 80 | 100 | 90 | 40 | 100 | 100 | 100 | 50 | 20 | 40 | 0 | 100 | 80 | 20 |
| Downy Brome | 0 | 0 | 0 | 10 | — | 0 | 0 | 0 | 80 | 0 | 0 | 0 | 0 | 0 | 40 | 0 |
| Giant foxtail | 20 | 85 | 0 | 50 | 40 | 0 | 100 | 40 | 40 | 20 | 0 | 80 | 0 | 20 | — | 35 |
| Italn Ryegrass | 0 | 0 | 0 | 40 | 0 | 0 | 0 | 0 | 10 | 0 | 0 | 0 | 0 | 0 | 0 | 0 |
| Johnsongrass | 10 | 30 | 0 | 35 | 20 | 0 | 20 | 25 | 70 | 10 | 0 | 10 | — | 10 | 50 | 0 |
| Lambsouarter | 95 | 90 | 95 | 100 | 90 | 90 | 100 | 100 | 100 | 95 | 0 | 95 | 95 | 95 | 95 | 95 |
| Morningglory | 0 | 100 | 0 | 85 | 75 | 0 | 50 | 60 | 0 | 65 | 0 | 0 | 0 | 50 | 0 | 20 |
| Rape | 0 | 95 | 0 | 0 | 30 | 0 | 0 | 0 | 0 | 0 | 0 | 0 | 0 | 0 | 0 | 0 |
| Redroot Pigweed | 0 | — | 0 | 90 | 0 | 0 | 100 | 10 | — | 75 | 0 | 70 | 30 | 10 | — | 20 |
| Soybean | 0 | 90 | 0 | 90 | 70 | 0 | 20 | 80 | 40 | 40 | 0 | 0 | 10 | 55 | — | 20 |
| Speedwell | 10 | 100 | 0 | 100 | 90 | 0 | 100 | 95 | 100 | 95 | 0 | 100 | — | 30 | 100 | 95 |
| Sugar beet | 10 | 100 | 0 | 100 | 100 | 0 | 100 | 100 | 100 | 100 | 0 | 100 | 85 | 100 | 100 | 100 |
| Velvetleaf | 0 | 100 | 0 | 100 | 100 | 0 | 100 | 100 | 100 | 100 | 0 | 60 | 10 | 100 | 80 | 30 |
| Wheat | 0 | 0 | 0 | 0 | 0 | 0 | 0 | 0 | 0 | 0 | 0 | 0 | 0 | 0 | 0 | 0 |
| Wild buckwheat | 0 | 10 | 0 | 10 | 0 | 0 | 0 | 0 | 0 | 0 | 0 | 0 | 0 | 0 | 0 | 0 |
| Wild oat | 0 | 0 | 0 | 0 | 0 | 0 | 0 | 0 | 20 | 0 | 0 | 0 | 0 | 0 | 0 | 0 |

COMPOUND

| | Rate 31 g/ha | | Rate 16 g/ha | | | | | Rate 8 g/ha | | | | Rate 4 g/ha | | | Rate 2 g/ha | Rate 1 g/ha |
|---|---|---|---|---|---|---|---|---|---|---|---|---|---|---|---|---|
| | 2 | 3 | 2 | 3 | 4 | 8 | 9 | 3 | 4 | 8 | 9 | 4 | 8 | 9 | 8 | 8 |
| Barley Igri | 10 | 0 | 0 | 0 | 0 | 0 | 0 | 0 | 0 | 0 | 0 | 0 | 0 | 0 | 0 | 0 |
| Barnyardgrass | 50 | 0 | 35 | 20 | 0 | 15 | 0 | 0 | 0 | 0 | 0 | 0 | 0 | 0 | 0 | 0 |
| Bedstraw | 80 | 0 | 0 | 10 | 0 | 80 | 0 | 0 | 0 | 10 | 0 | 0 | 0 | 0 | 0 | 0 |
| Blackgrass | 0 | 0 | 0 | 0 | 0 | 0 | 0 | 0 | 0 | 0 | 0 | 0 | 0 | 0 | 0 | 0 |
| Chickweed | 55 | 0 | 0 | 50 | 0 | 25 | 0 | 10 | 0 | 0 | 0 | 0 | 0 | 0 | 0 | 0 |
| Cocklebur | 0 | 10 | 30 | 30 | 0 | 0 | 10 | 10 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 |
| Cotton | 0 | 0 | 10 | 30 | 0 | 0 | 0 | 30 | 0 | 0 | 0 | 0 | 0 | 0 | 0 | 0 |
| Crabgrass | 70 | 0 | 95 | — | 0 | 5 | 0 | 10 | 0 | 20 | 0 | 0 | 0 | 0 | 0 | 0 |
| Downy Brome | 0 | 0 | 0 | 0 | 0 | 0 | 0 | 0 | 0 | 0 | 0 | 0 | 0 | 0 | 0 | 0 |
| Giant foxtail | 70 | 0 | 0 | 40 | 0 | 20 | 0 | 30 | 0 | 25 | — | 0 | 0 | 0 | 0 | 0 |
| Italn Ryegrass | 40 | 0 | 0 | 0 | 0 | 25 | 0 | 0 | 0 | 0 | 0 | 0 | 0 | 0 | 0 | 0 |
| Johnsongrass | 70 | — | 10 | 50 | 0 | 40 | — | 40 | 0 | 30 | — | 0 | 30 | — | 0 | 0 |
| Larbsouarter | 90 | 30 | 95 | 90 | 95 | 55 | 30 | 90 | 80 | 90 | 0 | 0 | 90 | 0 | 70 | 40 |
| Morningglory | 100 | 0 | 50 | 0 | 0 | 60 | 0 | 0 | 0 | 50 | 0 | 0 | 20 | 0 | 0 | 0 |
| Rape | 95 | 0 | 0 | 0 | 0 | 50 | 0 | 0 | 0 | 0 | 0 | 0 | 0 | 0 | — | 0 |
| Redroot Pigweed | 0 | 20 | 0 | — | 0 | 0 | — | 0 | — | 0 | 0 | — | 0 | — | — | — |
| Soybean | 40 | 10 | 20 | — | 10 | 30 | 0 | — | 0 | 0 | 0 | 0 | 10 | 0 | 0 | 0 |
| Speedwell | 100 | 100 | 30 | 100 | 0 | 100 | 100 | 80 | — | 100 | 100 | 0 | 90 | 10 | 10 | 0 |
| Sugar beet | 40 | 80 | 80 | 100 | 100 | 30 | 0 | 85 | 100 | 10 | 0 | 0 | 0 | 0 | 0 | 0 |
| Velvetleaf | 30 | 0 | 100 | 50 | 0 | 5 | 0 | 20 | 0 | 20 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 |
| Wild buckwheat | 20 | 0 | 0 | 0 | 0 | 20 | 0 | 0 | 0 | 0 | 0 | 0 | 0 | 0 | 0 | 0 |
| Wild oat | 0 | 0 | 0 | 0 | 0 | 0 | 0 | 0 | 0 | 0 | 0 | 0 | 0 | 0 | 0 | 0 |

Test C

Seeds of barnyardgrass (*Echinochloa crus-galli*), bindweed (*Convolvulus arvensis*), black nightshade (*Solanum ptycanthum dunal*), cassia (*Cassia obtusifolia*), cocklebur (*Xanthium strumarium*), common ragweed (*Ambrosia artemisiifolia*), corn (*Zea mays*), cotton (*Gossypium hirsutum*), crabgrass (Digitaria spp.), fall panicum (*Panicum dichotomiflorum*), giant foxtail (*Setaria faberii*), green foxtail (*Setaria viridis*), jimsonweed (*Datura stramonium*), johnsongrass (*Sorghum halepense*), lambsquarter (*Chenopodium album*), morningglory (Ipomoea spp.), pigweed (*Amaranthus retroflexus*), prickly sida (*Sida spinosa*), shattercane (*Sorghum vulgare*), signalgrass (*Brachiaria platyphylla*), smartweed (*Polygonum pensylvanicum*), soybean (*Glycine max*), sunflower (*Helianthus annuus*), velvetleaf (*Abutilon theophrasti*), wild proso (*Panicum miliaceum*), woolly cupgrass (*Eriochloa villosa*), yellow foxtail (*Setaria lutescens*) and purple nutsedge (*Cyperus rotundus*) tubers were planted into a matapeake sandy loam soil. These crops and weeds were grown in the greenhouse until the plants ranged in height from two to eighteen cm (one to four leaf stage), then treated postemergence with the test chemicals formulated in a non-phytotoxic solvent mixture which includes a surfactant. Pots receiving preemergence treatments were planted immediately prior to test chemical application. Pots treated in this fashion were placed in the greenhouse and maintained according to routine greenhouse procedures.

Treated plants and untreated controls were maintained in the greenhouse approximately 14–21 days after application of the test compound. Visual evaluations of plant injury responses were then recorded. Plant response ratings, summarized in Table C, are reported on a 0 to 100 scale where 0 is no effect and 100 is complete control.

TABLE C

POSTEMERGENCE

COMPOUND

|  | Rate 70 g/ha | Rate 35 g/ha | | Rate 17 g/ha | | Rate 8 g/ha | | Rate 4 g/ha | | Rate 2 g/ha |
|---|---|---|---|---|---|---|---|---|---|---|
|  | 2 | 2 | 8 | 2 | 8 | 2 | 8 | 2 | 8 | 8 |
| Barnyardgrass | 100 | 100 | 90 | 95 | 90 | 95 | 90 | 80 | 80 | 5 |
| Bindweed | 100 | 100 | 50 | 90 | 10 | 90 | 0 | 80 | 0 | 0 |
| Blk Nightshade | 100 | 100 | 100 | 100 | 95 | 100 | 85 | 100 | 80 | 80 |
| Cassia | — | — | 10 | — | 5 | — | 0 | — | 0 | 0 |
| Cocklebur | 100 | 100 | 90 | 100 | 85 | 100 | 70 | 100 | 50 | 40 |
| Corn | 10 | 5 | 0 | 5 | 0 | 0 | 0 | 0 | 0 | 0 |
| Cotton | 100 | 100 | 40 | 100 | 40 | 90 | 25 | 90 | 20 | 10 |
| Crabgrass | 100 | 90 | 70 | 85 | 70 | 80 | 10 | 40 | 5 | 0 |
| Fall Panicum | 100 | 100 | 90 | 90 | 90 | 50 | 50 | 5 | 50 | 0 |
| Giant Foxtail | 90 | 40 | 90 | 30 | 90 | 5 | 40 | 0 | 30 | 0 |
| Green Foxtail | 90 | 80 | 90 | 50 | 90 | 5 | 30 | 0 | 20 | 0 |
| Jimsonweed | 100 | 100 | 95 | 100 | 95 | 100 | 90 | 100 | 90 | 90 |
| Johnson Grass | 40 | 20 | 80 | 10 | 30 | 0 | 0 | 0 | 0 | 0 |
| Lambsquarter | 100 | 100 | 90 | 100 | 90 | 100 | 85 | 90 | 80 | 5 |
| Morningglory | 100 | 100 | 90 | 100 | 85 | 100 | 40 | 100 | 10 | 0 |
| Nutsedge | 90 | 90 | 0 | 70 | 0 | 5 | 0 | 5 | 0 | 0 |
| Pigweed | 100 | 100 | 100 | 90 | 100 | 80 | 80 | 40 | 5 | 0 |
| Prickly Sida | 100 | 95 | 5 | 90 | 0 | 70 | 0 | 65 | 0 | 0 |
| Ragweed | 100 | 100 | 90 | 100 | 90 | 100 | 80 | 90 | 5 | 5 |
| Shattercane | 100 | 100 | 80 | 80 | 5 | 10 | 0 | 0 | 0 | 0 |
| Signalgrass | 100 | 100 | — | 90 | — | 80 | — | 50 | — | — |
| Smartweed | 100 | 100 | 100 | 100 | 100 | 100 | 80 | 90 | 70 | 20 |
| Soybean | 100 | 100 | 60 | 100 | 40 | 100 | 30 | 100 | 10 | 5 |
| Sunflower | 100 | 100 | 90 | 100 | 70 | 90 | — | 90 | 30 | — |
| Velvetleaf | 100 | 100 | 95 | 100 | 95 | 100 | 90 | 100 | 90 | 0 |
| Wild Proso | 100 | 100 | 90 | 100 | 90 | 80 | 90 | 70 | 50 | 5 |
| Woolly cupgrass | 90 | 90 | 80 | 80 | 50 | 30 | 5 | 30 | 5 | 0 |
| Yellow Foxtail | 80 | 70 | 90 | 50 | 60 | 10 | 20 | 0 | 0 | 0 |

Test D

Compounds evaluated in this test were formulated in a non-phytotoxic solvent mixture which includes a surfactant and applied to the soil surface before plant seedlings emerged (preemergence application) and to plants that were grown for various periods of time before treatment (postemergence application). A sandy loam soil was used for the preemergence test while a mixture of sandy loam soil and greenhouse potting mix in a 60:40 ratio was used for the postemergence test. Test compounds were applied within approximately one day after planting seeds for the preemergence test.

Plantings of these crops and weed species were adjusted to produce plants of appropriate size for the postemergence test. All plant species were grown using normal greenhouse practices. Crop and weed species include american black nightshade (*Solanum americanum*), arrowleaf sida (*Sida rhombifolia*), barnyardgrass (*Echinochloa crus-galli*), cocklebur (*Xanthium strumarium*), common lambsquarters (*Chenopodium album*), common ragweed (*Ambrosia artemisiifolia*), corn (*Zea mays*), cotton (*Gossypium hirsutum*), eastern black nightshade (*Solanum ptycanthum*), fall panicum (*Panicum dichotomiflorum*), field bindweed (*Convolvulus arvensis*), Florida beggarweed (*Desmodium*

*purpureum*), giant foxtail (*Setaria faberii*), hairy beggarticks (*Bidens pilosa*), ivyleaf morningglory (*Ipomoea hederacea*), johnsongrass (*Sorghum halepense*), ladysthumb (*Polygonum persicaria*), large crabgrass (*Digitaria sanguinalis*), purple nutsedge (*Cyperus rotundus*), redroot pigweed (*Amaranthus retroflexus*), soybean (*Glycine max*), surinam grass (*Brachiaria decumbens*), velvetleaf (*Abutilon theophrasti*) and wild poinsettia (*Euphorbia heterophylla*).

Treated plants and untreated controls were maintained in a greenhouse for approximately 14 to 21 days, after which all treated plants were compared to untreated controls and visually evaluated. Plant response ratings, summarized in Table D, are based upon a 0 to 100 scale where 0 is no effect and 100 is complete control. A dash response (-) means no test result.

TABLE D

POSTEMERGENCE

COMPOUND

| | Rate 140 g/ha | Rate 70 g/ha | | Rate 35 g/ha | | | Rate 17 g/ha | | | Rate 8 g/ha | | | Rate 4 g/ha | | | Rate 2 g/ha | | |
|---|---|---|---|---|---|---|---|---|---|---|---|---|---|---|---|---|---|---|
| | 8 | 2 | 8 | 2 | 3 | 8 | 2 | 3 | 8 | 2 | 3 | 8 | 2 | 3 | 8 | 2 | 3 | 8 |
| Arrowleaf Sida | 35 | 90 | 40 | 85 | 80 | 35 | 80 | 70 | 25 | 65 | 40 | 15 | 60 | 35 | 10 | 20 | 25 | 0 |
| Barnyardgrass | 100 | 95 | 100 | 95 | 90 | 95 | 90 | 60 | 85 | 85 | 45 | 75 | 70 | 20 | 45 | 25 | 15 | 15 |
| Cocklebur | 95 | 100 | 100 | 100 | 100 | 100 | 100 | 100 | 100 | 100 | 90 | 95 | 95 | 85 | 85 | 90 | 45 | 45 |
| Common Ragweed | 95 | 100 | 100 | 100 | 95 | 100 | 100 | 80 | 95 | 100 | 70 | 85 | 95 | 60 | 85 | 85 | 55 | 25 |
| Corn | 10 | 10 | 10 | 10 | 0 | 0 | 0 | 0 | 0 | 0 | 0 | 0 | 0 | 0 | 0 | 0 | 0 | 0 |
| Cotton | 95 | 100 | 100 | 100 | 100 | 100 | 100 | 95 | 85 | 95 | 90 | 70 | 90 | 85 | 15 | 80 | 40 | 10 |
| Estrn Blknight | 100 | 100 | 100 | 100 | 100 | 100 | 95 | 95 | 100 | 90 | 50 | 75 | 85 | 45 | 70 | 70 | 35 | 60 |
| Fall Panicum | 100 | 95 | 100 | 85 | 60 | 100 | 70 | — | 95 | 55 | 25 | 80 | 45 | 10 | 80 | 20 | 0 | 0 |
| Field Bindweed | 80 | 90 | 65 | 85 | 90 | 65 | 70 | 85 | 50 | 50 | 60 | 40 | 35 | 45 | 35 | 25 | 40 | 25 |
| Fl Beggarweed | 100 | 100 | 100 | 100 | 100 | 100 | 100 | 85 | 100 | 100 | — | 95 | 100 | 25 | 100 | 95 | 20 | 10 |
| Giant Foxtail | 100 | 85 | 100 | 60 | 65 | 95 | 35 | 30 | 95 | 15 | 15 | 55 | 15 | 10 | 15 | 10 | 0 | 0 |
| Hairy Beggartic | 70 | 75 | 90 | 50 | 45 | 90 | 30 | 25 | 75 | 25 | 20 | 65 | 20 | 0 | 30 | 10 | 0 | 0 |
| Ivyleaf Mrnglry | 85 | 100 | 95 | 95 | 95 | 85 | 95 | 90 | 80 | 90 | 70 | 65 | 90 | 50 | 55 | 65 | 15 | 0 |
| Johnsongrass | 50 | 50 | 80 | 15 | 30 | 80 | 0 | 10 | 15 | 0 | 0 | 10 | 0 | 0 | 0 | 0 | 0 | 0 |
| Ladysthumb | 90 | 100 | 100 | 100 | 100 | 95 | 85 | 100 | 90 | 75 | 95 | 45 | 50 | 45 | 25 | 30 | 30 | 15 |
| Lambsquarters | 100 | 100 | 100 | 100 | 100 | 100 | 100 | 95 | 95 | 100 | 95 | 95 | 95 | 90 | 75 | 95 | 70 | 20 |
| Large Crabgrass | 95 | 95 | 95 | 90 | 85 | 95 | 80 | — | 80 | 70 | 60 | 55 | 55 | 35 | 30 | 30 | 15 | 10 |
| Purple Nutsedge | 70 | 75 | 75 | 50 | 40 | 65 | 20 | 25 | 10 | 10 | 10 | 10 | 0 | 0 | 0 | 0 | 0 | 0 |
| Redroot Pigweed | — | 100 | 100 | 100 | 95 | 100 | 75 | 90 | 95 | 65 | 80 | 85 | 35 | 50 | 80 | 15 | 40 | 70 |
| Soybean | 90 | 100 | 100 | 100 | 95 | 100 | 100 | 95 | 75 | 100 | 90 | 65 | 95 | 85 | 60 | 80 | 65 | 25 |
| Surinam Grass | 85 | 85 | 100 | 80 | 75 | 75 | 65 | 60 | 70 | 35 | 35 | 40 | 20 | 10 | 15 | 15 | 0 | 0 |
| Velvetleaf | 100 | 100 | 100 | 100 | 100 | 100 | 100 | 100 | 100 | 100 | 95 | 95 | 100 | 90 | 75 | 100 | 35 | 25 |
| Wild Poinsettia | 60 | 100 | 70 | 100 | 95 | 45 | 100 | — | 25 | 95 | 80 | 20 | 85 | 45 | 15 | 55 | 25 | 10 |

PREEMERGENCE

COMPOUND

| | Rate 70 g/ha | | Rate 35 g/ha | | | Rate 17 g/ha | | | Rate 8 g/ha | | | Rate 4 g/ha | | | Rate 2 g/ha | | |
|---|---|---|---|---|---|---|---|---|---|---|---|---|---|---|---|---|---|
| | 2 | 8 | 2 | 3 | 8 | 2 | 3 | 8 | 2 | 3 | 8 | 2 | 3 | 8 | 2 | 3 | 8 |
| Arrowleaf Sida | 95 | 15 | 95 | 10 | 10 | 50 | 0 | 0 | 10 | 0 | 0 | — | 0 | 0 | — | 0 | 0 |
| Barnyardgrass | 70 | 40 | 30 | 20 | 10 | 25 | 0 | 0 | 0 | 0 | 0 | 0 | 0 | 0 | 0 | 0 | 0 |
| Cocklebur | 95 | 10 | 40 | 25 | 0 | 10 | 0 | 0 | 0 | 0 | 0 | 0 | 0 | 0 | 0 | 0 | 0 |
| Common Ragweed | 95 | 65 | 95 | 75 | 50 | 85 | 25 | 25 | 10 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 |
| Cotton | 25 | 15 | — | 0 | 10 | 10 | 0 | 0 | 0 | 0 | 0 | — | 0 | — | 0 | 0 | 0 |
| Fall Panicum | — | 100 | — | 15 | 40 | 20 | 0 | 25 | — | 0 | 10 | 0 | 0 | 0 | — | 0 | 0 |
| Field Bindweed | 80 | — | — | 0 | 0 | 25 | 0 | 0 | — | 0 | — | — | 0 | — | — | 0 | — |
| Fl Beggarweed | — | — | — | — | — | — | — | — | 0 | 25 | — | — | — | — | — | — | — |
| Giant Foxtail | 10 | 80 | 10 | 0 | 20 | 0 | 0 | 10 | 0 | 0 | 0 | 0 | 0 | 0 | 0 | 0 | 0 |
| Hairy Beggartic | 10 | 25 | 0 | 25 | 25 | 0 | 0 | 25 | 0 | 0 | 0 | 0 | 0 | 0 | 0 | 0 | 0 |
| Ivyleaf Mrnglry | 0 | 15 | 0 | 20 | 10 | — | 0 | — | 0 | 0 | 0 | — | — | — | 0 | 0 | — |
| Johnsongrass | 0 | 10 | 0 | 0 | 0 | 0 | 0 | 0 | 0 | 0 | 0 | 0 | 0 | 0 | 0 | — | 0 |
| Ladysthumb | — | — | — | 95 | 30 | — | 80 | — | — | 0 | — | — | 0 | — | — | 0 | 0 |
| Lambsquarters | 100 | — | 100 | — | — | 00 | — | — | 75 | 95 | 0 | 50 | — | 0 | 10 | 85 | 0 |
| Large Crabgrass | 100 | 25 | 100 | 35 | 15 | 70 | 10 | 0 | 10 | 10 | 0 | 0 | 0 | 0 | 0 | 0 | 0 |
| Purple Nutsedge | 50 | 45 | 35 | — | 25 | 25 | — | 0 | 0 | 0 | 0 | — | 0 | — | 0 | — | 0 |
| Redroot Pigweed | — | — | — | 100 | 65 | — | 100 | — | — | 90 | — | — | 0 | — | — | — | — |
| Soybean | — | 10 | — | — | 0 | — | 0 | 0 | — | 0 | 0 | — | 0 | 0 | 15 | — | 0 |
| Surinam Grass | 70 | 75 | 45 | 15 | 35 | 20 | 0 | 10 | 0 | 0 | 0 | 0 | 0 | 0 | 0 | 0 | 0 |
| Velvetleaf | 100 | 100 | 100 | 80 | 85 | 00 | 75 | 65 | 35 | 60 | 15 | 15 | 20 | 0 | 10 | 0 | 0 |
| Wild Poinsettia | 85 | 30 | 75 | 25 | 55 | 15 | 85 | 15 | 0 | 0 | 0 | 0 | 0 | 0 | 0 | 0 | 0 |

Test E

Plastic pots were partially filled with silt loam soil. The soil was then saturated with water. Rice (*Oryza sativa*) seed or seedlings at the 2.0 leaf stage; seeds, tubers or plant parts selected from barnyardgrass (*Echinochloa crus-galli*), ducksalad (*Heteranthera limosa*), junglerice (*Echinochloa colonum*), late watergrass (*Echinochloa oryzicola*), redstem (Ammania species), rice flatsedge (*Cyperus iria*), smallflower flatsedge (*Cyperus difformis*) and tighthead sprangletop (*Leptochloa fasicularis*), were planted into this soil. Plantings and waterings of these crops and weed species were adjusted to produce plants of appropriate size for the test. At the two leaf stage, water levels were raised to 3 cm above the soil surface and maintained at this level throughout the test. Chemical treatments were formulated in a non-phytotoxic solvent mixture which includes a surfactant and applied directly to the paddy water, by pipette, or to the plant foliage, by an air-pressure assisted, calibrated belt-conveyer spray system.

Treated plants and controls were maintained in a greenhouse for approximately 21 days, after which all species were compared to controls and visually evaluated. Plant response ratings, summarized in Table E, are reported on a 0 to 100 scale where 0 is no effect and 100 is complete control. A dash (-) response means no test result.

TABLE E

|  | COMPOUND 8 |
|---|---|
| Rate 64 g/ha | |
| PADDY APPL/TAMA SOIL | |
| barnyardgrass | 30 |
| ducksalad | 95 |
| junglerice | 70 |
| late watergrass | 0 |
| redstem | 75 |
| rice flatsedge | 100 |
| smallflower flatsedge | 100 |
| tighthead sprangletop | 100 |
| 2 LF direct seeded indica type rice | 70 |
| 2 LF transp. indica type rice | 60 |
| Rate 32 g/ha | |
| PADDY APPL/TAMA SOIL | |
| barnyardgrass | 20 |
| ducksalad | 90 |
| junglerice | 80 |
| late watergrass | 0 |
| redstem | 60 |
| rice flatsedge | 100 |
| smallflower flatsedge | 100 |
| tighthead sprangletop | 95 |
| 2 LF direct seeded indica type rice | 45 |
| 2 LF transp. indica type rice | 35 |
| Rate 16 g/ha | |
| PADDY APPL/TAMA SOIL | |
| barnyardgrass | 0 |
| ducksalad | 45 |
| junglerice | 60 |
| late watergrass | 0 |
| redstem | 45 |
| rice flatsedge | 100 |
| smallflower flatsedge | 50 |
| tighthead sprangletop | 100 |
| 2 LF direct seeded indica type rice | 35 |
| 2 LF transp. indica type rice | 30 |
| Rate 8 g/ha | |
| PADDY APPL/TAMA SOIL | |
| barnyardgrass | 0 |
| ducksalad | 50 |
| junglerice | 30 |
| late watergrass | 0 |
| redstem | 20 |
| rice flatsedge | 00 |
| smallflower flatsedge | 65 |
| tighthead sprangletop | 80 |

TABLE E-continued

|  | COMPOUND 8 |
|---|---|
| 2 LF direct seeded indica type rice | 40 |
| 2 LF transp. indica type rice | 20 |
| Rate 4 g/ha | |
| PADDY APPL/TAMA SOIL | |
| barnyardgrass | 0 |
| ducksalad | 55 |
| junglerice | 0 |
| late watergrass | 10 |
| redstem | 0 |
| rice flatsedge | 90 |
| smallflower flatsedge | 45 |
| tighthead sprangletop | 50 |
| 2 LF direct seeded indica type rice | 20 |
| 2 LF transp. indica type rice | 10 |

Test F

Seeds, tubers, or plant parts of alexandergrass (*Brachiaria plantaginea*), bermudagrass (*Cynodon dactylon*), broadleaf signalgrass (*Brachiaria plantyphylla*), common purslane (*Portulaca oleracea*), common ragweed (*Ambrosia elatior*), dallisgrass (*Paspalum dilatatum*), goosegrass (*Eleusine indica*), guineagrass (*Panicum maximum*), itchgrass (*Rottboellia exaltata*), johnson grass (*Sorghum halepense*), large crabgrass (*Digitaria sanguinalis*), peanuts (*Arachis hypogaea*), pitted morningglory (*Ipomoea lacunosa*), purple nutsedge (*Cyperus rotundus*), sandbur (*Cenchrus echinatus*), sourgrass (*Trichachne insularis*) and Surinam grass (*Brachiaria decumbens*) were planted into greenhouse pots or flats containing greenhouse planting medium. Plant species were grown in separate pots or individual compartments. Test chemicals were formulated in a non-phytotoxic solvent mixture which includes a surfactant and applied preemergence and postemergence to the plants. Preemergence applications were made within one day of planting the seed or plant part. Postemergence applications were applied when the plants were in the two to four leaf stage (three to twenty cm).

Untreated control plants and treated plants were placed in the greenhouse and visually evaluated for injury 13 to 21 days after herbicide application. Plant response ratings, summarized in Table F, are based on a 0 to 100 scale where 0 is no injury and 100 is complete control. A dash (-) response means no test result.

TABLE F

| | POSTEMERGENCE | |
|---|---|---|
| | COMPOUND | |
| | Rate 125 g/ha 2 | Rate 64 g/ha 2 |
| Alexandergrass | 100 | 80 |
| Bermudagrass | 95 | 90 |
| Brdlf Sgnlgrass | 98 | 98 |
| Com Purslane | 98 | 98 |
| Com Ragweed | 90 | 85 |
| Cotton | 100 | 100 |
| Dallisgrass | 90 | 75 |
| Goosegrass | 80 | 75 |
| Guineagrass | 40 | 20 |
| Itchgrass | 35 | 15 |
| Johnson grass | 80 | 40 |
| Large Crabgrass | 90 | 75 |

TABLE F-continued

| | | |
|---|---|---|
| Peanuts | 60 | 50 |
| Pit Morninglory | 100 | 85 |
| Purple Nutsedge | 65 | 65 |
| Sandbur | 75 | 40 |
| Sourgrass | 80 | 80 |
| Surinam grass | 75 | 70 |

| PREEMERGENCE | | |
|---|---|---|
| | COMPOUND | |
| | Rate 125 g/ha 2 | Rate 64 g/ha 2 |
| Alexandergrass | 35 | — |
| Bermudagrass | 75 | 65 |
| Brdlf Sgnlgrass | 20 | 20 |
| Cmn Purslane | 90 | 65 |
| Cmn Ragweed | 98 | 80 |
| Cotton | 60 | 60 |
| Dallisgrass | 25 | 0 |
| Itchgrass | 35 | 25 |
| Johnson grass | 35 | 35 |
| Large Crabgrass | 85 | 0 |
| Peanuts | 25 | 0 |
| Pit Morninglory | 90 | 0 |
| Purple Nutsedge | 0 | 0 |
| Sandbur | 0 | 0 |
| Sourgrass | 100 | 100 |
| Surinam grass | 80 | 0 |

Test G

Compounds evaluated in this test were formulated in a non-phytotoxic solvent mixture which includes a surfactant and applied to the soil surface before plant seedlings emerged (preemergence application) and to plants that were in the one-to four leaf stage (postemergence application). A sandy loam soil was used for the preemergence test while a mixture of sandy loam soil and greenhouse potting mix in a 60:40 ratio was used for the postemergence test. Test compounds were applied within approximately one day after planting seeds for the preemergence test.

Plantings of these crops and weed species were adjusted to produce plants of appropriate size for the postemergence test. All plant species were grown using normal greenhouse practices. Crop and weed species include annual bluegrass (*Poa annua*), black nightshade (*Solanum nigra*), blackgrass (*Alopecurus myosuroides*), chickweed (*Stellaria media*), deadnettle (*Lamium amplexicaule*), downy brome (*Bromus tectorum*), field violet (*Viola arvensis*), galium (*Galium aparine*), green foxtail (*Setaria viridis*), jointed goatgrass (*Aegilops cylindrica*), kochia (*Kochia scoparia*), lambsquarters (*Chenopodium album*), littleseed canarygrass (*Phalaris minor*), rape (*Brassica napus*), redroot pigweed (*Amaranthus retroflexus*), ryegrass (*Lolium multiflorum*), scentless chamomile (*Matricaria inodora*), speedwell (*Veronica persica*), spring barley (*Hordeum vulgare* cv. 'Klages'), spring wheat (*Triticum aestivum* cv. 'ERA'), sugar beet (*Beta vulgaris* cv. 'US1'), sunflower (*Helianthus annuus* cv. 'Russian Giant'), wild buckwheat (*Polygonum convolvulus*), wild mustard (*Sinapis arvensis*), wild oat (*Avenafatua*), windgrass (*Apera spica-venti*), winter barley (*Hordeum vulgare* cv. 'Igri') and winter wheat (*Triticum aestivum* cv. 'Talent').

Wild oat was treated at two growth stages. The first stage (1) was when the plant had two to three leaves. The second stage (2) was when the plant had approximately four leaves or in the initial stages of tillering. Treated plants and untreated controls were maintained in a greenhouse for approximately 21 to 28 days, after which all treated plants were compared to untreated controls and visually evaluated. Plant response ratings, summarized in Table G, are based upon a 0 to 100 scale where 0 is no effect and 100 is complete control. A dash response (-) means no test result.

TABLE G

| | POSTEMERGENCE | | | | | | | | | | | |
|---|---|---|---|---|---|---|---|---|---|---|---|---|
| | COMPOUND | | | | | | | | | | | |
| | Rate 31 g/ha | | | Rate 16 g/ha | | | Rate 8 g/ha | | | Rate 4 g/ha | | |
| | 4 | 8 | 9 | 4 | 8 | 9 | 4 | 8 | 9 | 4 | 8 | 9 |
| Annual Bluegrass | 0 | — | 5 | 0 | — | 0 | 0 | — | 0 | 0 | — | 0 |
| Blackgrass | 0 | 10 | 5 | 0 | 10 | 0 | 0 | 0 | 0 | 0 | 0 | 0 |
| Blk Nightshade | 100 | 90 | 10 | 30 | 80 | 0 | 10 | 75 | 0 | 0 | 80 | 0 |
| Chickweed | 0 | — | 0 | 0 | 100 | 0 | 0 | 85 | 0 | 0 | 65 | 0 |
| Deadnettle | 90 | 85 | 10 | 35 | 90 | 5 | 0 | 50 | 0 | 0 | 15 | 0 |
| Downy brome | 10 | 0 | 5 | 0 | 0 | 0 | 0 | 0 | 0 | 0 | 0 | 0 |
| Field violet | 0 | 80 | — | 0 | 80 | 0 | 0 | 30 | — | 0 | 15 | 0 |
| Galium | 65 | 40 | 35 | 10 | 65 | 0 | 0 | 20 | 0 | 0 | 20 | 0 |
| Green foxtail | 10 | 100 | 0 | 5 | 85 | 0 | 0 | 85 | 0 | 0 | 40 | 0 |
| Jointed Goatgra | 5 | 0 | 5 | 0 | 0 | 0 | 0 | 0 | 0 | 0 | 0 | 0 |
| Kochia | 35 | — | 0 | 0 | — | 0 | 0 | — | 0 | 0 | — | 0 |
| Lambsquarters | 100 | 45 | 40 | 30 | 50 | — | 0 | 50 | 30 | 0 | 50 | 10 |
| LS Canarygrass | 0 | 0 | 5 | 0 | 0 | 0 | 0 | 0 | 0 | 0 | 0 | 0 |
| Rape | 30 | — | 15 | 0 | — | 0 | 5 | — | — | 0 | — | — |
| Redroot Pigweed | 85 | 50 | 65 | 60 | 55 | — | — | 45 | — | 30 | 15 | — |
| Ryegrass | 5 | 0 | 0 | 5 | 0 | 0 | 0 | 0 | 0 | 0 | 0 | 0 |
| Scentless Chamom | 80 | 45 | 70 | 70 | 50 | 40 | — | 70 | 0 | 20 | 25 | 10 |
| Speedwell | 30 | 80 | 0 | 15 | 80 | 0 | 0 | 65 | 0 | 0 | 20 | 0 |
| Spring Barley | 10 | 0 | 0 | 0 | 0 | 0 | 0 | 0 | 0 | 0 | 0 | 0 |
| Sugar beet | 100 | — | 100 | 35 | — | 70 | 25 | — | 70 | 15 | — | 40 |
| Sunflower | 75 | — | 5 | 0 | — | 0 | 0 | — | 0 | 0 | — | 0 |
| Wheat (Spring) | 15 | 0 | 0 | 0 | 0 | 0 | 0 | 0 | 0 | 0 | 0 | 0 |
| Wheat (Winter) | 15 | 0 | 0 | 0 | 0 | 0 | 0 | 0 | 0 | 0 | 0 | 0 |
| Wild buckwheat | 0 | 10 | 0 | 0 | 10 | 0 | 0 | 0 | 0 | 0 | 0 | 0 |

TABLE G-continued

| | | | | | | | | | | | | |
|---|---|---|---|---|---|---|---|---|---|---|---|---|
| Wild mustard | 100 | 100 | 70 | 50 | 100 | 85 | 30 | — | 25 | 30 | 90 | 20 |
| Wild oat (1) | — | 0 | — | — | 0 | — | — | 0 | — | — | 0 | — |
| Wild oat (2) | 5 | 5 | 0 | 0 | 0 | 0 | 0 | 0 | 0 | 0 | 0 | 0 |
| Windgrass | 0 | 0 | 5 | 0 | 0 | 0 | 0 | 0 | 0 | 0 | 0 | 0 |
| Winter Barley | 5 | 0 | 0 | 0 | 0 | 0 | 0 | 0 | 0 | 0 | 0 | 0 |

PREEMERGENCE

COMPOUND

| | Rate 31 g/ha | | Rate 16 g/ha | | Rate 8 g/ha | | Rate 4 g/ha | |
|---|---|---|---|---|---|---|---|---|
| | 2 | 8 | 2 | 8 | 2 | 8 | 2 | 8 |
| Annual Bluegrass | 0 | 0 | 0 | 0 | 0 | 0 | 0 | 0 |
| Blackgrass | 0 | 0 | 0 | 0 | 0 | 0 | 0 | 0 |
| Blk Nightshade | 10 | 5 | 10 | 0 | 0 | 0 | 0 | 0 |
| Chickweed | 10 | 10 | 20 | 0 | 0 | 0 | 0 | 0 |
| Deadnettle | 20 | 0 | 0 | 0 | 10 | 0 | 0 | 0 |
| Downy brome | 0 | 0 | 0 | 0 | 0 | 0 | 0 | 0 |
| Galium | 0 | 0 | 0 | 0 | 0 | 0 | 0 | 0 |
| Green foxtail | 0 | 0 | 0 | 0 | 0 | 0 | 0 | 0 |
| Jointed Goatgra | 0 | 0 | 0 | 0 | 0 | 0 | 0 | 0 |
| Kochia | 0 | 0 | 0 | 0 | 0 | 0 | — | 0 |
| Lambsquarters | 95 | 85 | 85 | 80 | 75 | 60 | 50 | 10 |
| LS Canarygrass | 0 | 0 | 0 | 0 | 0 | 0 | 0 | 0 |
| Redroot Pigweed | — | 85 | 60 | — | 10 | 65 | 0 | 25 |
| Ryegrass | 0 | 0 | 0 | 0 | 0 | 0 | 0 | 0 |
| Scentless Chamom | — | 0 | — | 0 | — | 0 | — | 0 |
| Speedwell | 35 | 75 | 10 | 65 | 10 | 30 | 10 | 15 |
| Spring Barley | 0 | 0 | 0 | 0 | 0 | 0 | 0 | 0 |
| Wheat (Spring) | 0 | 0 | 0 | 0 | 0 | 0 | 0 | 0 |
| Wheat (Winter) | 0 | 30 | 0 | 10 | 0 | 0 | 0 | 0 |
| Wild buckwheat | 0 | 0 | 0 | 0 | 0 | 0 | 0 | 0 |
| Wild mustard | 15 | 0 | 15 | 0 | 5 | 0 | 0 | 0 |
| Wild oat (1) | 0 | 0 | 0 | 0 | 0 | 0 | 0 | 0 |
| Windgrass | 0 | 0 | 0 | 0 | 0 | 0 | 0 | 0 |
| Winter Barley | 0 | 5 | 0 | 0 | 0 | 0 | 0 | 0 |

What is claimed is:

1. A compound selected from Formula I, and agriculturally suitable salts thereof,

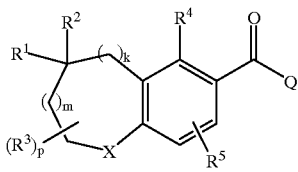

I wherein

Q is

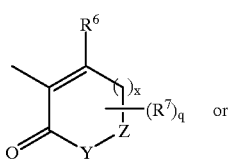

Q-1

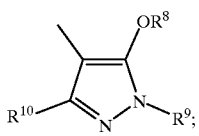

Q-2

$R^1$ and $R^2$ are each independently $C_1$–$C_6$ alkoxy, $C_2$–$C_6$ haloalkoxy, $C_1$–$C_6$ alkylthio or $C_2$–$C_6$ haloalkylthio; or $R^1$ and $R^2$ are taken together to form —$X^1$—(CH$_2$)—$X^2$—, —(CH$_2$)$_s$—$X^3$—, —(CH$_2$)$_t$—$X^3$—CH$_2$—, —(CH$_2$)$_v$—$X^3$—CH$_2$CH$_2$— or —(CH$_2$)$_w$—, each group optionally substituted with at least one member selected from 1–6 halogen, 1–6 CH$_3$ and one $C_1$–$C_3$ alkoxy; or $R^1$ and $R^2$ are taken together to form —O—N($C_1$–$C_3$ alkyl)—CHR$^{12}$—CH$_2$— or —O—N=CHR$^{12}$—CH$_2$—, each group optionally substituted with at least one member selected from 1–2 halogen and 1–2 CH$_3$; or $R^1$ and $R^2$ are taken together with the carbon to which they are attached to form C(=O) or C(=S);

$X^1$ and $X^2$ are each independently O, S or N($C_1$–$C_3$ alkyl);

$X^3$ is O or S;

each $R^3$ is independently H or CH$_3$;

$R^4$ and $R^5$ are each independently H, $C_1$–$C_6$ alkyl, $C_1$–$C_6$ haloalkyl, $C_1$–$C_6$ alkoxy, $C_1$–$C_6$ haloalkoxy, $C_1$–$C_6$ alkylthio, $C_1$–$C_6$ haloalkylthio, $C_1$–$C_6$ alkylsulfinyl, $C_1$–$C_6$ haloalkylsulfinyl, $C_1$–$C_6$ alkylsulfonyl, $C_1$–$C_6$ haloalkylsulfonyl, halogen, cyano or nitro;

$R^6$ is OR$^{11}$, $C_1$–$C_6$ alkylthio, $C_1$–$C_6$ haloalkylthio, $C_1$–$C_6$ alkylsulfinyl, $C_1$–$C_6$ haloalkylsulfinyl, $C_1$–$C_6$ alkylsulfonyl, $C_1$–$C_6$ haloalkylsulfonyl, cyano, cyanato, thiocyanato or halogen;

each $R^7$ is independently $C_1$–$C_3$ alkyl, $C_1$–$C_3$ alkoxy, $C_1$–$C_3$ alkylthio or halogen; or when two $R^7$ are attached to the same carbon atom, then said $R^7$ pair can be taken together to form —OCH$_2$CH$_2$O—, —OCH$_2$CH$_2$CH$_2$O—, —SCH$_2$CH$_2$S— or —SCH$_2$CH$_2$CH$_2$S—, each group optionally substituted with 1–4 CH$_3$;

R$^8$ is H, C$_1$–C$_6$ alkyl, C$_1$–C$_6$ haloalkyl, C$_1$–C$_6$ alkoxyalkyl, formyl, C$_1$–C$_6$ alkylcarbonyl, C$_2$–C$_6$ alkoxycarbonyl, C$_2$–C$_6$ alkylaminocarbonyl, C$_3$–C$_7$ dialkylaminocarbonyl, C$_1$–C$_6$ alkylsulfonyl or C$_1$–C$_6$ haloalkylsulfonyl; or R$^8$ is benzoyl or phenylsulfonyl, each optionally substituted with C$_1$–C$_3$ alkyl, halogen, cyano or nitro;

R$^9$ is H, C$_1$–C$_6$ alkyl, C$_1$–C$_6$ haloalkyl, C$_3$–C$_6$ alkenyl or C$_3$–C$_6$ alkynyl; or R$^9$ is phenyl or benzyl, each optionally substituted on the phenyl ring with C$_1$–C$_3$ alkyl, halogen, cyano or nitro;

R$^{10}$ is H, C$_1$–C$_6$ alkyl, C$_1$–C$_6$ haloalkyl, halogen, cyano or nitro;

R$^{11}$ is H, C$_1$–C$_6$ alkyl, C$_1$–C$_6$ haloalkyl, C$_2$–C$_6$ alkoxyalkyl, formyl, C$_2$–C$_6$ alkylcarbonyl, C$_2$–C$_6$ alkoxycarbonyl, C$_2$–C$_6$ alkylaminocarbonyl, C$_3$–C$_7$ dialkylaminocarbonyl, C$_1$–C$_6$ alkylsulfonyl or C$_1$–C$_6$ haloalkylsulfonyl; or R$^{11}$ is benzoyl or phenylsulfonyl, each optionally substituted with C$_1$–C$_3$ alkyl, halogen, cyano or nitro;

R$^{12}$ is C$_1$–C$_3$ alkyl; or R$^{12}$ is phenyl optionally substituted with C$_1$–C$_3$ alkyl, halogen, cyano or nitro;

X is S(O)$_n$;

R$^{13}$ is H, C$_1$–C$_3$ alkyl, C$_3$–C$_4$ alkenyl, C$_3$–C$_4$ alkynyl, formyl, C$_2$–C$_3$ alkylcarbonyl, C$_2$–C$_3$ alkoxycarbonyl or C$_1$–C$_2$ alkylsulfonyl;

Y is O; S; NH; N(C$_1$–C$_3$ alkyl); or CH$_2$ optionally substituted with R$^7$ when q is other than 0;

Z is a direct bond; O; S(O)$_z$; NH; N(C$_1$–C$_3$ alkyl); or CH$_2$ optionally substituted with R$^7$ when q is other than 0; provided that when Y is O, S, NH or N(C$_1$–C$_3$ alkyl), then Z is a direct bond or CH$_2$ optionally substituted with R$^7$;

k and m are each independently 0, 1 or 2, provided that the sum of k and m is 0, 1 or 2;

n and p are each independently 0, 1 or 2;

q is 0, 1, 2, 3 or 4;

r is 2, 3 or 4;

s is 2, 3, 4 or;

t is 1, 2, 3 or 4;

v is 2 or 3;

w is 2, 3, 4, 5 or 6;

x is 1 or 2; and z is 0, 1 or 2;

provided that (i) when X is S(O)$_n$, Q is Q–1 and R$^1$ and R$^2$ are independently C$_1$–C$_6$ alkoxy, C$_2$–C$_6$ haloalkoxy, C$_1$–C$_6$ alkylthio or C$_2$–C$_6$ haloalkylthio or are taken together with the carbon to which they are attached to form C(=O), then n is 1 or 2.

2. A compound of claim 1 wherein:

each R$^7$ is independently C$_1$–C$_3$ alkyl or halogen;

X is S(O)$_n$;

Y and Z are independently CH$_2$ optionally substituted with R$^7$;

k is 0; and x is 1.

3. A compound of claim 2 wherein:

R$^1$ and R$^2$ are independently C$_1$–C$_6$ alkoxy, C$_2$–C$_6$ haloalkoxy, C$_1$–C$_6$ alkylthio or C$_2$–C$_6$ haloalkylthio; or R$^1$ and R$^2$ are taken together to form —X—(CH$_2$)$_r$—X2— optionally substituted with at least one member selected from 1–6 halogen and 1–6 CH$_3$; or R$^1$ and R$^2$ are taken together with the carbon to which they are attached to form C(=O);

X$^1$ and X$^2$ are both O or both S;

m is 1 or 2; and r is 2 or 3.

4. A compound of claim 3 wherein:

R$^4$ and R$^5$ are independently H, C$_1$–C$_3$ alkyl or halogen;

R$^7$ is C$_1$–C$_3$ alkyl;

R$^9$ is H, C$_1$–C$_6$ alkyl or C$_3$–C$_6$ alkenyl;

R$^{10}$ is H;

R$^{11}$ is H, formyl, C$_2$–C$_6$ alkylcarbonyl, C$_2$–C$_6$ alkoxycarbonyl, C$_2$–C$_6$ alkylaminocarbonyl, C$_3$–C$_7$ dialkylaminocarbonyl, C$_1$–C$_6$ alkylsulfonyl or C$_1$–C$_6$ haloalkylsulfonyl; or R$^{11}$ is benzoyl or phenylsulfonyl, each optionally substituted with C$_1$–C$_3$ alkyl, halogen, cyano or nitro; and n is 2.

5. A compound of claim 4 wherein:

R$^1$ and R$^2$ are each methoxy; or R$^1$ and R$^2$ are taken together to form —X$^1$—(CH$_2$)$_r$—X$^2$—; or R$^1$ and R$^2$ are taken together with the carbon to which they are attached to form C(=O);

X$^1$ and X$^2$ are O;

R$^4$ and R$^5$ are independently H, methyl or halogen;

R$^6$ is OR$^{11}$;

R$^8$ is H or C$_1$–C$_2$ alkylsulfonyl; or R$^8$ is benzoyl or phenylsulfonyl, each optionally substituted with C$_1$–C$_3$ alkyl, halogen, cyano or nitro;

R$^{11}$ is H or C$_1$–C$_2$ alkylsulfonyl; or R$^{11}$ is benzoyl or phenylsulfonyl, each optionally substituted with C$_1$–C$_3$ alkyl, halogen, cyano or nitro; and m is 1; and r is 2.

6. A compound of claim 5 wherein:

R$^5$ is methyl or halogen and is attached to the phenyl ring position adjacent to the —S(O)$_n$— moiety.

7. The compound of claim 3 which is selected from the group:

2-[(2,3-dihydrospiro[4H-1-benzothiopyran-4,2'-[1,3]dioxolan]-6-yl)carbonyl]-1,3-cyclohexanedione S,S-dioxide;

(2,3-dihydrospiro[4H-1-benzothiopyran-4,2'-[1,3]dioxolan]-6-yl)(1-ethyl-5-hydroxy-1H-pyrazol-4-yl)methanone S,S-dioxide;

2-[(2,3-dihydro-5,8-dimethylspiro[4H-1-benzothiopyran-4,2'-[1,3]dioxolan]-6-yl)carbonyl]-1,3-cyclohexanedione S,S-dioxide;

(2,3-dihydro-5,8-dimethylspiro[4H-1-benzothiopyran-4,2'-[1,3]dioxolan]-6-yl)(1-ethyl-5-hydroxy-1H-pyrazol-4-yl)methanone S,S-dioxide;

6-[(1-ethyl-5-hydroxy-1H-pyrazol-4-yl)carbonyl]-2,3-dihydro-5,8dimethyl-4H-1-benzothiopyran-4-one 1,1-dioxide;

2-[(2,3-dihydro-5,3-dimethylspiro[4H-1-benzothiopyran-4,2'-[1,3]dioxolan]-6-yl)carbonyl]-1,3-cyclohexanedione; and (2,3-dihydro-5,8-dimethylspiro[4H-1-benzothiopyran-4,2'-[1,3]dioxolan]-6-yl)(1-ethyl-5-hydroxy-1H-pyrazol-4-yl)methanone.

8. A compound selected from Formula VII, and agriculturally suitable salts thereof,

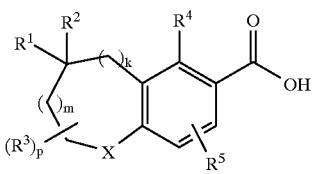

VII wherein
- $R^1$ and $R^2$ are each independently $C_1$–$C_6$ alkoxy, $C_2$–$C_6$ haloalkoxy, $C_1$–$C_6$ alkylthio or $C_2$–$C_6$ haloalkylthio; or $R^1$ and $R^2$ are taken together to form —$X^1$—$(CH_2)_r$—$X^2$—, —$(CH_2)_s$—$X^3$—, —$(CH_2)_t$—$X^3$—$CH_2$—, —$(CH_2)_v$—$X^3$—$CH_2CH_2$— or —$(CH_2)_w$—, each group optionally substituted with at least one member selected from 1–6 halogen, 1–6 $CH_3$ and one $C_1$–$C_3$ alkoxy; or $R^1$ and $R^2$ are taken together to form —O—N($C_1$–$C_3$ alkyl)—$CHR^{12}$—$CH_2$— or —O—N=$CHR^{12}$—$CH_2$—, each group optionally substituted with at least one member selected from 1–2 halogen and 1–2 $CH_3$;
- $X^1$ and $X^2$ are each independently O, S or N($C_1$–$C_3$ alkyl);
- $X^3$ is O or S;
- each $R^3$ is independently H or $CH_3$;
- $R^4$ and $R^5$ are each independently H, $C_1$–$C_6$ alkyl, $C_1$–$C_6$ haloalkyl, $C_1$–$C_6$ alkoxy, $C_1$–$C_6$ haloalkoxy, $C_1$–$C_6$ alkylthio, $C_1$–$C_6$ haloalkylthio, $C_1$–$C_6$ alkylsulfinyl, $C_1$–$C_6$ haloalkylsulfinyl, $C_1C_6$ alkylsulfonyl, $C_1$–$C_6$ haloalkylsulfonyl, halogen, cyano or nitro;
- $R^{12}$ is $C_1$–$C_3$ alkyl; or $R^{12}$ is phenyl optionally substituted with $C_1$–$C_3$ alkyl, halogen, cyano or nitro;
- X is $S(O)_n$;
- $R^{13}$ is H, $C_1$–$C_3$ alkyl, $C_3$–$C_4$ alkenyl, $C_3$–$C_4$ alkynyl, formyl, $C_2$–$C_3$ alkylcarbonyl, $C_2$–$C_3$ alkoxycarbonyl or $C_1$–$C_2$ alkylsulfonyl;
- k and m are each independently 0, 1 or 2, provided that the sum of k and m is 0, 1 or 2;
- n and p are each independently 0, 1 or 2;
- r is 2, 3 or 4;
- s is 2, 3, 4 or 5;
- t is 1, 2, 3 or 4;
- v is 2 or 3; and
- w is 2, 3, 4, 5 or 6.

9. A compound of claim 8 wherein:
- $R^1$ and $R^2$ are independently $C_1$–$C_6$ alkoxy, $C_2$–$C_6$ haloalkoxy, $C_1$–$C_6$ alkylthio or $C_2$–$C_6$ haloalkylthio; or $R^1$ and $R^2$ are taken together to form —$X^1$—$(CH_2)$—$X^2$— optionally substituted with at least one member selected from 1–6 halogen and 1–6 $CH_3$;
- $X^1$ and $X^2$ are both O or both S;
- X is $S(O)_n$;
- k is 0;
- m is 1 or 2; and
- r is 2 or 3.

10. A compound of claim 9 wherein:
- $R^4$ and $R^5$ are independently H, $C_1$–$C_3$ alkyl or halogen; and
- n is 2.

11. A compound of claim 10 wherein:
- $R^1$ and $R^2$ are each methoxy; or $R^1$ and $R^2$ are taken together to form —$X^1$—$(CH_2)_r$—$X^2$—;
- $X^1$ and $X^2$ are O;
- $R^4$ is methyl or halogen;
- $R^5$ is methyl or halogen and is attached to the phenyl ring position adjacent to the —$S(O)_n$— moiety;
- m is 1; and
- r is 2.

12. The compound of claim 9 which is selected from the group:
2,3-dihydro-5,8-dimethylspiro[4H-1-benzothiopyran-4,2'-[1,3]dioxolane]-6-carboxylic acid 1,1-dioxide; and
2,3-dihydro-5,8-dimethylspiro[4H-1-benzothiopyrano-4,2'-[1,3]dioxolane]-6-carboxylic acid.

13. A herbicidal composition comprising a herbicidally effective amount of a compound of claim 1 and at least one of a surfactant, a solid diluent or a liquid diluent.

14. A method for controlling the growth of undesired vegetation comprising contacting the vegetation or its environment with a herbicidally effective amount of a compound of claim 1.

* * * * *

UNITED STATES PATENT AND TRADEMARK OFFICE
CERTIFICATE OF CORRECTION

PATENT NO. : 5,952,266
DATED : SEPTEMBER 14, 1999
INVENTOR(S) : CHI-PING TSENG

It is certified that error appears in the above-identified patent and that said Letters Patent is hereby corrected as shown below:

In column 88, line 38, please change "—$X^1$—$(CH_2)$— "

to -- —$X^1$—$(CH_2)_r$— --.

Signed and Sealed this

Tenth Day of April, 2001

NICHOLAS P. GODICI

Attest:

Attesting Officer    Acting Director of the United States Patent and Trademark Office